US009481646B2

(12) United States Patent
Posner et al.

(10) Patent No.: US 9,481,646 B2
(45) Date of Patent: Nov. 1, 2016

(54) LOW CALCEMIC, HIGHLY ANTIPROLIFERATIVE, ANALOGS OF CALCITRIOL

(75) Inventors: Gary H. Posner, Baltimore, MD (US); Kimberly S. Petersen, College Park, MD (US); Lindsey C. Hess, Baltimore, MD (US); Douglas T. Genna, Timonium, MD (US); Scott Borella, Charlotte, NC (US)

(73) Assignee: The Johns Hopkins University, Baltimore, MD (US)

( * ) Notice: Subject to any disclaimer, the term of this patent is extended or adjusted under 35 U.S.C. 154(b) by 795 days.

(21) Appl. No.: 12/596,252

(22) PCT Filed: Apr. 18, 2008

(86) PCT No.: PCT/US2008/060885
§ 371 (c)(1),
(2), (4) Date: Jan. 28, 2010

(87) PCT Pub. No.: WO2008/131267
PCT Pub. Date: Oct. 30, 2008

(65) Prior Publication Data
US 2010/0137262 A1  Jun. 3, 2010

Related U.S. Application Data

(60) Provisional application No. 60/923,998, filed on Apr. 18, 2007.

(51) Int. Cl.
*C07C 401/00* (2006.01)
*C07D 307/02* (2006.01)
*C07D 307/42* (2006.01)

(52) U.S. Cl.
CPC ........... *C07C 401/00* (2013.01); *C07D 307/42* (2013.01); *C07C 2101/14* (2013.01); *C07C 2101/16* (2013.01)

(58) Field of Classification Search
USPC .......................................... 514/167; 552/653
See application file for complete search history.

(56) References Cited

U.S. PATENT DOCUMENTS

| 4,552,105 A * | 11/1985 | Nagashima ............... 123/198 R |
| 4,758,382 A * | 7/1988 | Sterling et al. ............... 552/653 |
| 4,897,387 A * | 1/1990 | Ikekawa et al. .............. 514/167 |
| 4,927,815 A * | 5/1990 | DeLuca et al. ............... 514/167 |
| 5,274,142 A * | 12/1993 | Posner et al. ................ 552/653 |
| 5,387,582 A * | 2/1995 | Hansen ................ C07C 401/00 514/167 |
| 6,389,498 B1 * | 5/2002 | Edwards et al. ............... 710/268 |
| 6,448,421 B1 * | 9/2002 | Yamauchi ..................... 552/653 |
| 6,479,538 B1 * | 11/2002 | Reddy ........................... 514/451 |
| 6,537,980 B1 * | 3/2003 | Hansen ................ C07C 401/00 514/167 |
| 6,646,143 B2 * | 11/2003 | Hansen ......................... 552/653 |
| 6,858,595 B2 * | 2/2005 | Hayes et al. .................. 514/167 |
| 6,982,258 B2 * | 1/2006 | Posner et al. ................. 514/167 |
| 7,074,777 B2 * | 7/2006 | Kawase et al. ............... 514/167 |
| 7,901,698 B2 * | 3/2011 | Zanutto .................. A61K 31/59 424/401 |
| 8,455,466 B2 * | 6/2013 | Binderup et al. ............. 514/167 |
| 8,796,246 B2 * | 8/2014 | Fujieda ................ C07C 401/00 514/167 |
| 2003/0195176 A1 | 10/2003 | Kawase et al. |
| 2014/0206655 A1 * | 7/2014 | DeLuca et al. ............... 514/167 |

FOREIGN PATENT DOCUMENTS

| EP | 1275543 A | 1/2003 |
| EP | 1 178 960 B1 | 11/2003 |
| WO | WO 91/09841 A | 7/1991 |
| WO | WO 91/09841 A1 | 7/1991 |
| WO | WO 91/15475 A | 10/1991 |
| WO | WO 91/15475 A1 | 10/1991 |
| WO | WO 00/64869 A | 11/2000 |
| WO | WO 01/56981 A | 8/2001 |
| WO | WO 01/56981 A1 | 8/2001 |
| WO | WO 2006/074227 A | 7/2006 |
| WO | WO 2006/074227 A2 | 7/2006 |
| WO | WO 2007/142158 | 12/2007 |

OTHER PUBLICATIONS

Gniadecki et al. (British Journal of Dermatology 1995: 132: 841-852).*
Kamao et al. (AN 2003:25813, DN 138:315029, abstract of Journal of Biological Chemistry (2003), 278(3) 1463-.*
Posner et al. (AN 2006:678581, ZCAPLUS, DN 145:145926), abstract of WO 2006074227).*
Peterson et al. (J. Med. Chem. 2007, 50, 5824-5832).*
Database Chemabs Chemical Abstracts Service, "Preparation of 9,10-Secopregnane Derivatives as Useful Vitamin D3 Derivatives," XP-002490665 Accession No. 1034, Database Accession No. 2007:1420037 (2007), Abstract, Columbus Ohio.
Fall et al., "Stereoselective Synthesis of 22-Oxacalcitriol (OCT) and Analogues Modified at C25," *Tetrahedron Letters* (2002), 427-429, Elsevier Science Ltd.
Jensen et al., "Prediction of in vitro Metabolic Stability of Calcitriol Analogs by QSAR," *Journal of Computer-Aided Molecular Design* (2003), 17:849-859, XP002490574, Kluwer Academic Publishers, the Netherlands.
Kubodera, Noboru, "Search for and Development of Active Vitamin D3 Analogs," *Current Bioactive Compounds* (2006), 2:301-315, Bentham Science Publishers Ltd.
Shimizu et al., "Novel Vitamin D3 Antipsoriatic Antegrugs: 16-En-22-oxa-1α,25-(OH)$_2$D$_3$ Analogs," *Bioorganic & Medicinal Chemistry* (2006) 14:1838-1850, Elsevier Ltd.
Fall et al., "Stereoselective synthesis of 22-oxacalcitriol (OCT) and analogues modified at C25", *Tetrahedron Letters*, 43:427-429 (2002).
Jensen et al., "Prediction of in vitro metabolic stability of calcitriol analogs by QSAR", *J Comput Aided Mol Des.*, 17(12):849-59 (2003).

* cited by examiner

*Primary Examiner* — Sabiha N Qazi
(74) *Attorney, Agent, or Firm* — DLA Piper LLP (US)

(57) ABSTRACT

The disclosure provides compounds, compositions and methods using these compounds and compositions to stimulate the differentiation of cells and inhibit excessive cell proliferation of certain cells, including cancer cells and skin cells, which may be useful in the treatment of diseases characterized by abnormal cell proliferation and/or cell differentiation such as leukemia, myelofibrosis and psoriasis without the well known effect on calcium metabolism, which gives rise to hypercalcemia.

6 Claims, 9 Drawing Sheets

■ Calcitriol $B_{50}$ = 1.90 nM
▲ Analog 1f $B_{50}$ = 367.3 nM

LOW CALCEMIC, HIGHLY ANTIPROLIFERATIVE, ANALOGS OF CALCITRIOL

CROSS-REFERENCES TO RELATED APPLICATIONS

This application is a 35 USC §371 National Stage application of International Application No. PCT/US2008/060885 filed Apr. 18, 2008, now pending; which claims the benefit under 35 USC §119(e) to U.S. application Ser. No. 60/923,998 filed Apr. 18, 2007, now abandoned. The disclosure of each of the prior applications is considered part of and is incorporated by reference in the disclosure of this application.

STATEMENT AS TO RIGHTS TO INVENTIONS MADE UNDER FEDERALLY SPONSORED RESEARCH OR DEVELOPMENT

This study was supported in-part by the National Institute of Health under CA 93547. The U.S. government may have certain rights in the invention.

BACKGROUND OF THE DISCLOSURE

Steroid hormones are necessary for good health in humans. [Witzmann, R., *Steroids: Keys to Life*, Van Nostrand Reinhold Co., New York, N.Y., 1977; Hammes, S. R., *Proc. Nat'l. Acad. Sci.* 2003, 1009 21680-21700.] For example, these compounds are useful in the treatment and/or prevention of cancer, dermatological disorders, bone disorders, parathyroid disorders, immunological disorders, wound healing and osteoporosis. Over the years, diverse oxa steroids have been prepared to probe how the replacement of a —$CH_2$ group by an O-atom affects biological activity. Significant and valuable biological benefits have been recorded for some oxa steroids including: (1) 6-oxa steroids as $GABA_A$ receptor modulators [Nicoletti, S. R. et al., *Steroids* 2000, 65, 349-356]; (2) 7-oxa steroids as potent and selective progesterone receptor antagonists [Kang, F. A. et al.; *Bioorg. Med. Chem. Lett.* 2007, 17, 907-910]; (3) 11-oxa steroids as progestational agents [Engel, C. R. et al.; *Steroids* 1986, 47, 381-399; Cachoux, F.; *Tetrahedron Lett.* 2000, 41, 1767-1769]; and (4) 15-oxa steroids as estrogenic agents [Rosen, P. et al.; *J. Med. Chem.* 1980, 23, 329-330].

Some oxa analogs of the vitamin D seco-steroids have also been reported [Calverley, M. J. et al.; Analogues, U.S. Pat. Nos. 5,378,695 and 5,401,732 (1995)]. The most noteworthy oxa analog of the natural hormone 1α,25-dihydroxyvitamin D3 (calcitriol, A) is the Chugai Pharmaceutical Company's maxacalcitol B [Kubodera, N., *Current Bioactive Compounds* 2006, 2, 301-315]. This 22-oxa-25-OH analog is currently a clinically used drug for the treatment of secondary hyperparathyroidism and is a drug candidate for the topical treatment of psoriasis, an immune-mediated, chronic skin disease. Other 23-oxa-25-hydroxy analogs of the natural hormone A have been studied, but none surpasses or even matches Chugai's drug 22-oxa-25-hydroxy B in terms of favorable separation of antiproliferative and/or prodifferentiation activity from unfavorable calcemic activity. [Steinmeyer, A., et al.; *Curr. Pharm. Des.* 2000, 6, 767-789] For example, in a broad study of structure-activity relationships (SAR) in 23-oxa-25-hydroxy analogs of A, the Schering Corporation found that the potential therapeutic window between desirably high antiproliferative or prodifferentiation activity and desirably low calcemic activity was small for 23-oxa calcitriol, 20-ene-23-oxa calcitriol, and 22-ene-25-oxa calcitriol [Steinmeyer, A., et al.; *Curr. Pharm. Des.* 2000, 6, 767-789], compared to a big therapeutic window for the Chugai drug 22-oxa-25-hydroxy B. [Allewaert, K. et al.; *Steroids* 1994, 59, 686-690].

Thus, what is needed in the art are other analogs of the vitamin D seco-steroids that selectively exhibit desirable pharmacological activities but not exhibit hypercalcemic and other undesirable activities.

SUMMARY OF THE DISCLOSURE

The disclosure provides biologically active analogs of the natural hormone A that lack the conventional 25-OH group [Sinishtaj, S. et al.; *Bioorg. Med. Chem.* 2006, 14, 6341-6348; Agoston, E. S. et al.; *Anti-Cancer Agents Med. Chem.* 2006, 6, 53-71; Kahraman, M. et al.; Sinishtaj, S.; Dolan, P. M.; Kensler, T. W.; Peleg, S.; Saha, U.; Chuang, S. S.; Bernstein, G.; Korczak, B.; Posner, G. H. Potent, selective and low-calcemic inhibitors of CYP24Hydroxylase: 24-Sulfoximine analogues of the hormone 1α,25-dihydroxyvitamin $D_3$. 2004, 47, 6854-6863]. In some embodiments, the natural 25-OH group is removed and the natural 23-$CH_2$ group is replaced by an oxygen atom. This overall balanced removal of oxygen from position-25 and introduction of oxygen at position-23 has produced several new vitamin D ether analogs with high therapeutic potential. The disclosed series may be easily synthesized using allylic, benzylic, and propargylic ether analogs 1 in which an oxygen atom is located at position-23 on the C,D-ring side chain and, for the first time, in which the standard side-chain terminal —OH group is absent. Despite the absence of this terminal —OH group, thought to be essential for effective binding to the vitamin D receptor (VDR) [Feldman, D. et al.; Eds. Vitamin D. 2nd Ed., Elsevier, 2005], the disclosed analogs have high antiproliferative activity in vitro and desirably low calciuric activity in vivo.

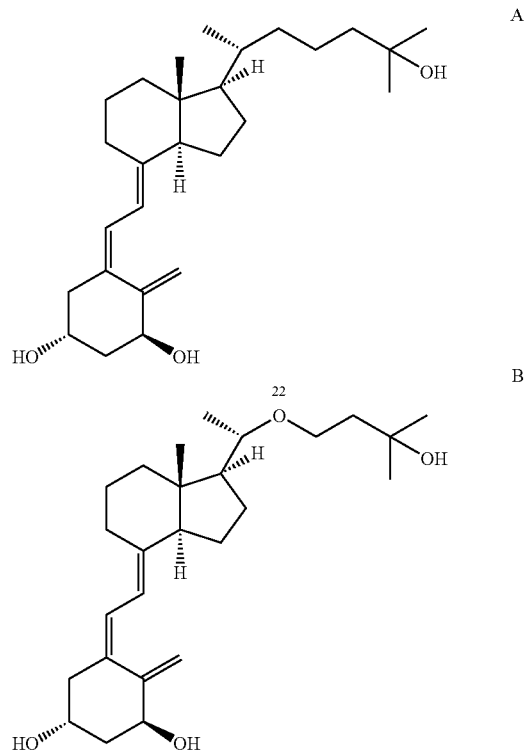

-continued

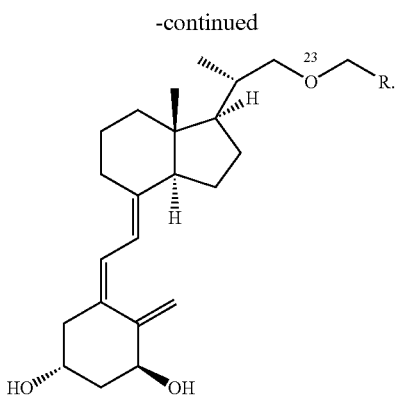

Thus, in one aspect the disclosure provides compounds having formula I:

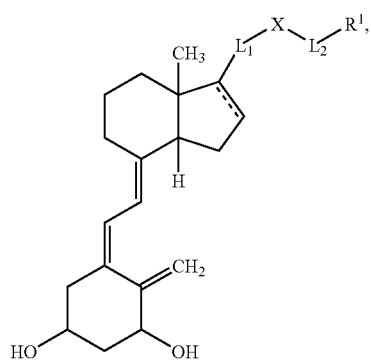

or a pharmaceutically acceptable salt or solvate thereof, wherein:
    ≡ is a single or double bond;
    X is independently O, $NR^2$, S, S(O), or $S(O)_2$;
    $L_1$ is independently a direct bond, or substituted or unsubstituted alkyl, wherein alkyl is optionally independently substituted with 1 to 3 $R^9$ groups;
    $L_2$ is independently a direct bond, or substituted or unsubstituted alkyl, wherein alkyl is optionally independently substituted with 1 to 3 $R^9$ groups;
    $R^1$ is independently substituted or unsubstituted alkyl, substituted or unsubstituted cycloalkyl, substituted or unsubstituted alkenyl, substituted or unsubstituted cycloalkenyl, substituted or unsubstituted alkynyl, substituted or unsubstituted aryl, substituted or unsubstituted arylalkyl, substituted or unsubstituted heteroaryl, or substituted or unsubstituted heteroarylalkyl, wherein $R^1$ is optionally independently substituted with 1 to 5 $R^3$ groups;
    $R^2$ is H, alkyl, or perfluoroalkyl;
    $R^3$ is independently H, F, Cl, Br, I, OH, CN, $NO_2$, substituted or unsubstituted alkyl, perfluoroalkyl, substituted or unsubstituted cycloalkyl, substituted or unsubstituted alkenyl, substituted or unsubstituted cycloalkenyl, substituted or unsubstituted alkynyl, substituted or unsubstituted aryl, substituted or unsubstituted arylalkyl, substituted or unsubstituted heteroaryl, substituted or unsubstituted heteroarylalkyl, —$(CH_2)_jOR^4$, —$(CH_2)_jC(O)R^4$, —$(CH_2)_jC(NR^7)R^4$, —$(CH_2)_jC(NNR^7)R^4$, —$(CH_2)_jC(O)OR^4$, —$(CH_2)_jNR^5R^6$, —$(CH_2)_jC(O)NR^5R^6$, —$(CH_2)_jOC(O)NR^5R^6$, —$(CH_2)_jNR^7C(O)R^4$, —$(CH_2)_jNR^7C(O)OR^4$, —$(CH_2)_jNR^7C(O)NR^5R^6$, —$(CH_2)_jS(O)_mR^8$, —$(CH_2)_jNR^7S(O)_2R^8$, or —$(CH_2)_jS(O)_2NR^5R^6$, wherein each j is independently an integer from 0 to 6, wherein m is independently an integer from 0 to 2, and wherein alkyl, cycloalkyl, alkenyl, cycloalkenyl, alkynyl, aryl, arylalkyl, heteroaryl, and heteroarylalkyl are each optionally independently substituted with 1 to 3 $R^9$ groups;
    $R^4$ is independently H, substituted or unsubstituted alkyl, perfluoroalkyl, substituted or unsubstituted cycloalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, wherein $R^4$ is optionally independently substituted with 1 to 3 $R^9$ groups;
    $R^5$, $R^6$, $R^7$ and $R^8$ are each independently a direct bond, H, OH, —$(CH_2)_jOR^9$, substituted or unsubstituted alkyl, perfluoroalkyl, substituted or unsubstituted cycloalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, wherein $R^5$, $R^6$, $R^7$, and $R^8$ are each optionally independently substituted with 1 to 3 $R^9$ groups, or
    $R^7$ and $R^8$ are as described above, and $R^5$ and $R^6$, together with the N atom to which they are attached, form substituted or unsubstituted heterocycloalkyl, or substituted or unsubstituted heteroaryl, wherein $R^5$ and $R^6$ are each optionally independently substituted with 1 to 3 $R^9$ groups; and
    $R^9$ is H, F, Cl, Br, I, OH, CN, $NO_2$, alkyl, perfluoroalkyl, cycloalkyl, alkenyl, cycloalkenyl, alkynyl, aryl, arylalkyl, heteroaryl, heteroarylalkyl, —$(CH_2)_jOR^{10}$, —$(CH_2)_jC(O)R^{10}$, —$(CH_2)_jC(NR^{13})R^4$, —$(CH_2)_jC(O)OR^{10}$, —$(CH_2)_jNR^{11}R^{12}$, —$(CH_2)_jC(O)NR^{11}R^{12}$, —$(CH_2)_jOC(O)NR^{11}R^{12}$, —$(CH_2)_jNR^{13}C(O)R^{14}$, —$(CH_2)_jNR^{13}C(O)OR^{10}$, —$(CH_2)_jNR^{13}C(O)NR^{11}R^{12}$, —$(CH_2)_jS(O)_mR^{15}$, —$(CH_2)_jNR^{13}S(O)_2R^{15}$, or —$(CH_2)_jS(O)_2NR^{11}R^{12}$; wherein each j is independently an integer from 0 to 6, wherein m is independently an integer from 0 to 2; and
    $R^{10}$, $R^{11}$, $R^{12}$, $R^{13}$, $R^{14}$ and $R^{15}$ are each independently H, F, Cl, Br, I, OH, CN, $NO_2$, alkyl, perfluoroalkyl, cycloalkyl, alkenyl, cycloalkenyl, alkynyl, aryl, arylalkyl, heteroaryl, or heteroarylalkyl.

In other aspects the disclosure provides: pharmaceutical compositions containing one or more of the compounds of formula I; methods for treating disorders characterized by abnormal cell-proliferation and/or cell-differentiation by administering a compound of formula I or a pharmaceutical composition containing a compound of formula I; methods for treating secondary hyperparathyroidism by administering a compound of formula I or a pharmaceutical composition containing a compound of formula I; and methods for preparing a compound of formula I.

BRIEF DESCRIPTION OF THE DRAWINGS

FIG. 2 illustrates the VDR binding assay results for compound 1a.

DETAILED DESCRIPTION OF THE DISCLOSURE

General

Figure 1:
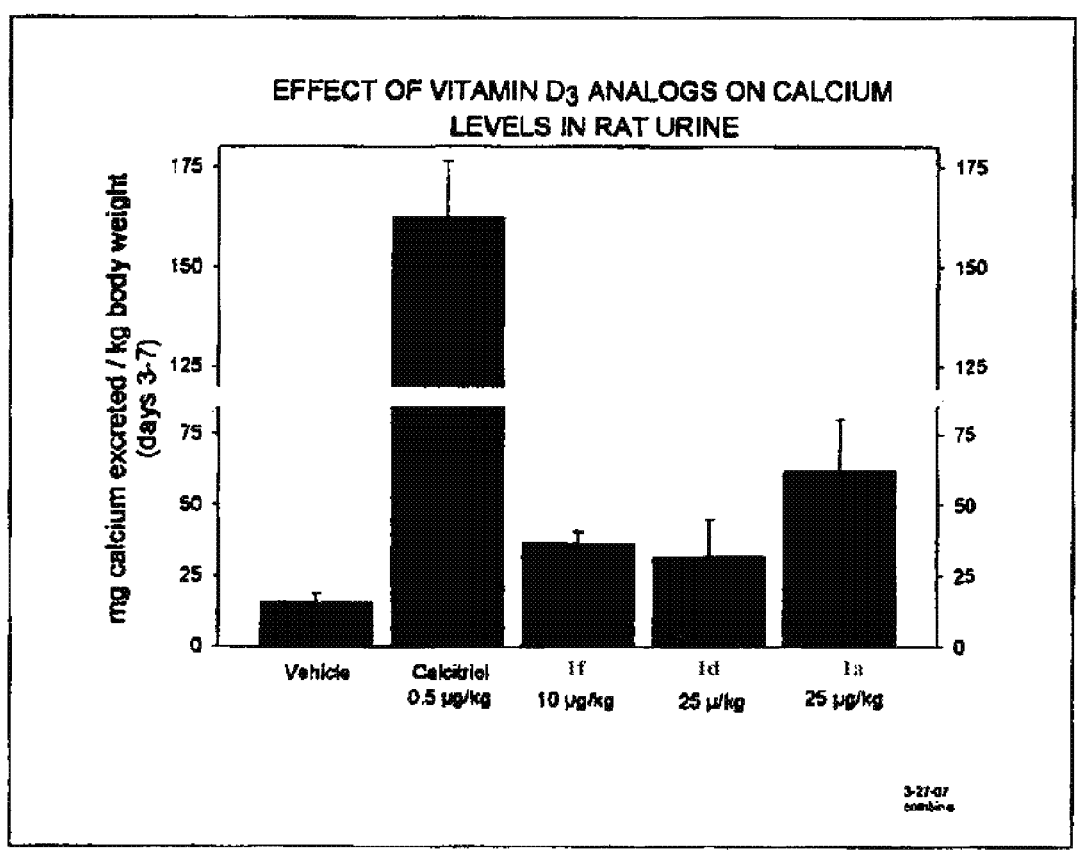
FIG. 1 illustrates the in-vivo assay showing the effect of the disclosed vitamin $D_3$ analogs on calcium levels in rat urine.
Figure 2:
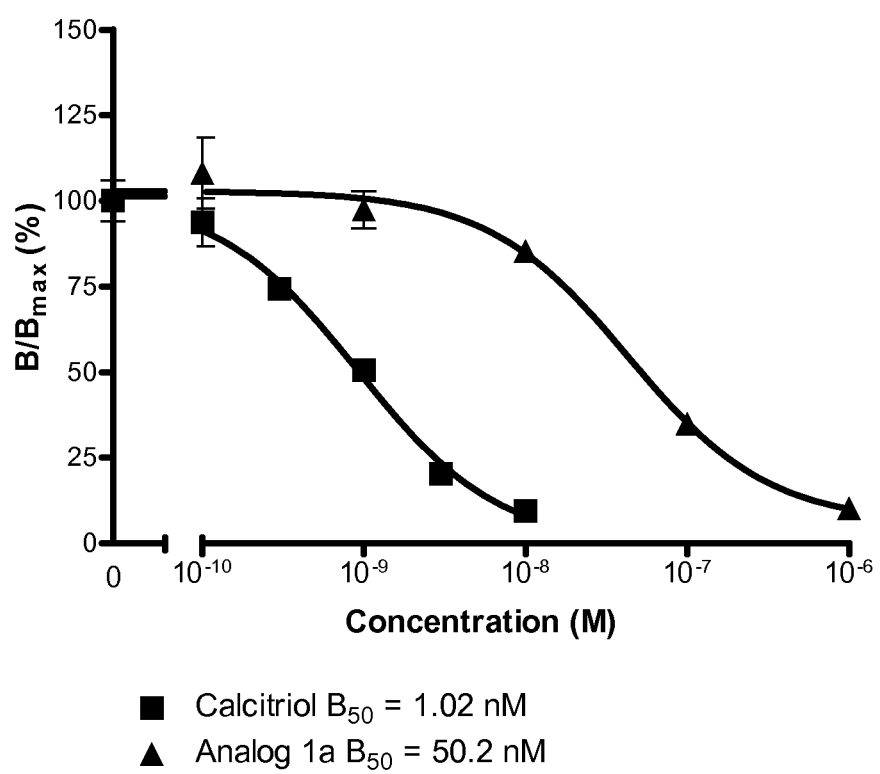
Figure 3:
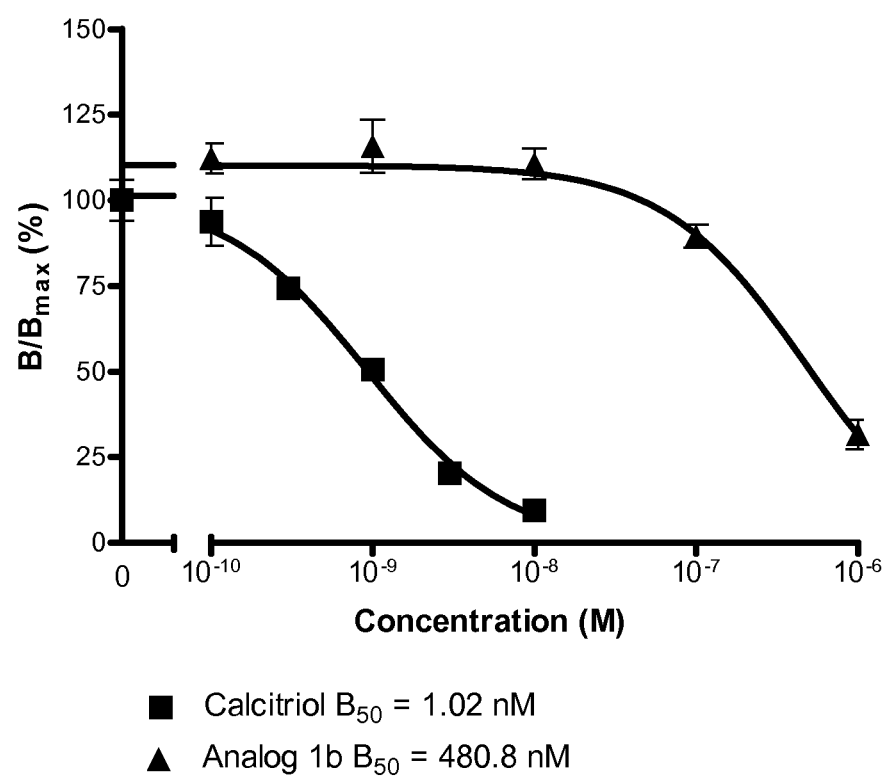
FIG. 3 illustrates the VDR binding assay results for compound 1b.
Figure 4:
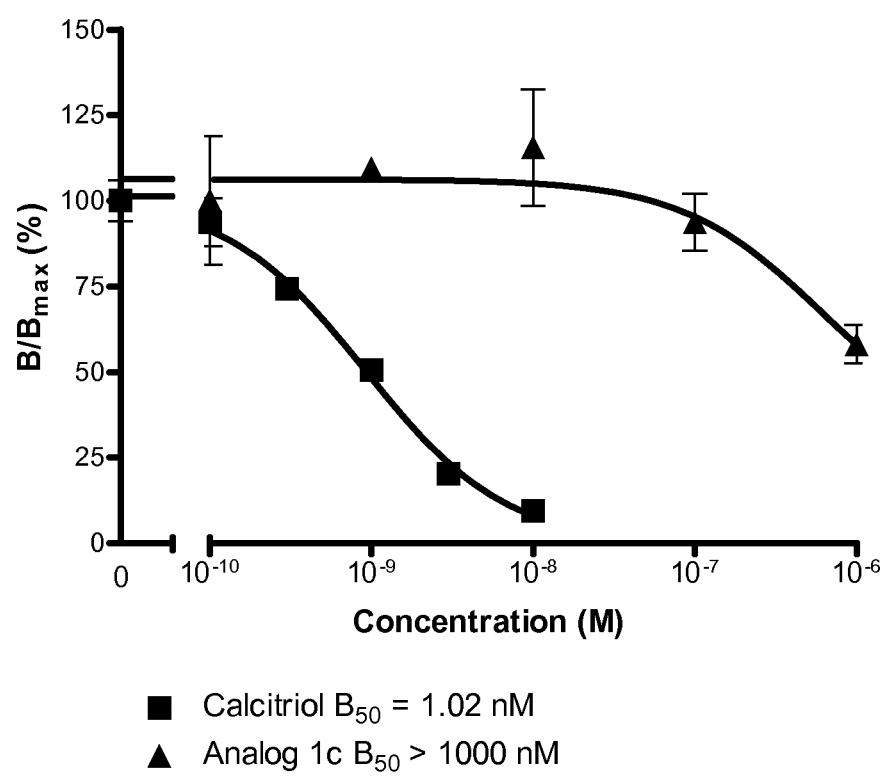
FIG. 4 illustrates the VDR binding assay results for compound 1c.
Figure 5:
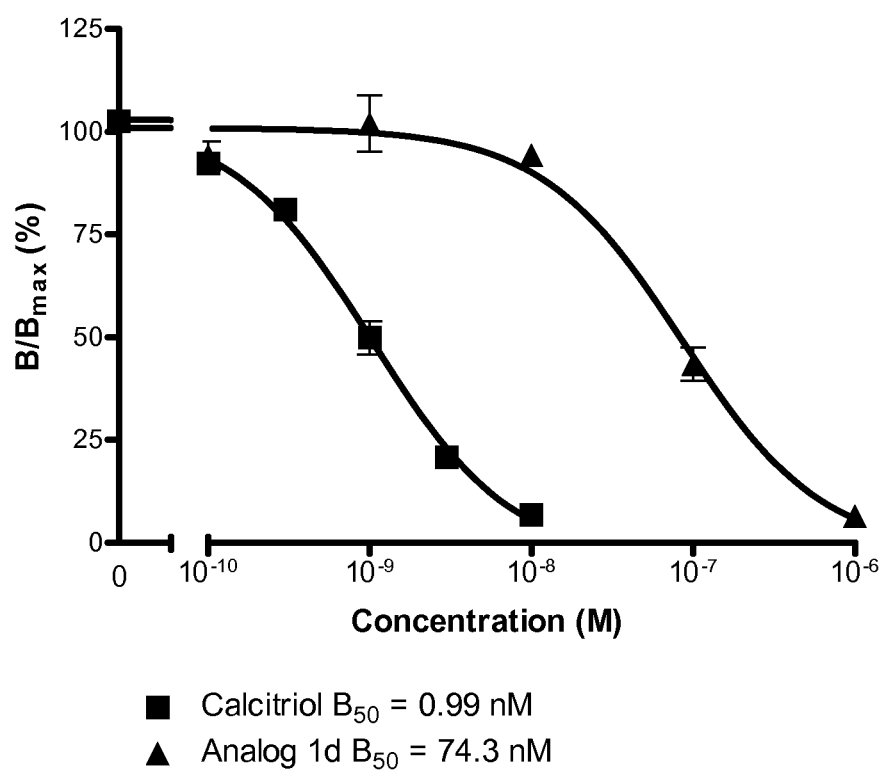
FIG. 5 illustrates the VDR binding assay results for compound 1d.
Figure 6:
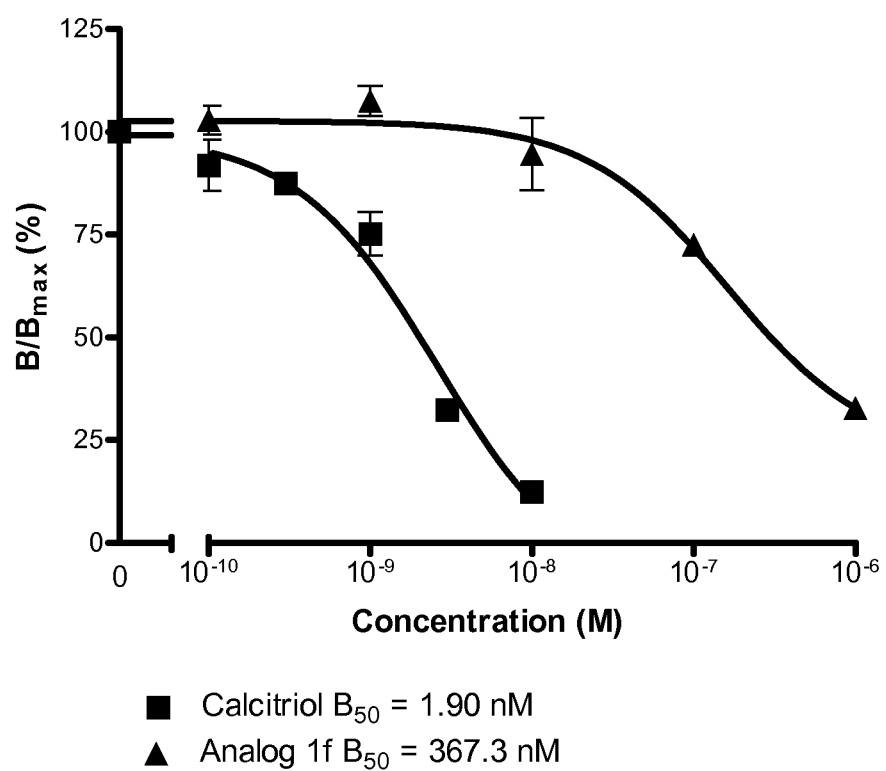
FIG. 6 illustrates the VDR binding assay results for compound 1f.
Figure 7:
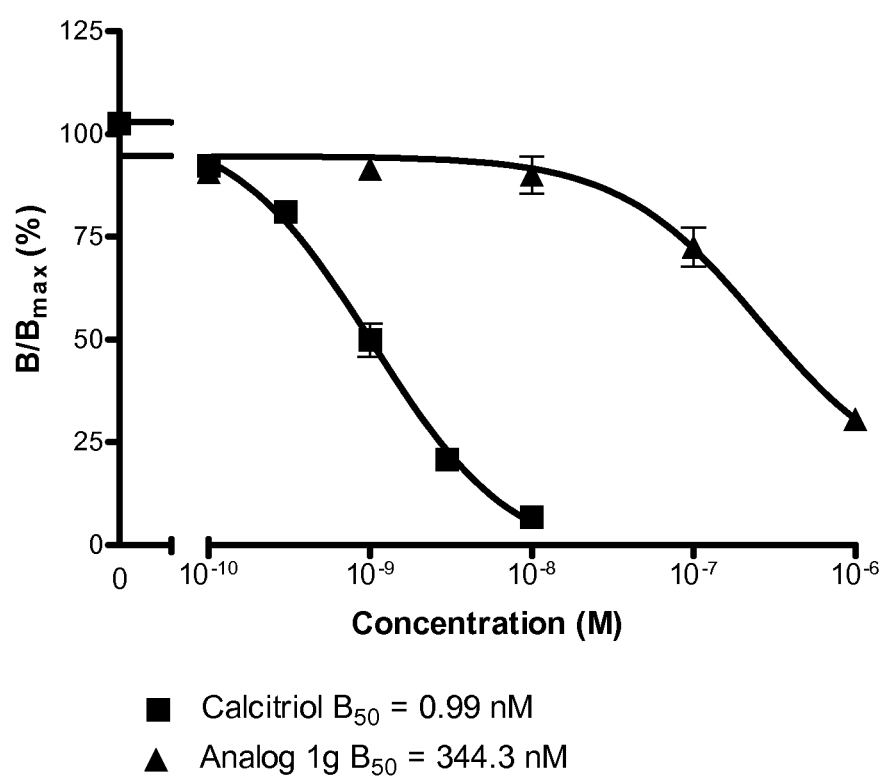
FIG. 7 illustrates the VDR binding assay results for compound 1g.
Figure 8:
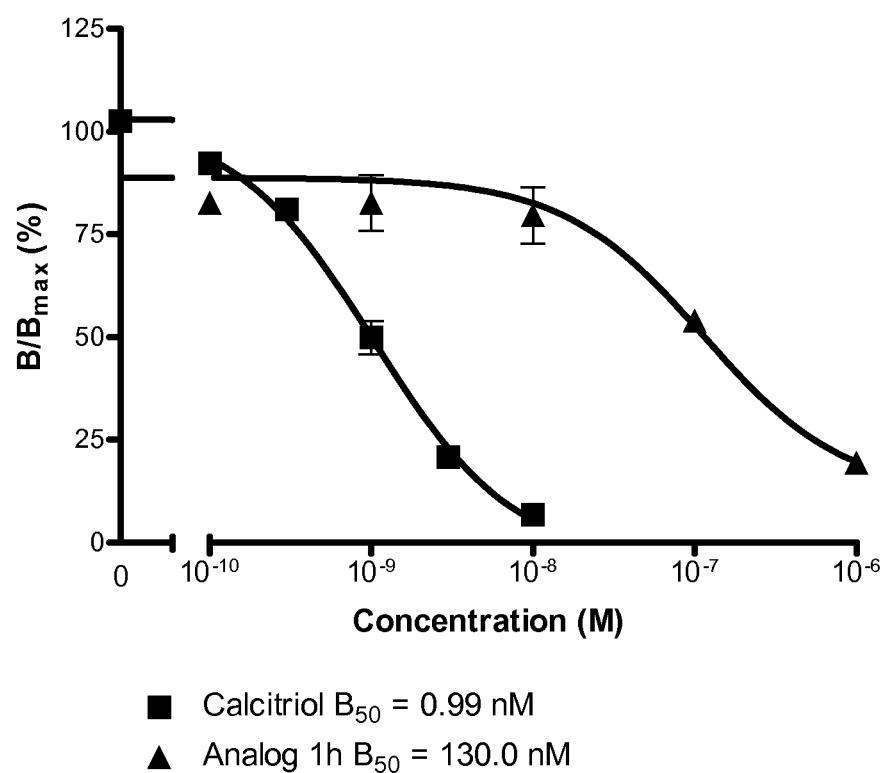
FIG. 8 illustrates the VDR binding assay results for compound 1h.
Figure 9:
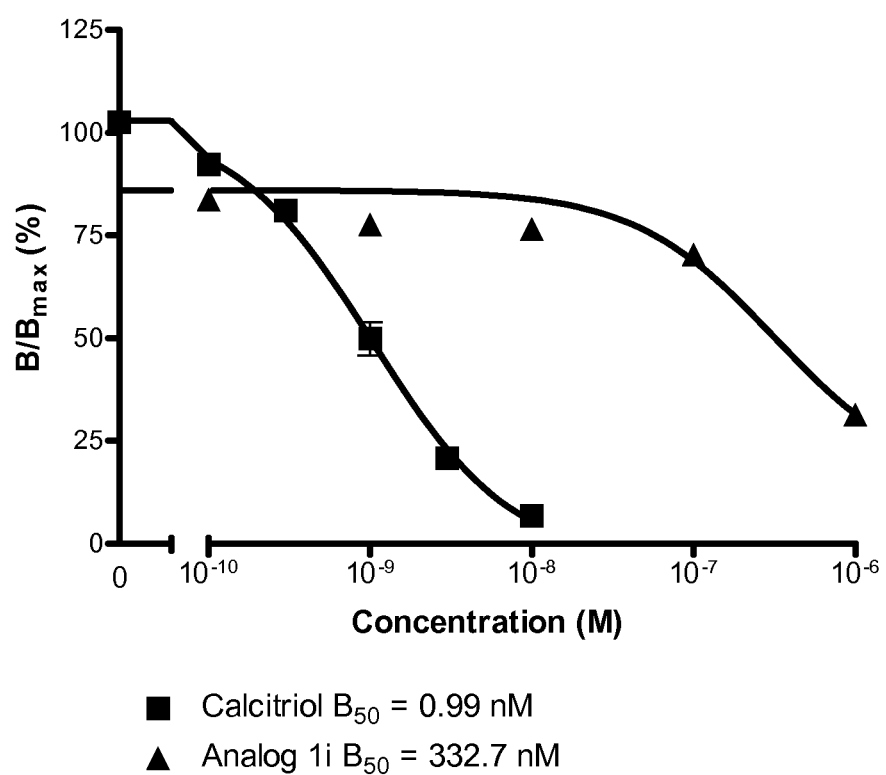
FIG. 9 illustrates the VDR binding assay results for compound 1i.

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or cyclic hydrocarbon group, or combination thereof, which may be fully saturated, mono- or polyunsaturated and can include di- and multivalent groups, having the number of carbon atoms designated (i.e. C$_1$-C$_{10}$ means one to ten carbons). Examples of saturated hydrocarbon groups include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent group derived from an alkyl, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$.

Similarly, the term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "cycloalkyl" or "cycloalkylalkyl" also refers to a 3 to 7 membered cycloalkyl group attached to the remainder of the molecule via an unsubstituted alkylene group. Recitation of a specific number of carbon atoms (e.g. C$_1$-C$_{10}$ cycloalkylalkyl) refers to the number of carbon atoms in the alkylene group.

The term "heterocycloalkyl" or "heterocycloalkylalkyl" also refers to a 3 to 7 membered heterocycloalkyl group attached to the remainder of the molecule via an unsubstituted alkylene group. Recitation of a specific number of carbon atoms (e.g. C$_1$-C$_{10}$ hetero-cycloalkylalkyl) refers to the number of carbon atoms in the alkylene group.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, an aromatic, hydrocarbon substituent which may be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group may be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl. Substituents for each of above noted aryl and heteroaryl ring systems are selected from the group of acceptable substituents described below. The terms "arylene" and "heteroarylene" refer to the divalent derivatives of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those groups in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent derivatives) are meant to include both substituted and unsubstituted forms of the indicated group. Preferred substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) may be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such group. R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R''' and R'''' groups when more than one of these groups is present. When R' and R" are attached to the same nitrogen atom, they may be combined with the nitrogen atom to form a 4-, 5-, 6-, or 7-membered ring. For example, —NR'R" is meant to include, but not be limited to, 1-pyrrolidinyl and 4-morpholinyl. From above discussion of substituents, one of skill in art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts may be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogen-phosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present disclosure, whether radioactive or not, are encompassed within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts may be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts may be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

In addition to salt forms, the present disclosure relates to compounds, which are in a prodrug form. Prodrugs of the compounds described herein are those compounds that readily undergo chemical changes under physiological conditions to provide the compounds of the present disclosure. Additionally, prodrugs may be converted to the compounds of the present disclosure by chemical or biochemical methods in an ex vivo environment. For example, prodrugs may be slowly converted to the compounds of the present disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, physiological conditions.

The terms "treating" or "treatment" in reference to a particular disease includes prevention of the disease.

The structure:

signifies the point of attachment of a moiety "R" to the remainder of the molecule.

The structure:

signifies mixtures of α- and β-isomers.

Analogs of Calcitriol

The disclosure provides compounds, compositions and methods using these compounds and compositions to stimulate the differentiation of cells and inhibit excessive cell proliferation of certain cells, including cancer cells and skin cells. The disclosed compounds, compositions and methods may be useful in the treatment of diseases characterized by abnormal cell proliferation and/or cell differentiation such as leukemia, myelofibrosis and psoriasis without the well known effect on calcium metabolism, which gives rise to hypercalcemia. The disclosure further provides these compounds and compositions, along with dosage units of such preparations, which are useful in methods for treating diseases characterized by abnormal cell differentiation and/or cell proliferation.

Thus, in one aspect the disclosure provides compounds having formula I:

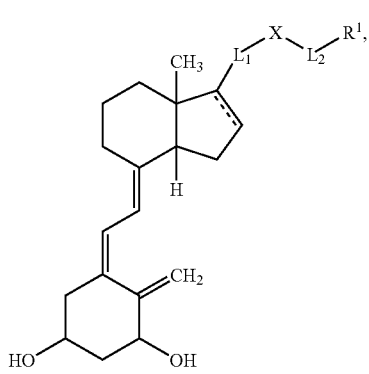

or a pharmaceutically acceptable salt or solvate thereof, wherein:

═══ is a single or double bond;

X is independently O, $NR^2$, S, S(O), or $S(O)_2$;

$L_1$ is independently a direct bond, or substituted or unsubstituted alkyl, wherein alkyl is optionally independently substituted with 1 to 3 $R^9$ groups;

$L_2$ is independently a direct bond, or substituted or unsubstituted alkyl, wherein alkyl is optionally independently substituted with 1 to 3 $R^9$ groups;

$R^1$ is independently substituted or unsubstituted alkyl, substituted or unsubstituted cycloalkyl, substituted or unsubstituted alkenyl, substituted or unsubstituted cycloalkenyl, substituted or unsubstituted alkynyl, substituted or unsubstituted aryl, substituted or unsubstituted arylalkyl, substituted or unsubstituted heteroaryl, or substituted or unsubstituted heteroarylalkyl, wherein $R^1$ is optionally independently substituted with 1 to 5 $R^3$ groups;

$R^2$ is H, alkyl, or perfluoroalkyl;

$R^3$ is independently H, F, Cl, Br, I, OH, CN, $NO_2$, substituted or unsubstituted alkyl, perfluoroalkyl, substituted or unsubstituted cycloalkyl, substituted or unsubstituted alkenyl, substituted or unsubstituted cycloalkenyl, substituted or unsubstituted alkynyl, substituted or unsubstituted aryl, substituted or unsubstituted arylalkyl, substituted or unsubstituted heteroaryl, substituted or unsubstituted heteroarylalkyl, $-(CH_2)_jOR^4$, $-(CH_2)_jC(O)R^4$, $-(CH_2)_jOC(NR^7)R^4$, $-(CH_2)_jC(NNR^7)R^4$, $-(CH_2)_jC(O)OR^4$, $-(CH_2)_jNR^5R^6$, $-(CH_2)_jC(O)NR^5R^6$, $-(CH_2)_jOC(O)NR^5R^6$, $-(CH_2)_jNR^7C(O)R^4$, $-(CH_2)_jNR^7C(O)OR^4$, $-(CH_2)_jNR^7C(O)NR^5R^6$, $-(CH_2)_jS(O)_mR^8$, $-(CH_2)_jNR^7S(O)_2R^8$, or $-(CH_2)_jS(O)_2NR^5R^6$, wherein each j is independently an integer from 0 to 6, wherein m is independently an integer from 0 to 2, and wherein alkyl, cycloalkyl, alkenyl, cycloalkenyl, alkynyl, aryl, arylalkyl, heteroaryl, and heteroarylalkyl are each optionally independently substituted with 1 to 3 $R^9$ groups;

$R^4$ is independently H, substituted or unsubstituted alkyl, perfluoroalkyl, substituted or unsubstituted cycloalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, wherein $R^4$ is optionally independently substituted with 1 to 3 $R^9$ groups;

$R^5$, $R^6$, $R^7$ and $R^8$ are each independently a direct bond, H, OH, $-(CH_2)_jOR^9$, substituted or unsubstituted alkyl, perfluoroalkyl, substituted or unsubstituted cycloalkyl, substituted or unsubstituted heteroalkyl, substituted or unsubstituted heterocycloalkyl, substituted or unsubstituted aryl, substituted or unsubstituted arylalkyl, substituted or unsubstituted heteroaryl, or substituted or unsubstituted heteroarylalkyl, wherein $R^5$, $R^6$, $R^7$, and $R^8$ are each optionally independently substituted with 1 to 3 $R^9$ groups, or $R^7$ and $R^8$ are as described above, and $R^5$ and $R^6$, together with the N atom to which they are attached, form substituted or unsubstituted heterocycloalkyl, or substituted or unsubstituted heteroaryl, wherein $R^5$ and $R^6$ are each optionally independently substituted with 1 to 3 $R^9$ groups; and $R^9$ is H, F, Cl, Br, I, OH, CN, $NO_2$, alkyl, perfluoroalkyl, cycloalkyl, alkenyl, cycloalkenyl, alkynyl, aryl, arylalkyl, heteroaryl, heteroarylalkyl, $-(CH_2)_jOR^{10}$, $-(CH_2)_jC(O)R^{10}$, $-(CH_2)_jC(NR^{13})R^4$, $-(CH_2)_jC(O)OR^{10}$, $-(CH_2)_jNR^{11}R^{12}$, $-(CH_2)_jC(O)NR^{11}R^{12}$, $-(CH_2)_jOC(O)NR^{11}R^{12}$, $-(CH_2)_jNR^{13}C(O)R^{14}$, $-(CH_2)_jNR^{13}C(O)OR^{10}$, $-(CH_2)_jNR^{13}C(O)NR^{11}R^{12}$, $-(CH_2)_jS(O)_mR^{15}$, $-(CH_2)_jNR^{13}S(O)_2R^{15}$, or $-(CH_2)_jS(O)_2NR^{11}R^{12}$; wherein each j is independently an integer from 0 to 6, wherein m is independently an integer from 0 to 2; and $R^{10}$, $R^{11}$, $R^{12}$, $R^{13}$, $R^{14}$ and $R^{15}$ are each independently H, F, Cl, Br, I, OH, CN, $NO_2$, alkyl, perfluoroalkyl, cycloalkyl, alkenyl, cycloalkenyl, alkynyl, aryl, arylalkyl, heteroaryl, or heteroarylalkyl.

In another aspect the disclosure provides compounds of formula I, wherein:

X is independently O;

$L_1$ is independently a direct bond, or $(C_1-C_6)$alkyl;

$L_2$ is independently a direct bond, or $(C_1-C_6)$alkyl;

$R^1$ is independently substituted or unsubstituted alkyl, substituted or unsubstituted cycloalkyl, substituted or unsubstituted alkenyl, substituted or unsubstituted cycloalkenyl, or substituted or unsubstituted alkynyl; and $R^3$ is independently H, F, Cl, Br, I, OH, CN, $NO_2$, substituted or unsubstituted alkyl, perfluoroalkyl, substituted or unsubstituted cycloalkyl, substituted or unsubstituted alkenyl, substituted or unsubstituted cycloalkenyl, substituted or unsubstituted alkynyl, substituted or unsubstituted aryl, substituted or unsubstituted arylalkyl, substituted or unsubstituted heteroaryl, substituted or unsubstituted heteroarylalkyl, —$(CH_2)_jOR^4$, —$(CH_2)_jC(O)R^4$, —$(CH_2)_jC(NR^7)R^4$, —$(CH_2)_jC(NNR^7)R^4$, —$(CH_2)_jC(O)OR^4$, —$(CH_2)_jNR^5R^6$, —$(CH_2)_jC(O)NR^5R^6$, —$(CH_2)_jOC(O)NR^5R^6$, —$(CH_2)_jNR^7C(O)R^4$, —$(CH_2)_jNR^7C(O)OR^4$, —$(CH_2)_jNR^7C(O)NR^5R^6$, —$(CH_2)_jS(O)_mR^8$, —$(CH_2)_jNR^7S(O)_2R^8$, or —$(CH_2)_jS(O)_2NR^5R^6$.

In another aspect the disclosure provides compounds of formula I, wherein:

$R^1$ is independently substituted or unsubstituted $(C_1-C_{12})$alkyl, substituted or unsubstituted $(C_3-C_{12})$cycloalkyl, substituted or unsubstituted $(C_2-C_{12})$alkenyl, substituted or unsubstituted $(C_4-C_{12})$cycloalkenyl, or substituted or unsubstituted $(C_2-C_{12})$alkynyl, wherein $R^1$ is optionally independently substituted with 1 to 3 $R^3$ groups; and $R^3$ is independently F, Cl, Br, I, OH, CN, $NO_2$, alkyl, perfluoroalkyl, cycloalkyl, alkenyl, cycloalkenyl, alkynyl, aryl, arylalkyl, heteroaryl, heteroarylalkyl, —$(CH_2)_jOR^4$, —$(CH_2)_jC(O)R^4$, —$(CH_2)_jC(NR^7)R^4$, —$(CH_2)_jC(NNR^7)R^4$, —$(CH_2)_jC(O)OR^4$, —$(CH_2)_jNR^5R^6$, —$(CH_2)_jOC(O)NR^5R^6$, —$(CH_2)_jNR^7C(O)R^4$, —$(CH_2)_jNR^7C(O)OR^4$, —$(CH_2)_jNR^7C(O)NR^5R^6$, —$(CH_2)_jS(O)_mR^8$, —$(CH_2)_jNR^7S(O)_2R^8$, or —$(CH_2)_jS(O)_2NR^5R^6$.

In another aspect the disclosure provides compounds of formula I, wherein:

$L_1$ is independently a direct bond,

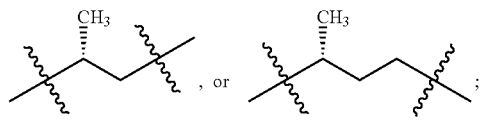

, or $L_1$ is independently a direct bond or $CH_2$; and $R^1$ is independently:

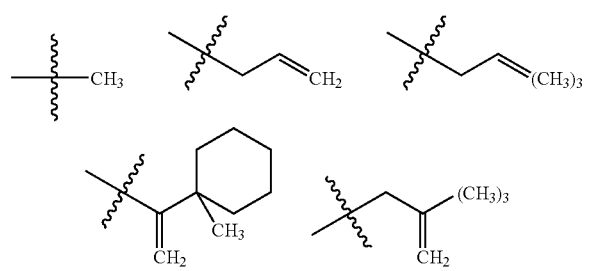

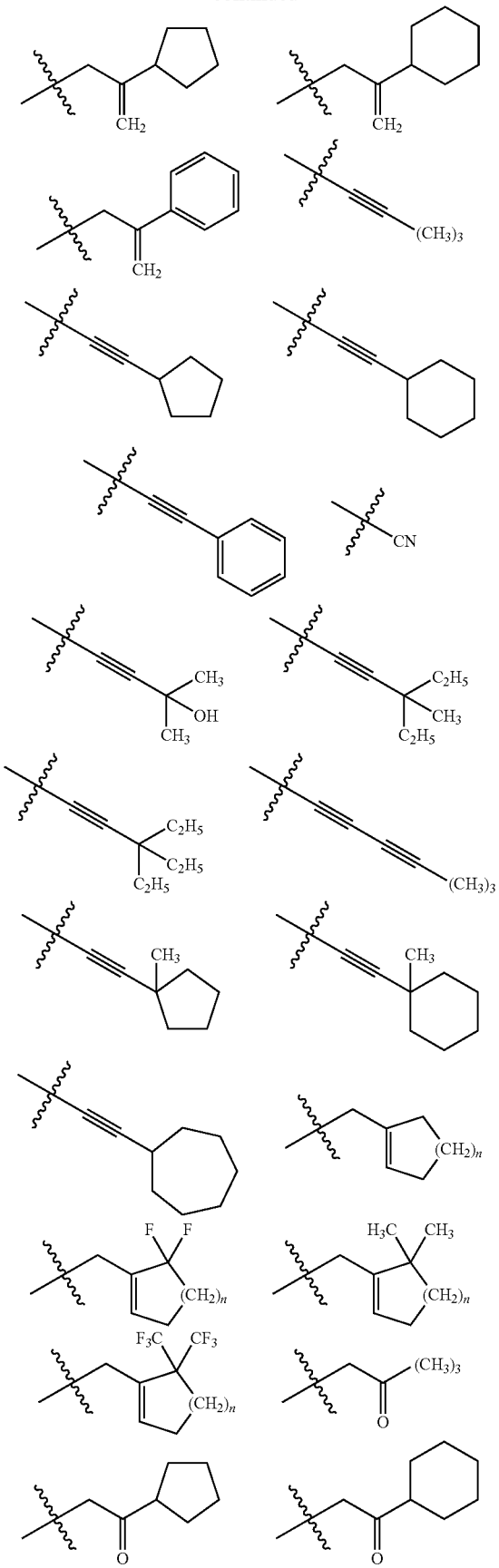

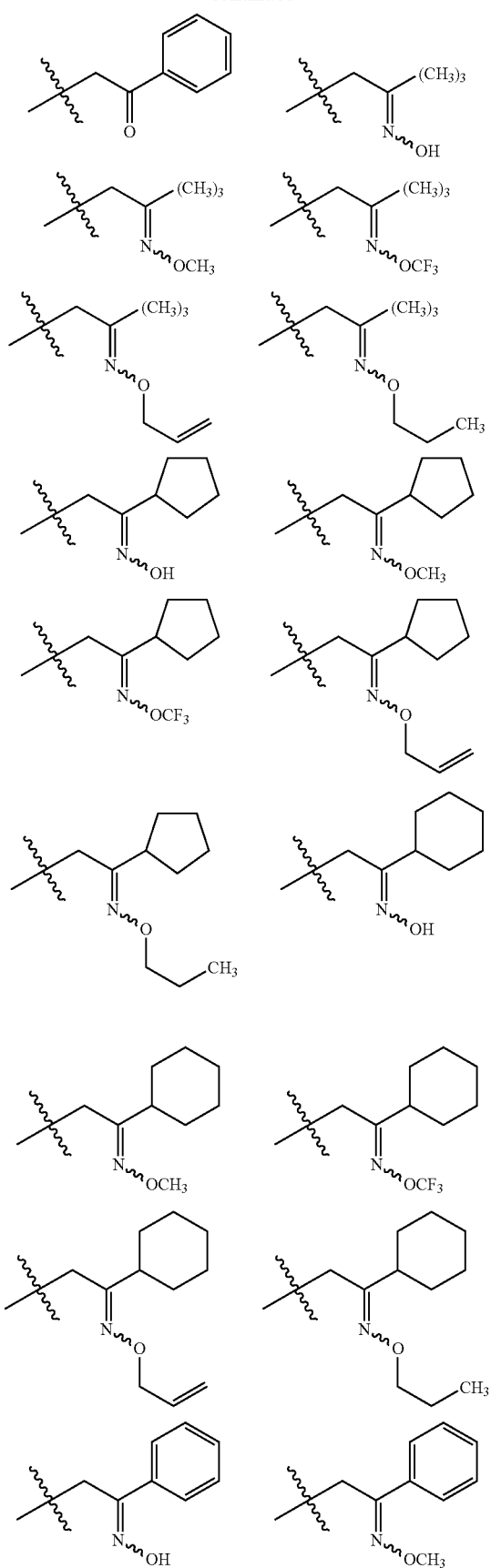
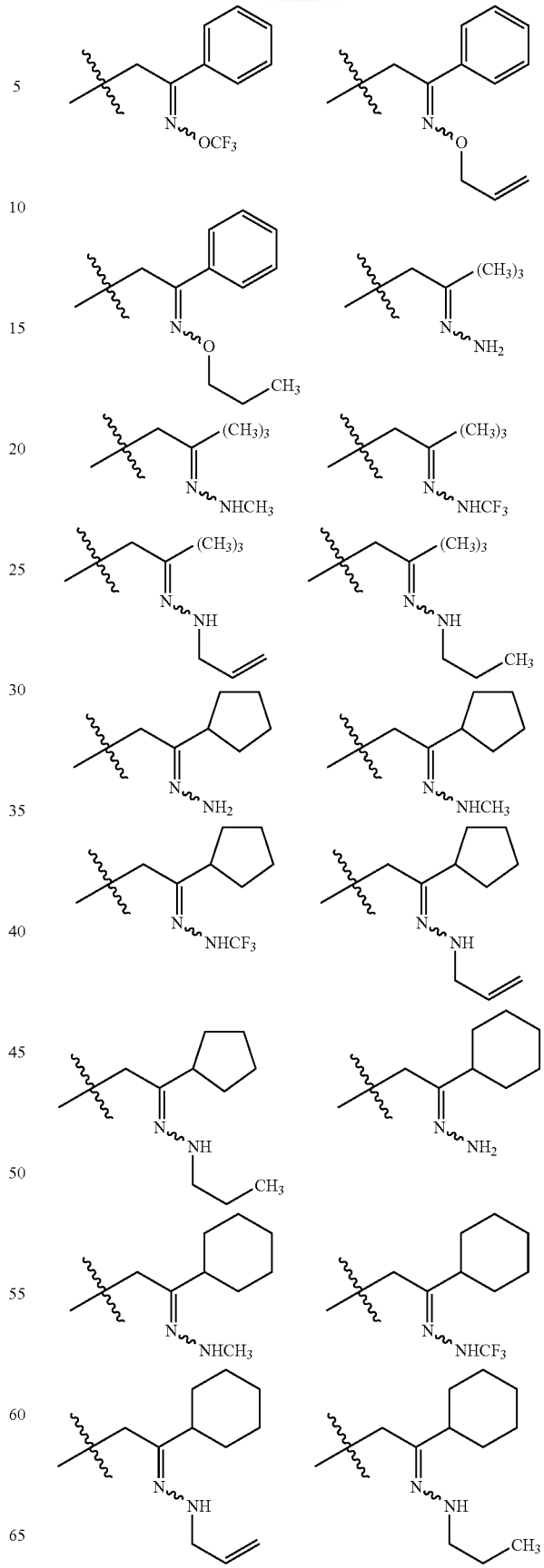

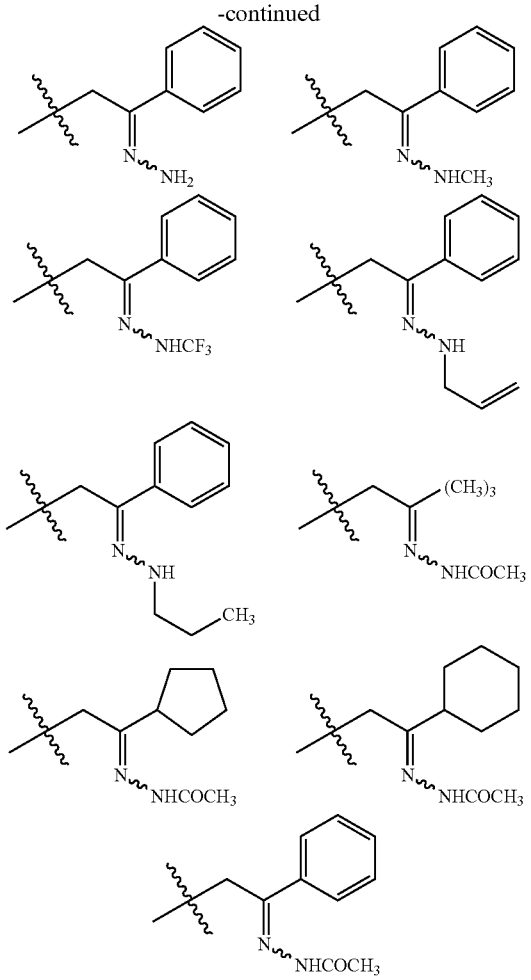
wherein n is independently an integer from 0 to 2.
In another aspect the disclosure provides compounds of formula I, wherein:
$L_1$ is independently a direct bond,
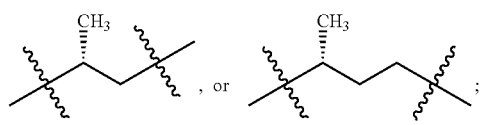, or ;
$L_1$ is independently a direct bond or $CH_2$; and
$R^1$ is independently:
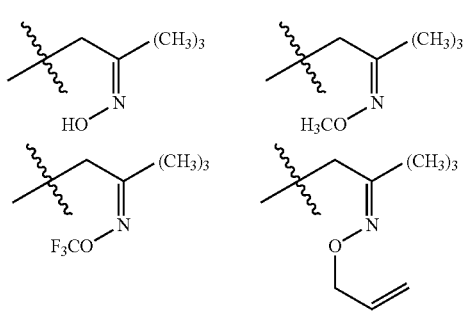
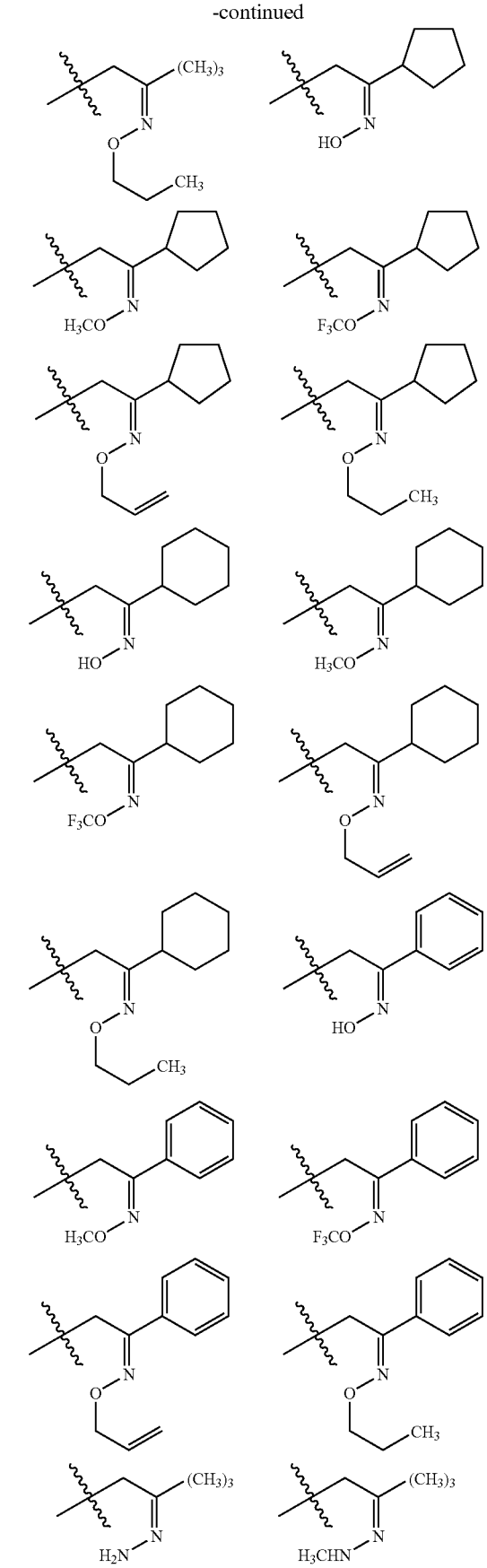

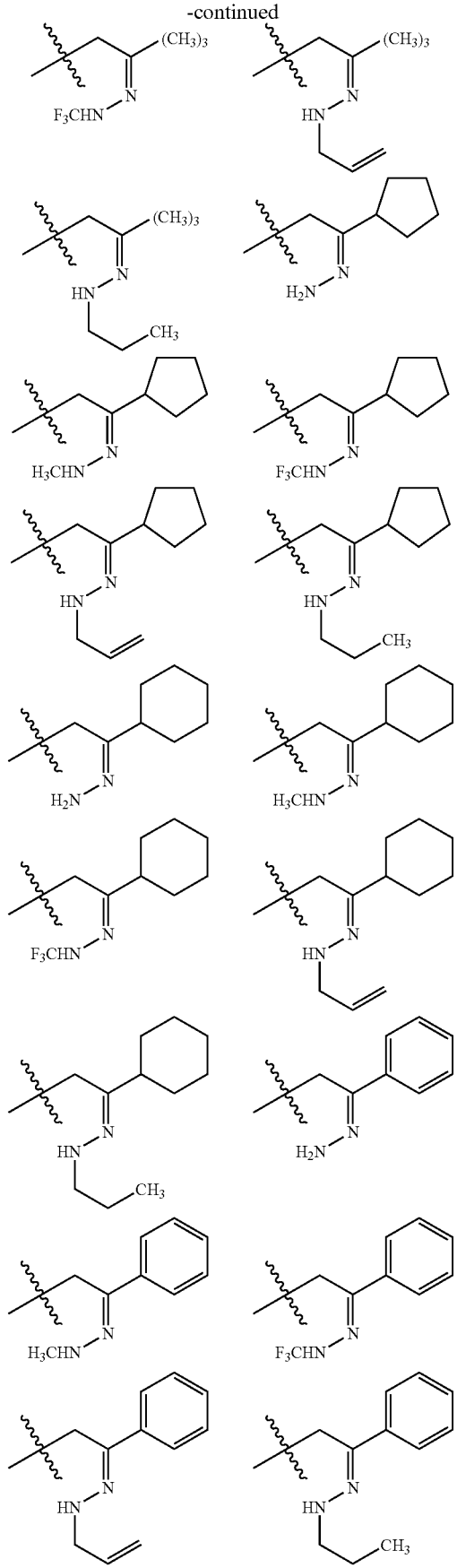
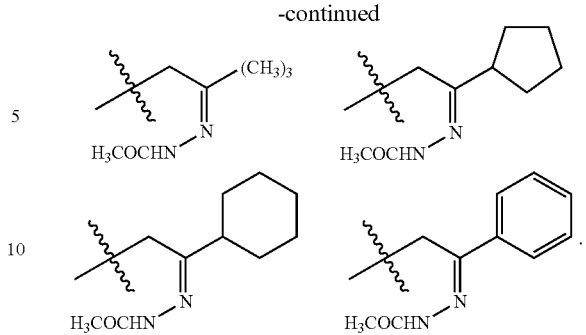
In another aspect the disclosure provides compounds of formula I, having formula II or formula III:
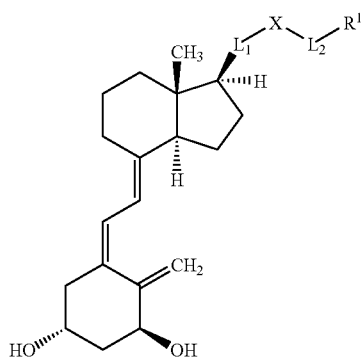
II
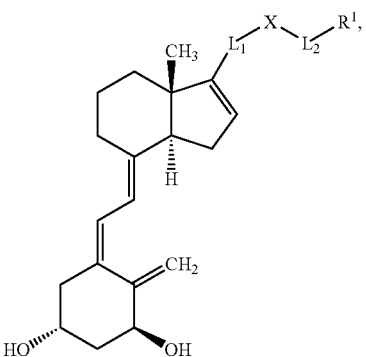
III
wherein:
L₁ is independently a direct bond,
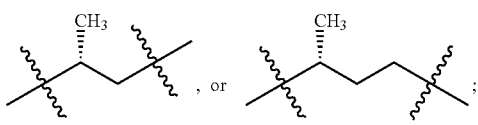
, or ;
L₁ is independently a direct bond or $CH_2$; and
R¹ is independently:
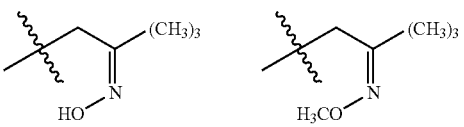

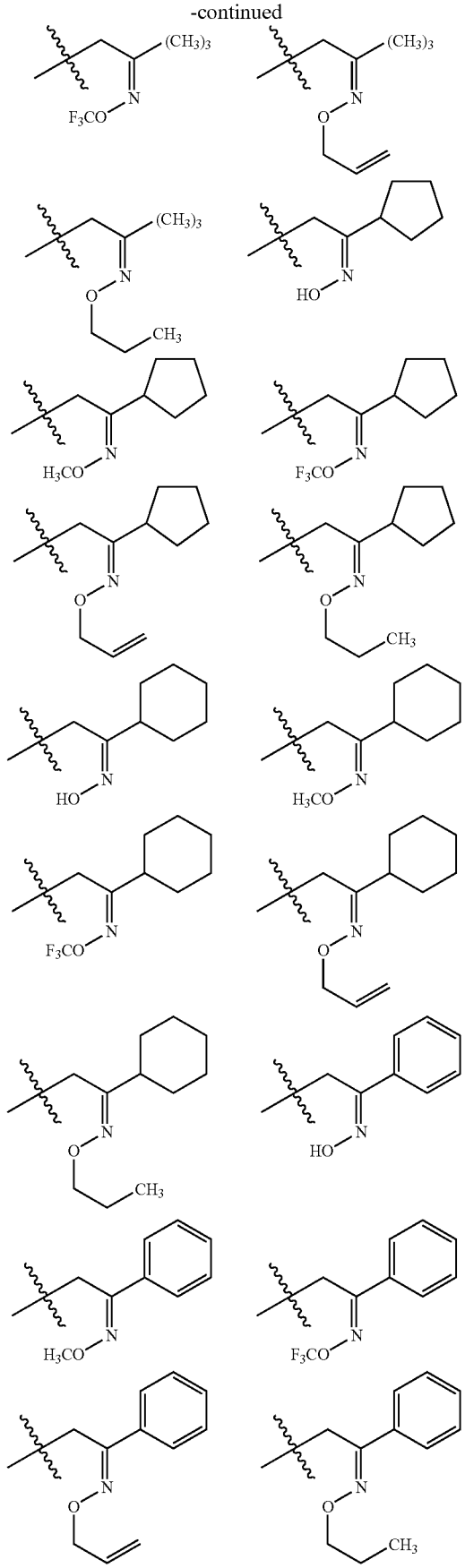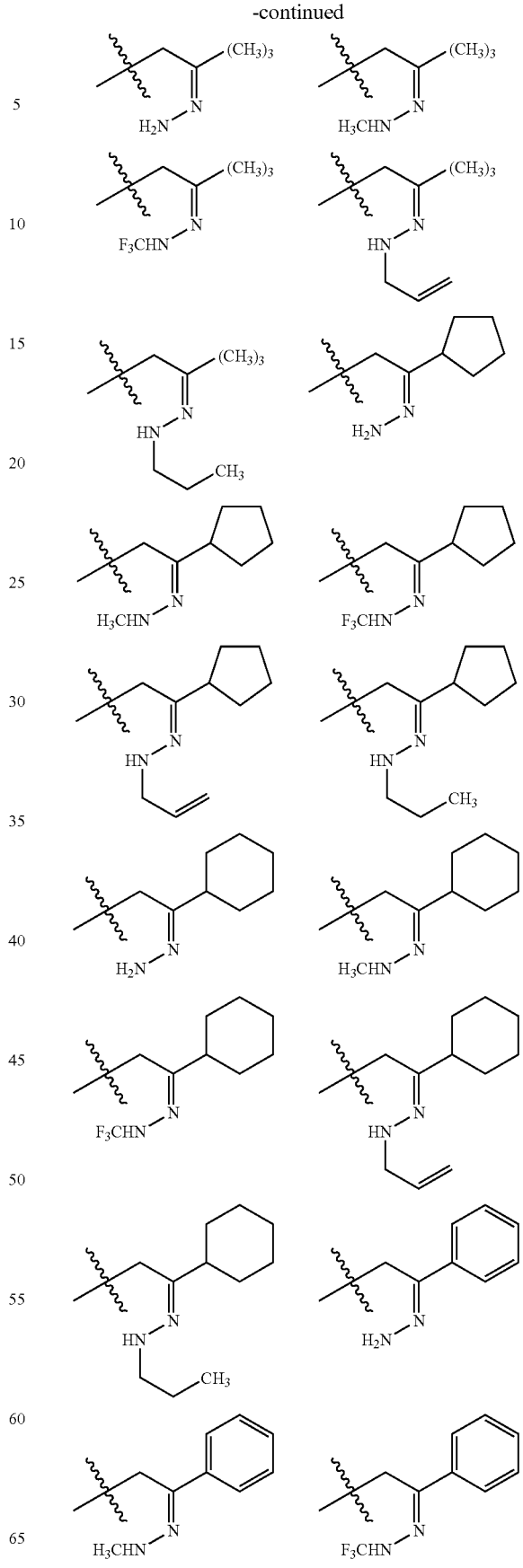

-continued

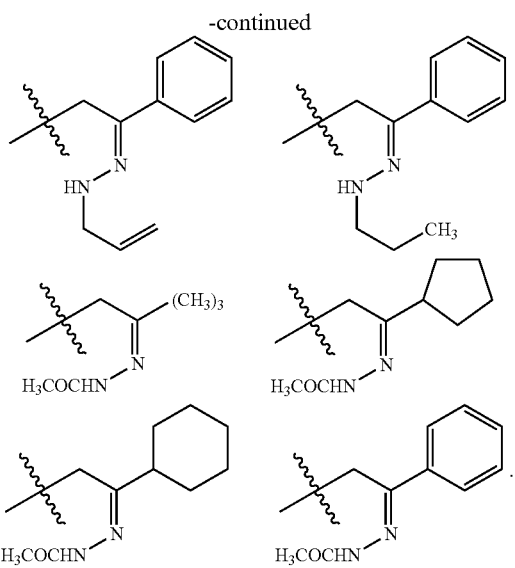

In another aspect the disclosure provides compounds of formula I, wherein:
X is independently O;
$L_1$ is independently a direct bond, or $(C_1$-$C_6)$alkyl;
$L_2$ is independently a direct bond, or $(C_1$-$C_6)$alkyl;
$R^1$ is independently substituted or unsubstituted aryl, substituted or unsubstituted arylalkyl, substituted or unsubstituted heteroaryl, or substituted or unsubstituted heteroarylalkyl; and
$R^3$ is independently H, F, Cl, Br, I, OH, CN, $NO_2$, substituted or unsubstituted alkyl, perfluoroalkyl, substituted or unsubstituted cycloalkyl, substituted or unsubstituted alkenyl, substituted or unsubstituted cycloalkenyl, substituted or unsubstituted alkynyl, substituted or unsubstituted aryl, substituted or unsubstituted arylalkyl, substituted or unsubstituted heteroaryl, substituted or unsubstituted heteroarylalkyl, —$(CH_2)_jOR^4$, —$(CH_2)_jC(O)R^4$, —$(CH_2)_jC(NR^7)R^4$, —$(CH_2)_jC(NNR^7)R^4$, —$(CH_2)_jC(O)OR^4$, —$(CH_2)_jNR^5R^6$, —$(CH_2)_jC(O)NR^5R^6$, —$(CH_2)_jOC(O)NR^5R^6$, —$(CH_2)_jNR^7C(O)R^4$, —$(CH_2)_jNR^7C(O)OR^4$, —$(CH_2)_jNR^7C(O)NR^5R^6$, —$(CH_2)_jS(O)_mR^8$, —$(CH_2)_jNR^7S(O)_2R^8$, or —$(CH_2)_jS(O)_2NR^5R^6$.

In another aspect the disclosure provides compounds of formula I, wherein:
$R^1$ is independently substituted or unsubstituted phenyl, substituted or unsubstituted naphthyl, substituted or unsubstituted furanyl, substituted or unsubstituted pyrrolyl, substituted or unsubstituted thiofuranyl, substituted or unsubstituted oxazolyl, substituted or unsubstituted isooxazolyl, substituted or unsubstituted pyrazolyl, substituted or unsubstituted imidazolyl, substituted or unsubstituted pyridinyl, substituted or unsubstituted pyridazinyl, substituted or unsubstituted pyrimidinyl, substituted or unsubstituted pyrazinyl, wherein $R^1$ is optionally independently substituted with 1 to 3 $R^3$ groups; and
$R^3$ is independently F, Cl, Br, I, OH, CN, $NO_2$, alkyl, perfluoroalkyl, cycloalkyl, alkenyl, cycloalkenyl, alkynyl, aryl, arylalkyl, heteroaryl, heteroarylalkyl, —$(CH_2)_jOR^4$, —$(CH_2)_jC(O)R^4$, —$(CH_2)_jC(NR^7)R^4$, —$(CH_2)_jC(NNR^7)R^4$, —$(CH_2)_jC(O)OR^4$, —$(CH_2)_jNR^5R^6$, —$(CH_2)_jC(O)NR^5R^6$, —$(CH_2)_jOC(O)NR^5R^6$, —$(CH_2)_jNR^7C(O)R^4$, —$(CH_2)_jNR^7C(O)OR^4$, —$(CH_2)_jNR^7C(O)NR^5R^6$, —$(CH_2)_jS(O)_mR^8$, —$(CH_2)_jNR^7S(O)_2R^8$, or —$(CH_2)_jS(O)_2NR^5R^6$.

In another aspect the disclosure provides compounds of formula I, wherein:
$L_1$ is independently a direct bond,

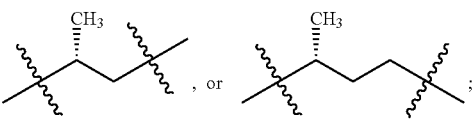

$L_1$ is independently a direct bond or $CH_2$; and
$R^1$ is independently:

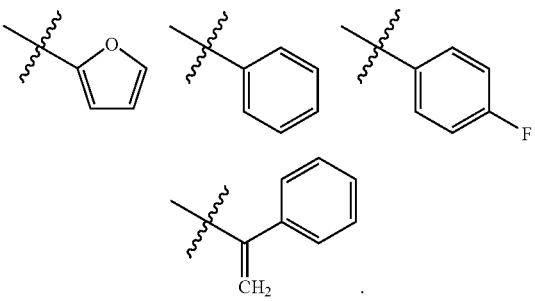

In another aspect the disclosure provides compounds of formula I, having formula II or formula III:

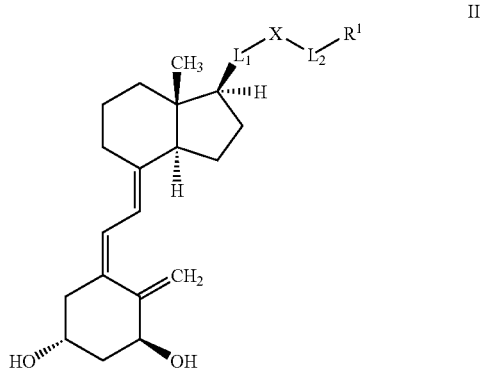

II

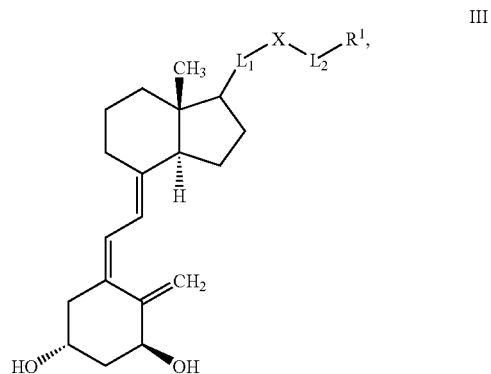

III wherein:

$L_1$ is independently a direct bond,

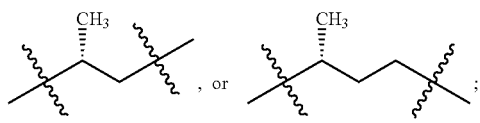

, or $L_1$ is independently a direct bond or $CH_2$; and
$R^1$ is independently:

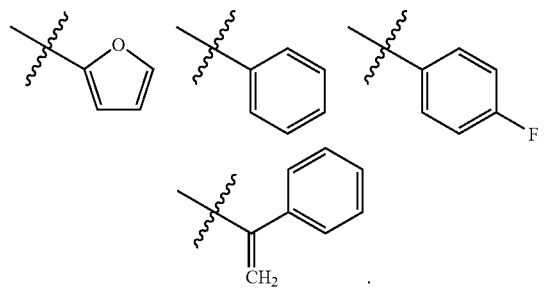

In another aspect the disclosure provides compounds of formula I, wherein the compound of formula I has formula IV:

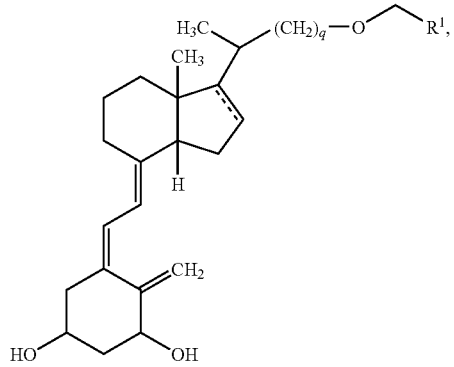

IV wherein:

q is independently an integer from 0 to 2;

$R^1$ is independently substituted or unsubstituted alkyl, substituted or unsubstituted cycloalkyl, substituted or unsubstituted alkenyl, substituted or unsubstituted cycloalkenyl, or substituted or unsubstituted alkynyl; and $R^3$ is independently H, F, Cl, Br, I, OH, CN, $NO_2$, substituted or unsubstituted alkyl, perfluoroalkyl, substituted or unsubstituted cycloalkyl, substituted or unsubstituted alkenyl, substituted or unsubstituted cycloalkenyl, substituted or unsubstituted alkynyl, substituted or unsubstituted aryl, substituted or unsubstituted arylalkyl, substituted or unsubstituted heteroaryl, substituted or unsubstituted heteroarylalkyl, $-(CH_2)_jOR^4$, $-(CH_2)_jC(O)R^4$, $-(CH_2)_jC(NR^7)R^4$, $-(CH_2)_jC(NNR^7)R^4$, $-(CH_2)_jC(O)OR^4$, $-(CH_2)_jNR^5R^6$, $-(CH_2)_jC(O)NR^5R^6$, $-(CH_2)_jOC(O)NR^5R^6$, $-(CH_2)_jNR^7C(O)R^4$, $-(CH_2)_jNR^7C(O)OR^4$, $-(CH_2)_jNR^7C(O)NR^5R^6$, $-(CH_2)_jS(O)_mR^8$, $-(CH_2)_jNR^7S(O)_2R^8$, or $-(CH_2)_jS(O)_2NR^5R^6$.

In another aspect the disclosure provides compounds of formula IV, wherein:

$R^1$ is independently substituted or unsubstituted ($C_1$-$C_{12}$) alkyl, substituted or unsubstituted ($C_3$-$C_{12}$)cycloalkyl, substituted or unsubstituted ($C_2$-$C_{12}$)alkenyl, substituted or unsubstituted ($C_4$-$C_{12}$)cycloalkenyl, or substituted or unsubstituted ($C_2$-$C_{12}$)alkynyl, wherein $R^1$ is optionally independently substituted with 1 to 3 $R^3$ groups; and $R^3$ is independently F, Cl, Br, I, OH, CN, $NO_2$, alkyl, perfluoroalkyl, cycloalkyl, alkenyl, cycloalkenyl, alkynyl, aryl, arylalkyl, heteroaryl, heteroarylalkyl, $-(CH_2)_jOR^4$, $-(CH_2)_jC(O)R^4$, $-(CH_2)_jC(NR^7)R^4$, $-(CH_2)_jC(NNR^7)R^4$, $-(CH_2)_jC(O)OR^4$, $-(CH_2)_jNR^5R^6$, $-(CH_2)_jC(O)NR^5R^6$, $-(CH_2)_jOC(O)NR^5R^6$, $-(CH_2)_jNR^7C(O)R^4$, $-(CH_2)_jNR^7C(O)OR^4$, $-(CH_2)_jNR^7C(O)NR^5R^6$, $-(CH_2)_jS(O)_mR^8$, $-(CH_2)_jNR^7S(O)_2R^8$, or $-(CH_2)_jS(O)_2NR^5R^6$.

In another aspect the disclosure provides compounds of formula IV, wherein:

$R^1$ is independently:

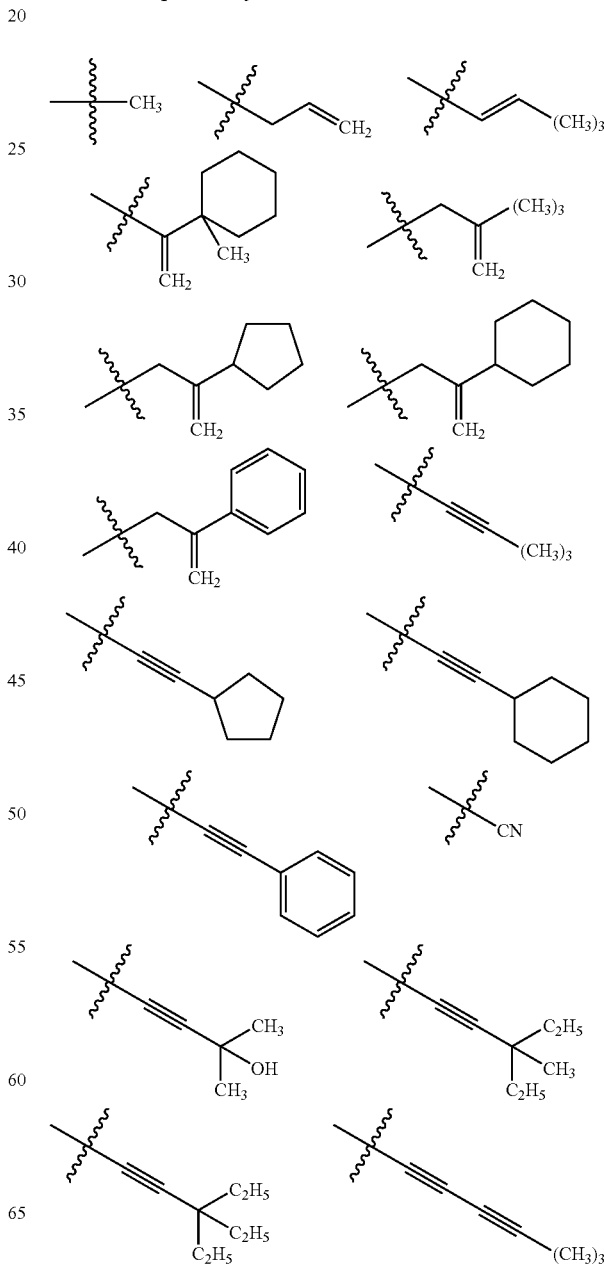

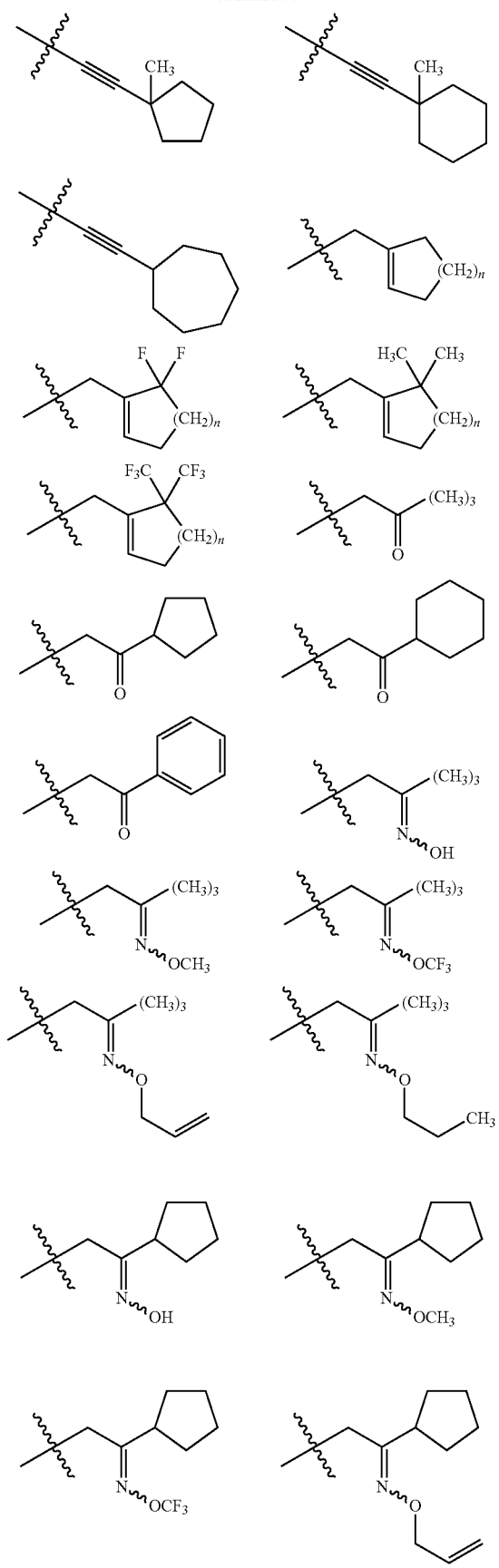
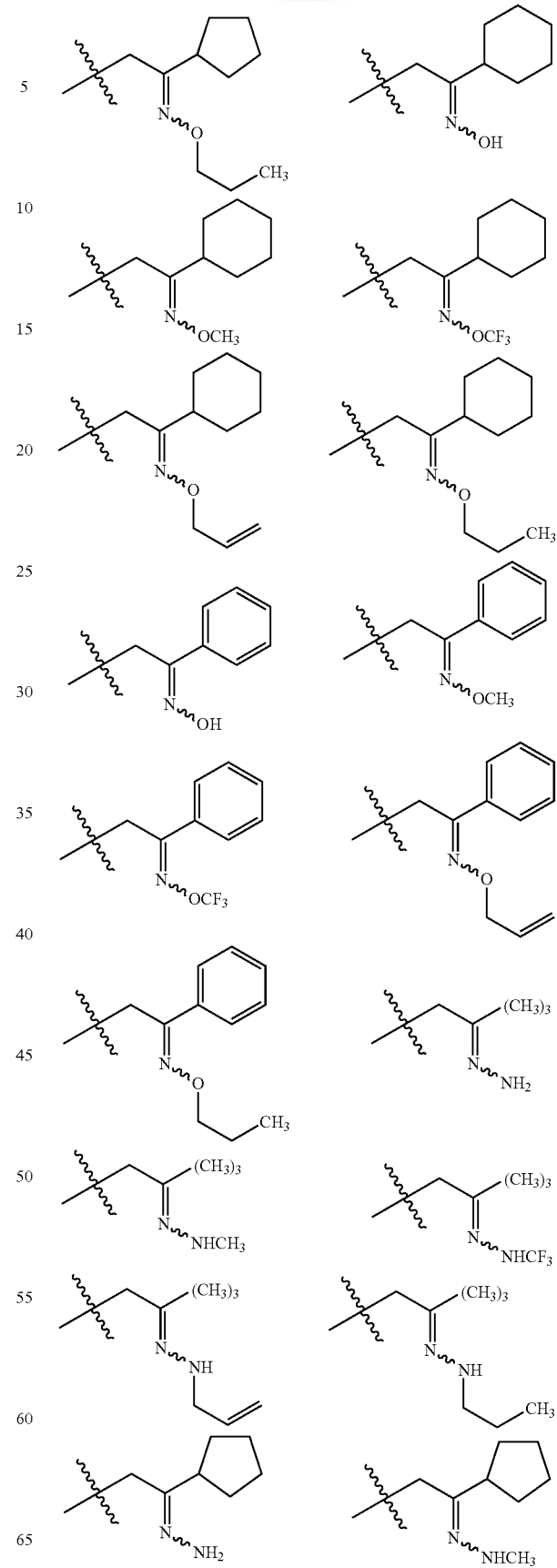

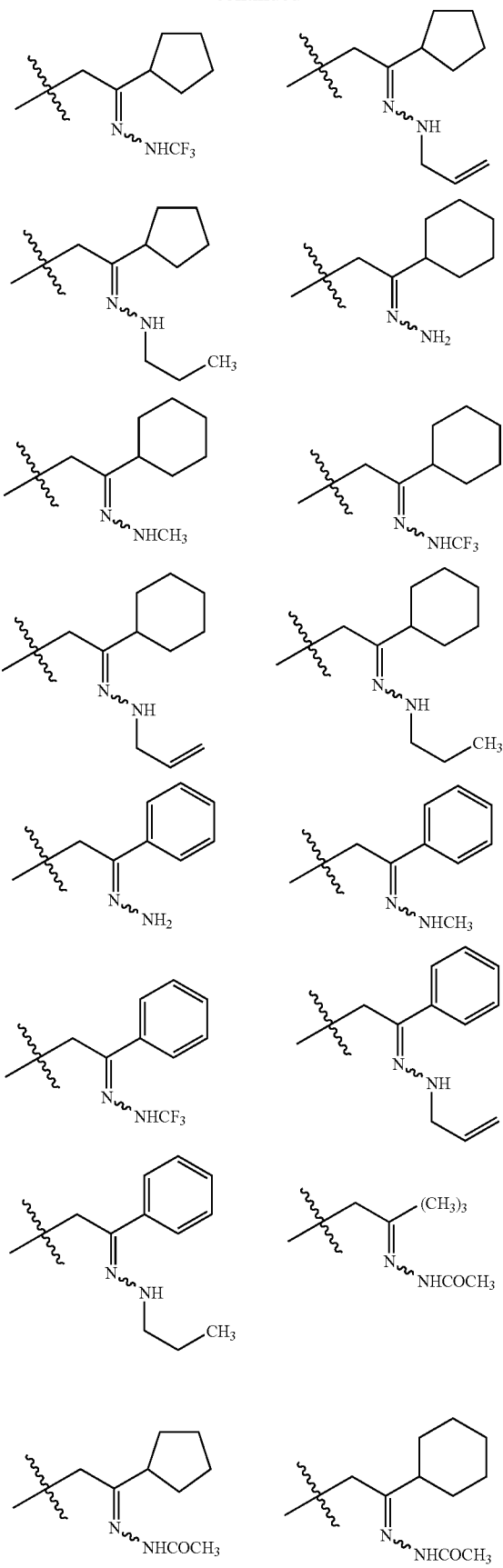
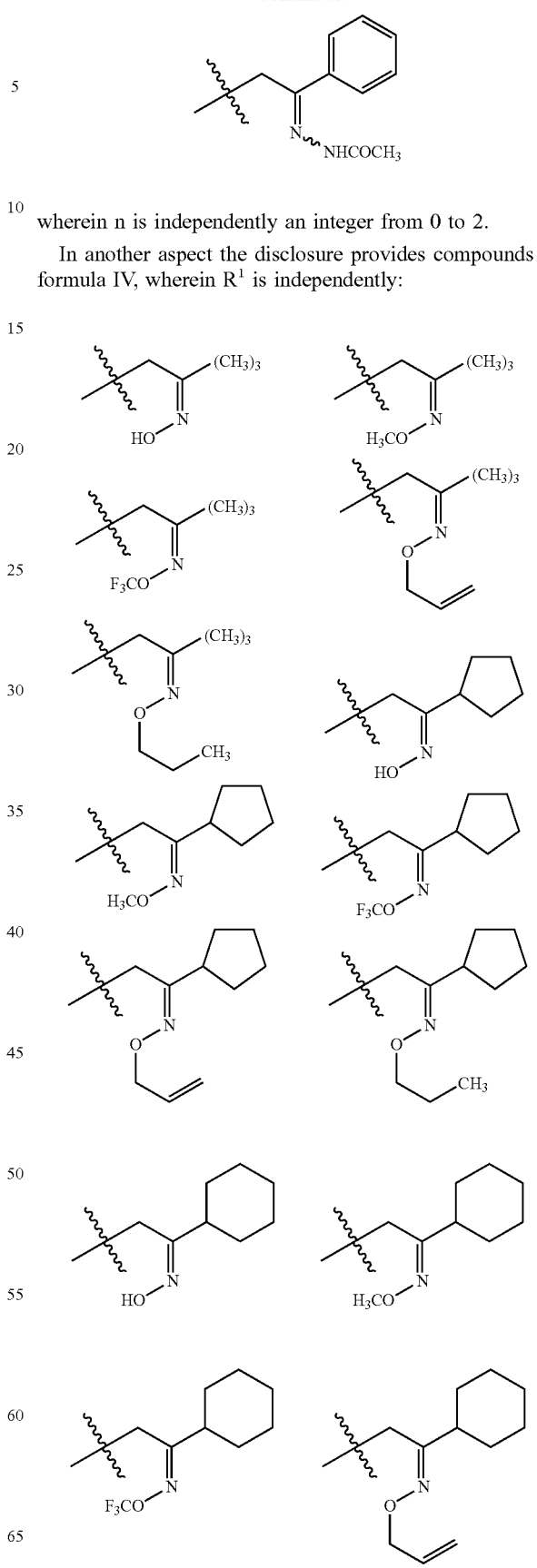
wherein n is independently an integer from 0 to 2.
In another aspect the disclosure provides compounds of formula IV, wherein R¹ is independently:

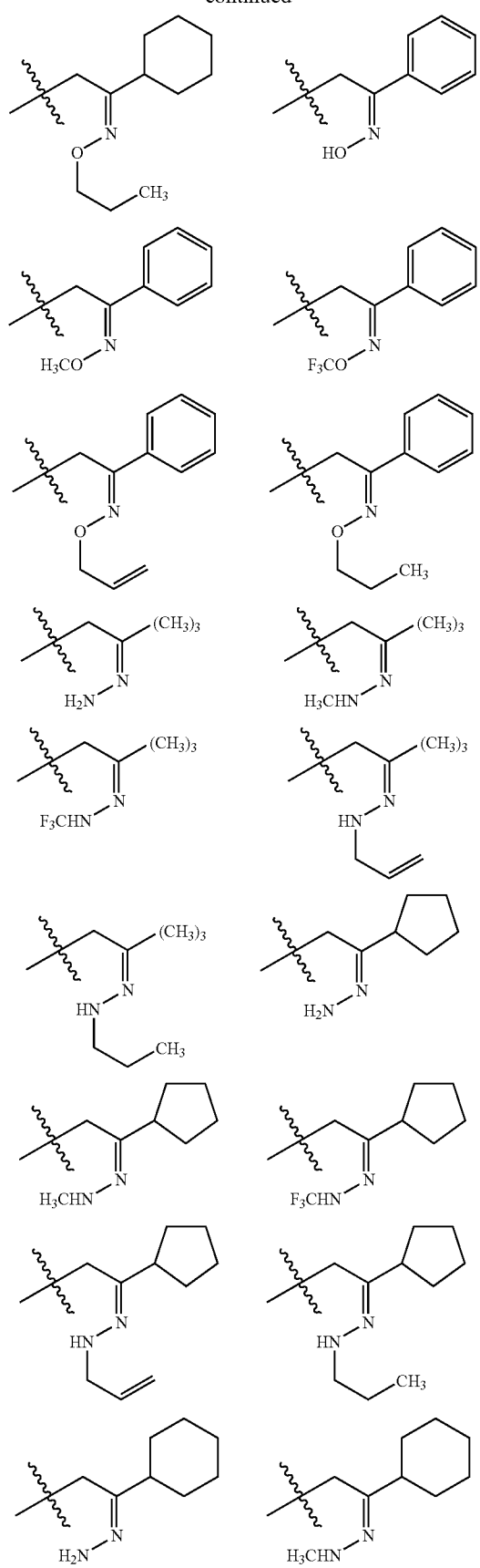
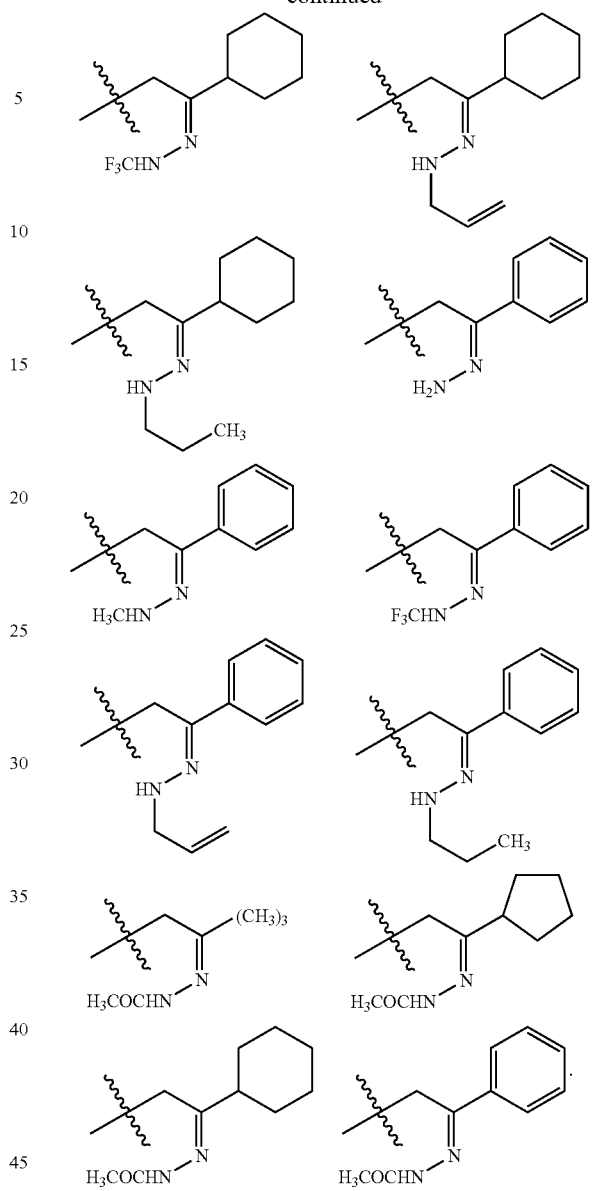
In another aspect the disclosure provides compounds of formula IV, having formula V or formula VI:
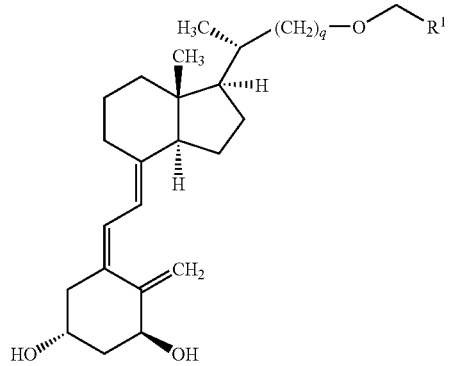

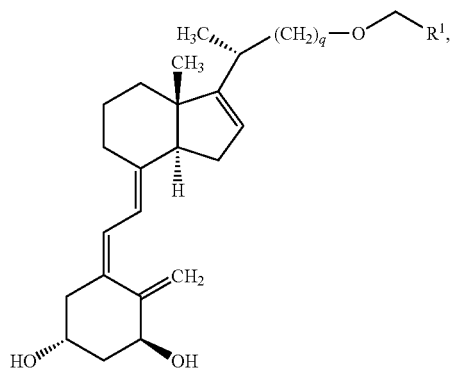
wherein:
R[1] is independently:
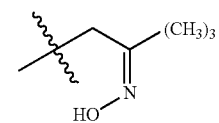 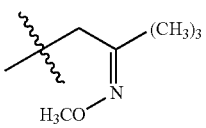
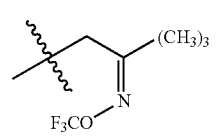 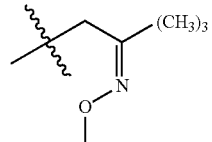
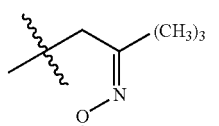 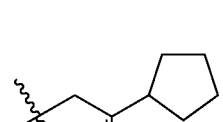
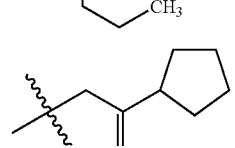 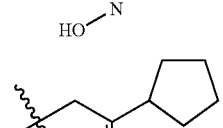
 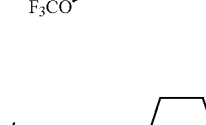
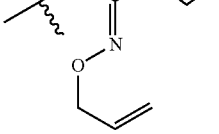 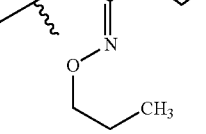
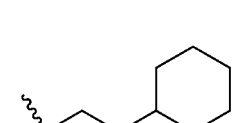 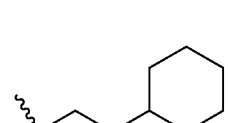
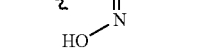 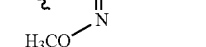
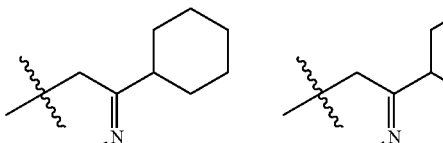 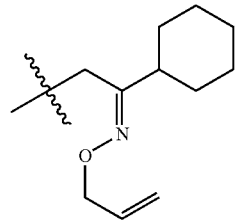
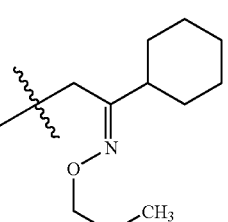 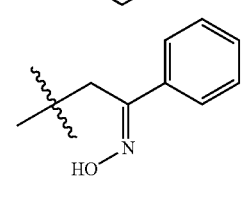
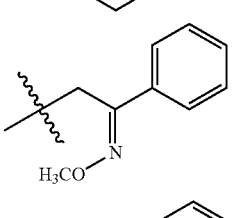 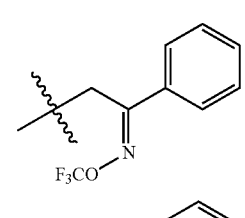
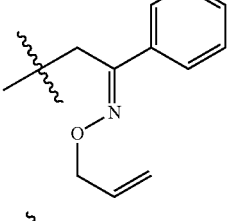 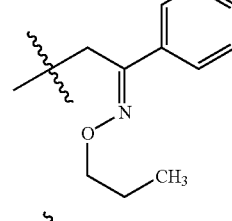
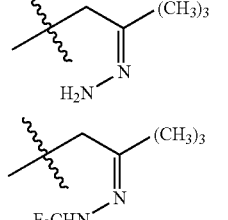 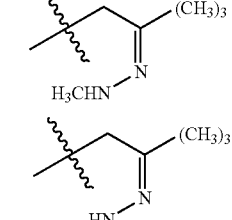
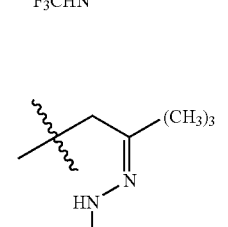 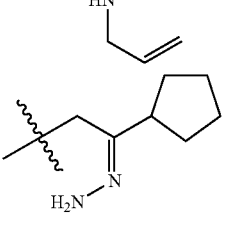
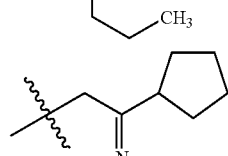 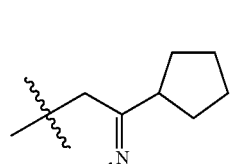
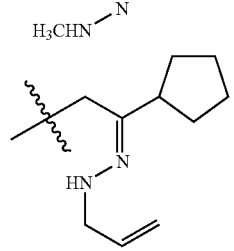 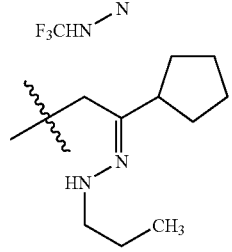

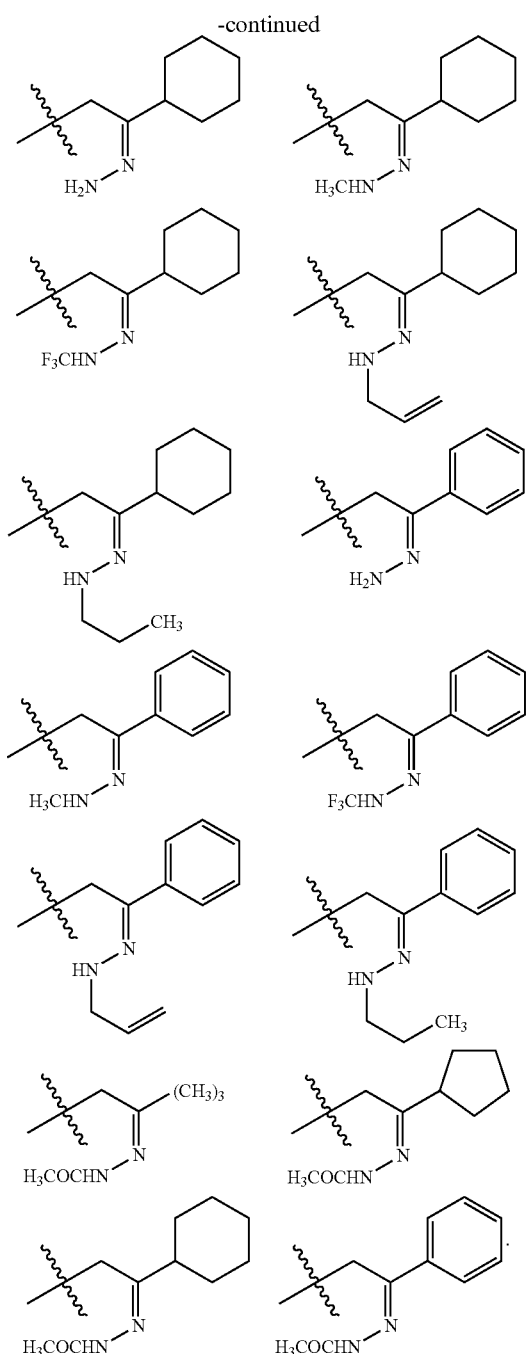

In another aspect the disclosure provides compounds of formula IV, wherein:

R¹ is independently substituted or unsubstituted aryl, substituted or unsubstituted arylalkyl, substituted or unsubstituted heteroaryl, or substituted or unsubstituted heteroarylalkyl; and R³ is independently H, F, Cl, Br, I, OH, CN, NO$_2$, substituted or unsubstituted alkyl, perfluoroalkyl, substituted or unsubstituted cycloalkyl, substituted or unsubstituted alkenyl, substituted or unsubstituted cycloalkenyl, substituted or unsubstituted alkynyl, substituted or unsubstituted aryl, substituted or unsubstituted arylalkyl, substituted or unsubstituted heteroaryl, substituted or unsubstituted heteroarylalkyl, —(CH$_2$)$_j$OR⁴, —(CH$_2$)$_j$C(O)R⁴, —(CH$_2$)$_j$C(NR⁷)R⁴, —(CH$_2$)$_j$C(NNR⁷)R⁴, —(CH$_2$)$_j$C(O)OR⁴, —(CH$_2$)$_j$NR⁵R⁶, —(CH$_2$)$_j$C(O)NR⁵R⁶, —(CH$_2$)$_j$OC(O)NR⁵R⁶, —(CH$_2$)$_j$NR⁷C(O)R⁴, —(CH$_2$)$_j$NR⁷C(O)OR⁴, —(CH$_2$)$_j$NR⁷C(O)NR⁵R⁶, —(CH$_2$)$_j$S(O)$_m$R⁸, —(CH$_2$)$_j$NR⁷S(O)$_2$R⁸, or —(CH$_2$)$_j$S(O)$_2$NR⁵R⁶.

In another aspect the disclosure provides compounds of formula IV, wherein:

R¹ is independently substituted or unsubstituted phenyl, substituted or unsubstituted naphthyl, substituted or unsubstituted furanyl, substituted or unsubstituted pyrrolyl, substituted or unsubstituted thiofuranyl, substituted or unsubstituted oxazolyl, substituted or unsubstituted isooxazolyl, substituted or unsubstituted pyrazolyl, substituted or unsubstituted imidazolyl, substituted or unsubstituted pyridinyl, substituted or unsubstituted pyridazinyl, substituted or unsubstituted pyrimidinyl, substituted or unsubstituted pyrazinyl, wherein R¹ is optionally independently substituted with 1 to 3 R³ groups; and R³ is independently F, Cl, Br, I, OH, CN, NO$_2$, alkyl, perfluoroalkyl, cycloalkyl, alkenyl, cycloalkenyl, alkynyl, aryl, arylalkyl, heteroaryl, heteroarylalkyl, —(CH$_2$)$_j$OR⁴, —(CH$_2$)$_j$C(O)R⁴, —(CH$_2$)$_j$C(NR⁷)R⁴, —(CH$_2$)$_j$C(NNR⁷)R⁴, —(CH$_2$)$_j$C(O)OR⁴, —(CH$_2$)$_j$NR⁵R⁶, —(CH$_2$)$_j$C(O)NR⁵R⁶, —(CH$_2$)$_j$OC(O)NR⁵R⁶, —(CH$_2$)$_j$NR⁷C(O)R⁴, —(CH$_2$)$_j$NR⁷C(O)OR⁴, —(CH$_2$)$_j$NR⁷C(O)NR⁵R⁶, —(CH$_2$)$_j$S(O)$_m$R⁸, —(CH$_2$)$_j$NR⁷S(O)$_2$R⁸, or —(CH$_2$)$_j$S(O)$_2$NR⁵R⁶.

In another aspect the disclosure provides compounds of formula IV, wherein:

R¹ is independently:

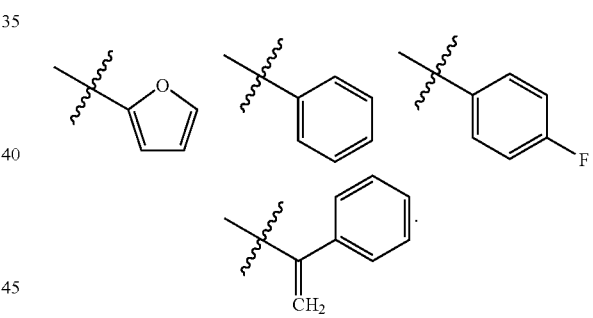

In another aspect the disclosure provides compounds of formula IV, having formula V or formula VI:

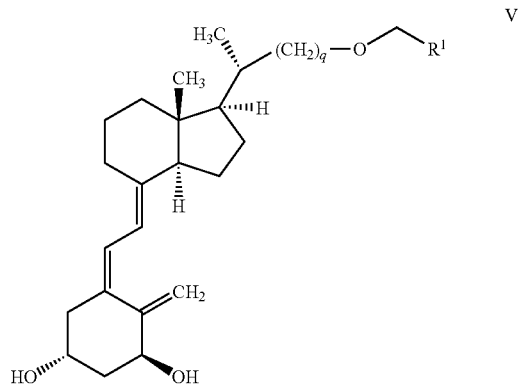

-continued

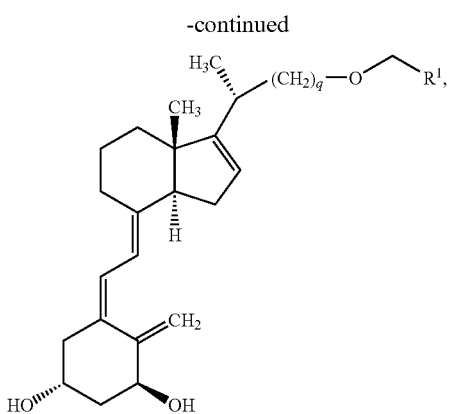

wherein:

R[1] is independently:

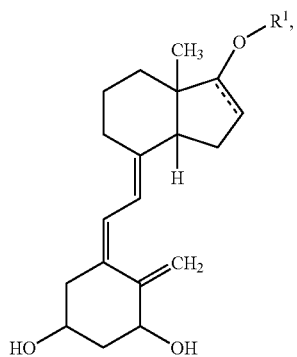

In another aspect the disclosure provides compounds having formula I, wherein the compound of formula I has formula VII:

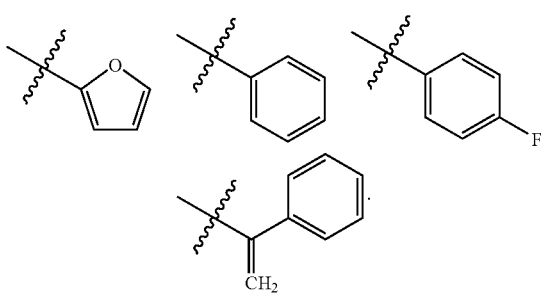

wherein:

R[1] is independently substituted or unsubstituted alkyl, substituted or unsubstituted cycloalkyl, substituted or unsubstituted alkenyl, substituted or unsubstituted cycloalkenyl, or substituted or unsubstituted alkynyl; and R[3] is independently H, F, Cl, Br, I, OH, CN, $NO_2$, substituted or unsubstituted alkyl, perfluoroalkyl, substituted or unsubstituted cycloalkyl, substituted or unsubstituted alkenyl, substituted or unsubstituted cycloalkenyl, substituted or unsubstituted alkynyl, substituted or unsubstituted aryl, substituted or unsubstituted arylalkyl, substituted or unsubstituted heteroaryl, substituted or unsubstituted heteroarylalkyl, $-(CH_2)_jOR^4$, $-(CH_2)_jC(O)R^4$, $-(CH_2)_jC(NR^7)R^4$, $-(CH_2)_jC(NNR^7)R^4$, $-(CH_2)_jC(O)OR^4$, $-(CH_2)_jNR^5R^6$, $-(CH_2)_jC(O)NR^5R^6$, $-(CH_2)_jOC(O)NR^5R^6$, $-(CH_2)_jNR^7C(O)R^4$, $-(CH_2)_jNR^7C(O)OR^4$, $-(CH_2)_jNR^7C(O)NR^5R^6$, $-(CH_2)_jS(O)_mR^8$, $-(CH_2)_jNR^7S(O)_2R^8$, or $-(CH_2)_jS(O)_2NR^5R^6$.

In another aspect the disclosure provides compounds of formula VII, wherein:

R[1] is independently substituted or unsubstituted ($C_1$-$C_{12}$)alkyl, substituted or unsubstituted ($C_3$-$C_{12}$)cycloalkyl, substituted or unsubstituted ($C_2$-$C_{12}$)alkenyl, substituted or unsubstituted ($C_4$-$C_{12}$)cycloalkenyl, or substituted or unsubstituted ($C_2$-$C_{12}$)alkynyl, wherein R[1] is optionally independently substituted with 1 to 3 R[3] groups; and R[3] is independently F, Cl, Br, I, OH, CN, $NO_2$, alkyl, perfluoroalkyl, cycloalkyl, alkenyl, cycloalkenyl, alkynyl, aryl, arylalkyl, heteroaryl, heteroarylalkyl, $-(CH_2)_jOR^4$, $-(CH_2)_jC(O)R^4$, $-(CH_2)_jC(NR^7)R^4$, $-(CH_2)_jC(NNR^7)R^4$, $-(CH_2)_jC(O)OR^4$, $-(CH_2)_jNR^5R^6$, $-(CH_2)_jC(O)NR^5R^6$, $-(CH_2)_jOC(O)NR^5R^6$, $-(CH_2)_jNR^7C(O)R^4$, $-(CH_2)_jNR^7C(O)OR^4$, $-(CH_2)_jNR^7C(O)NR^5R^6$, $-(CH_2)_jS(O)_mR^8$, $-(CH_2)_jNR^7S(O)_2R^8$, or $-(CH_2)_jS(O)_2NR^5R^6$.

In another aspect the disclosure provides compounds of formula VII, wherein:

R[1] is independently:

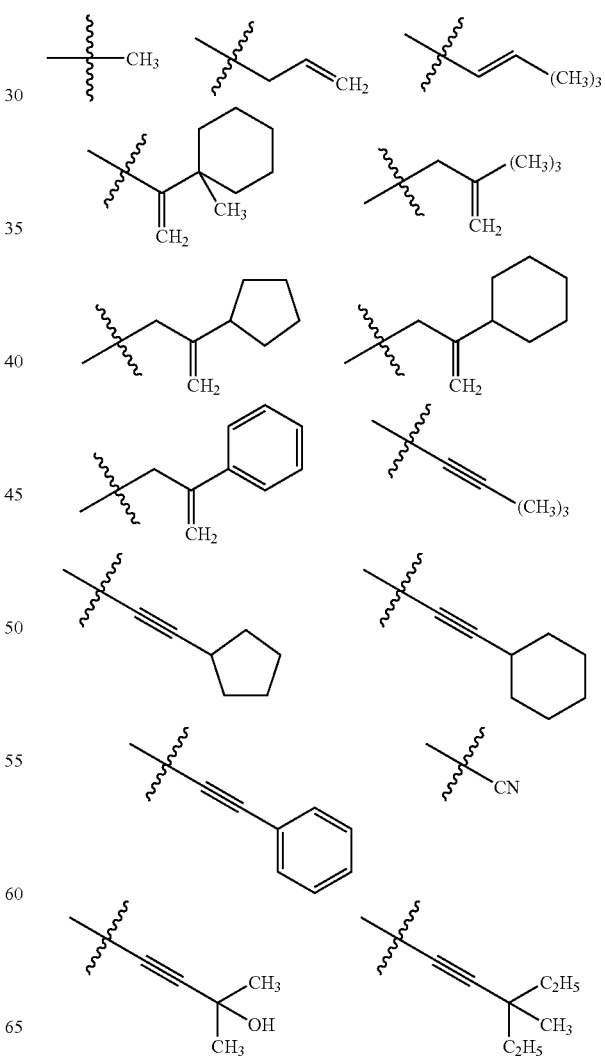

-continued
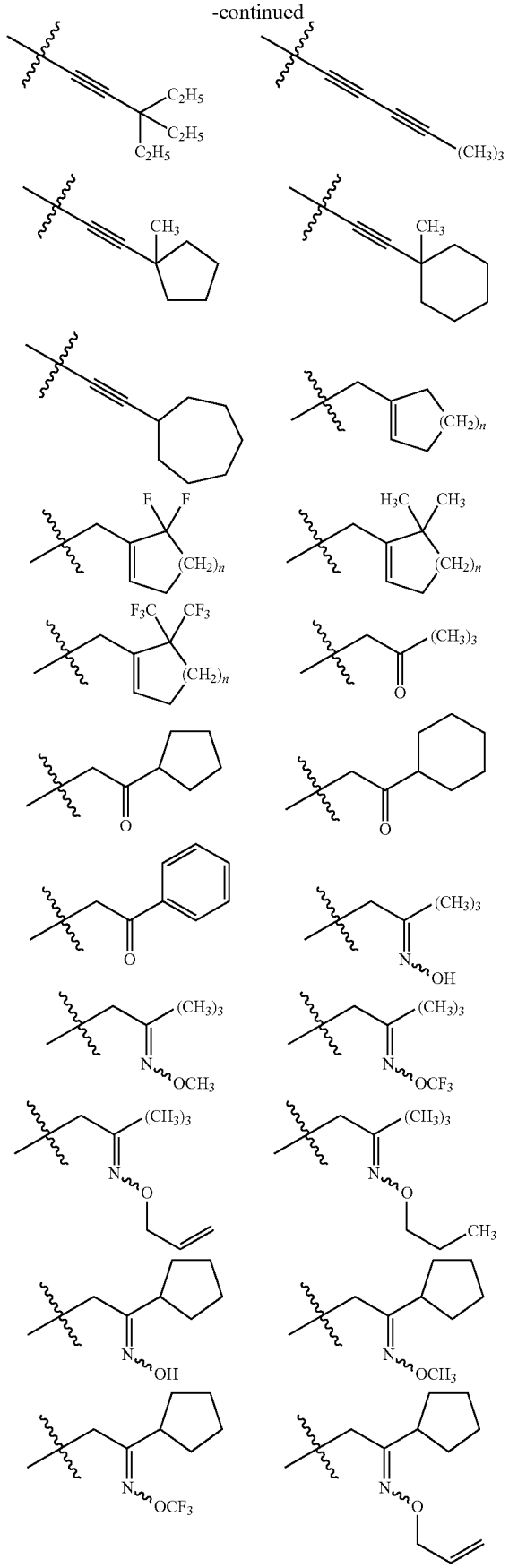
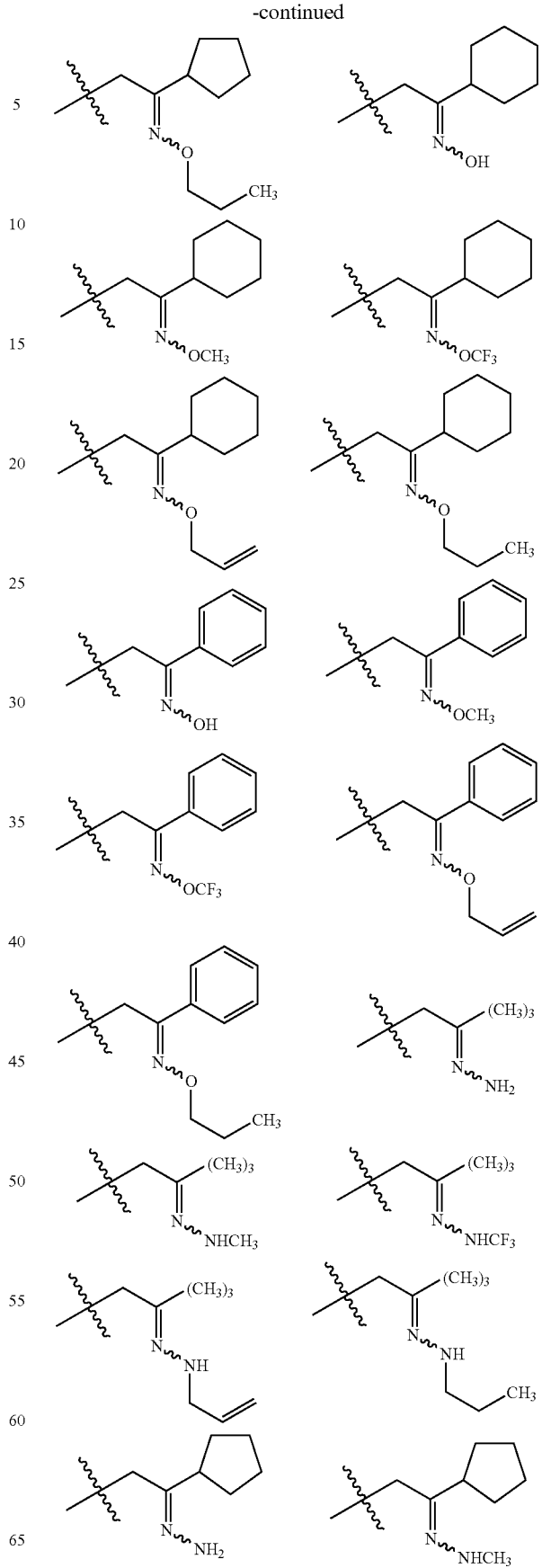

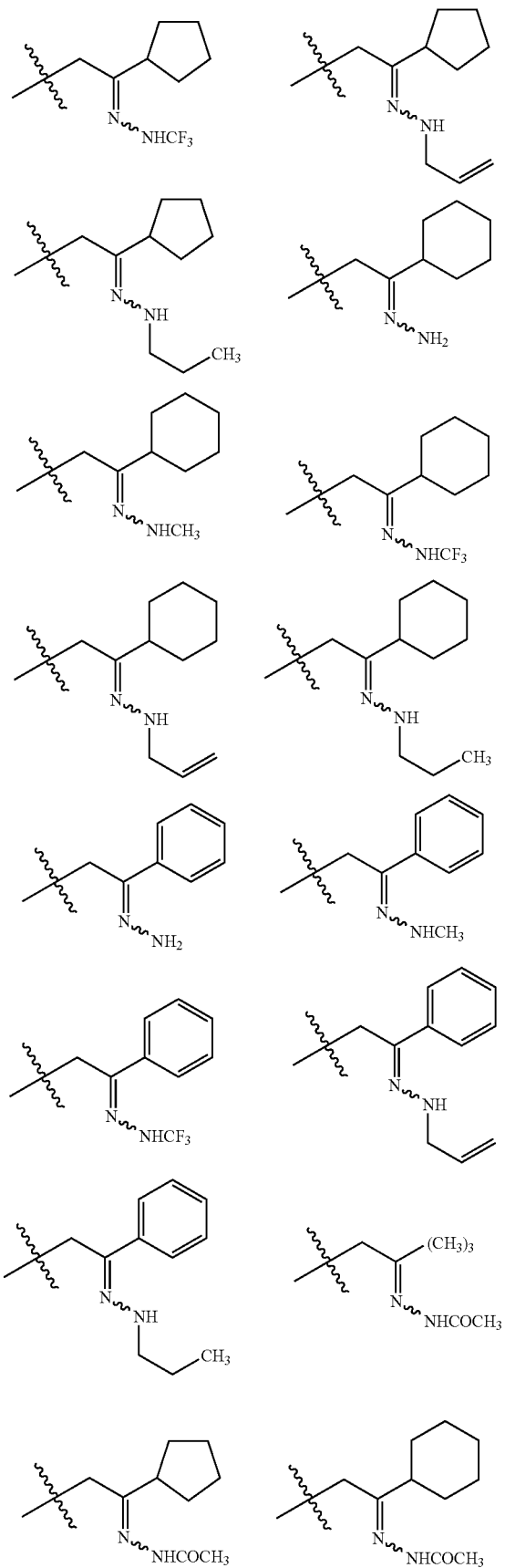
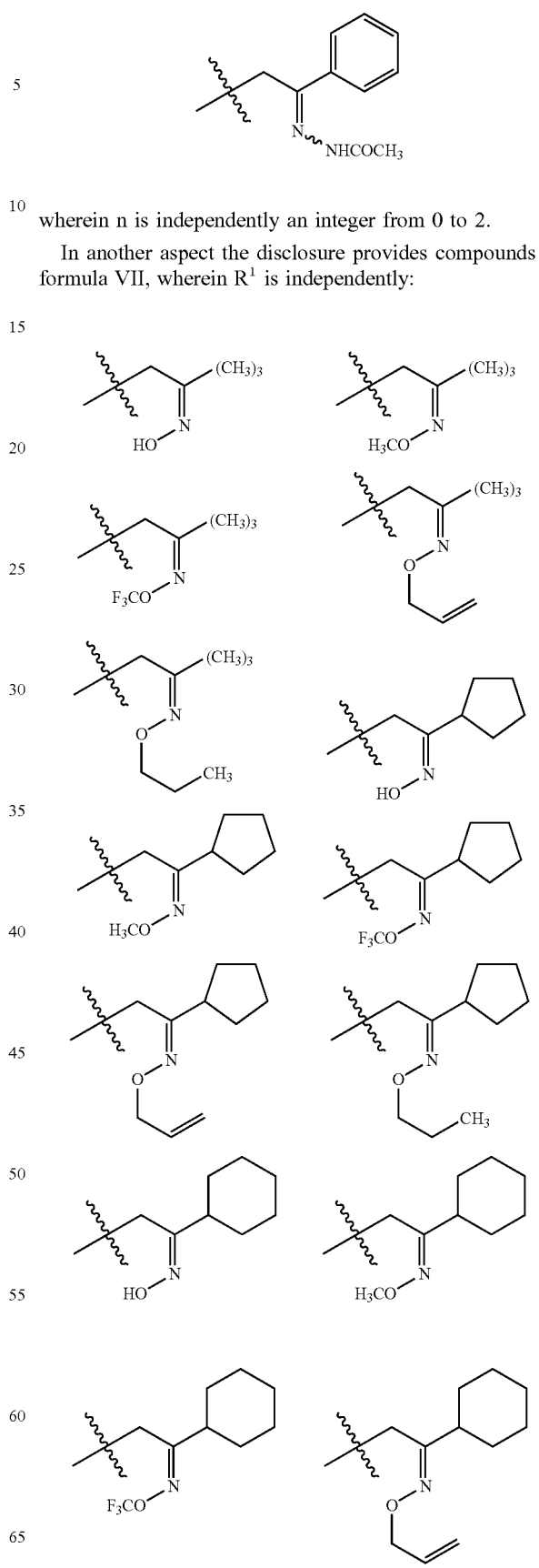
wherein n is independently an integer from 0 to 2.
In another aspect the disclosure provides compounds of formula VII, wherein $R^1$ is independently:

-continued
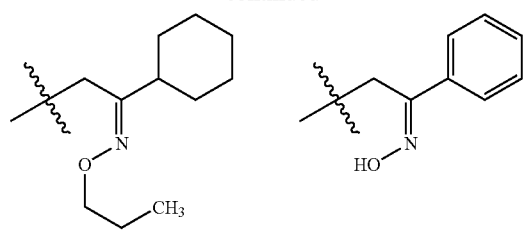
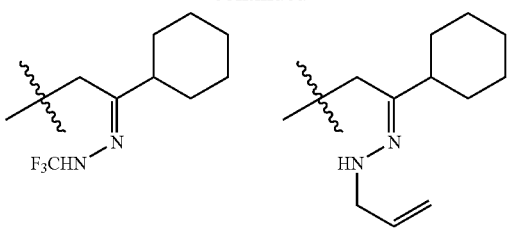
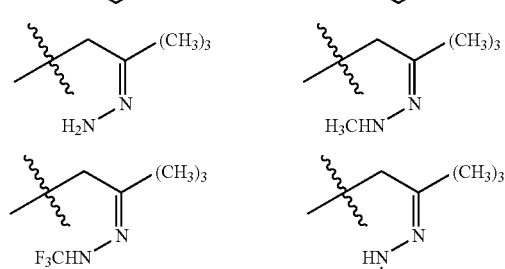
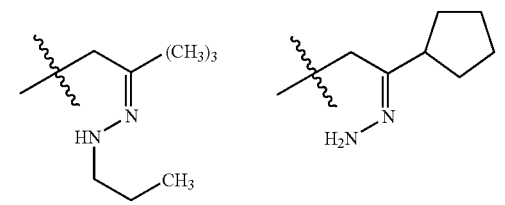
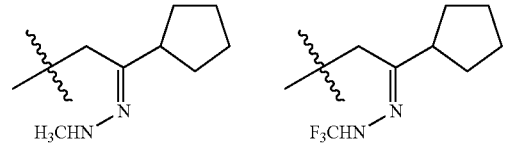
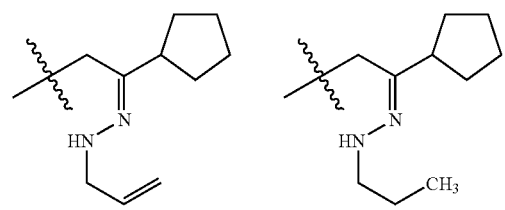
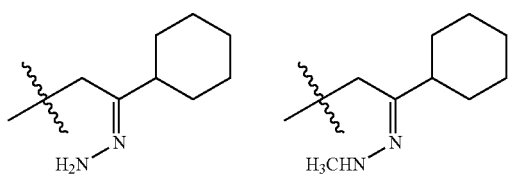
In another aspect the disclosure provides compounds of formula VII, having formula VIII or formula IX:
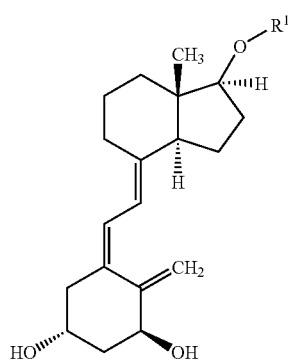

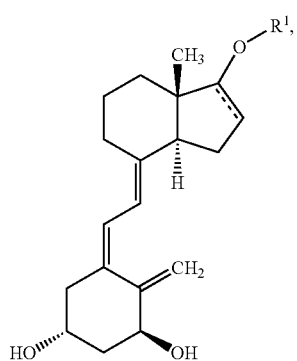
wherein:
R[1] is independently:
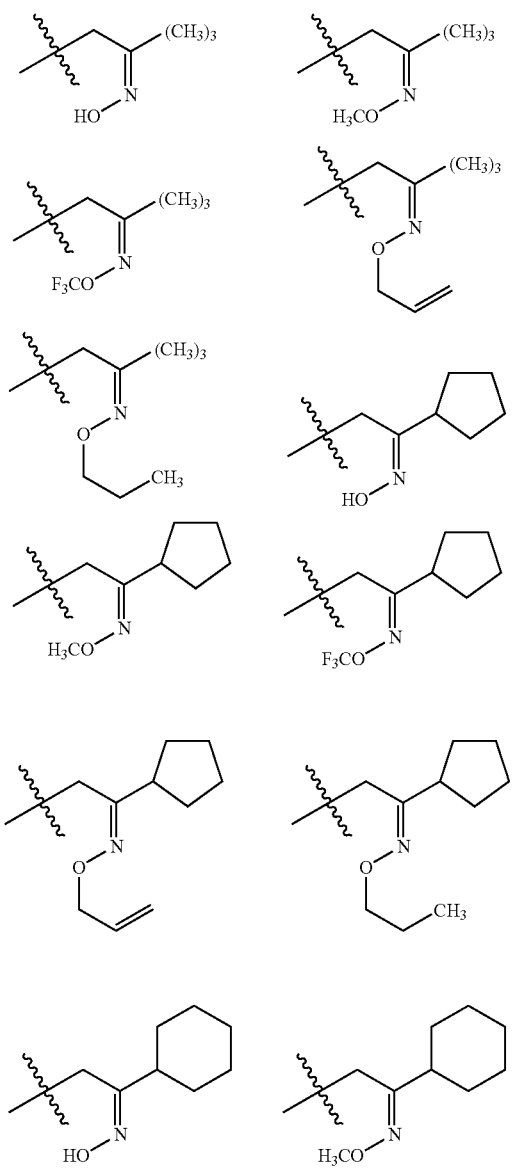
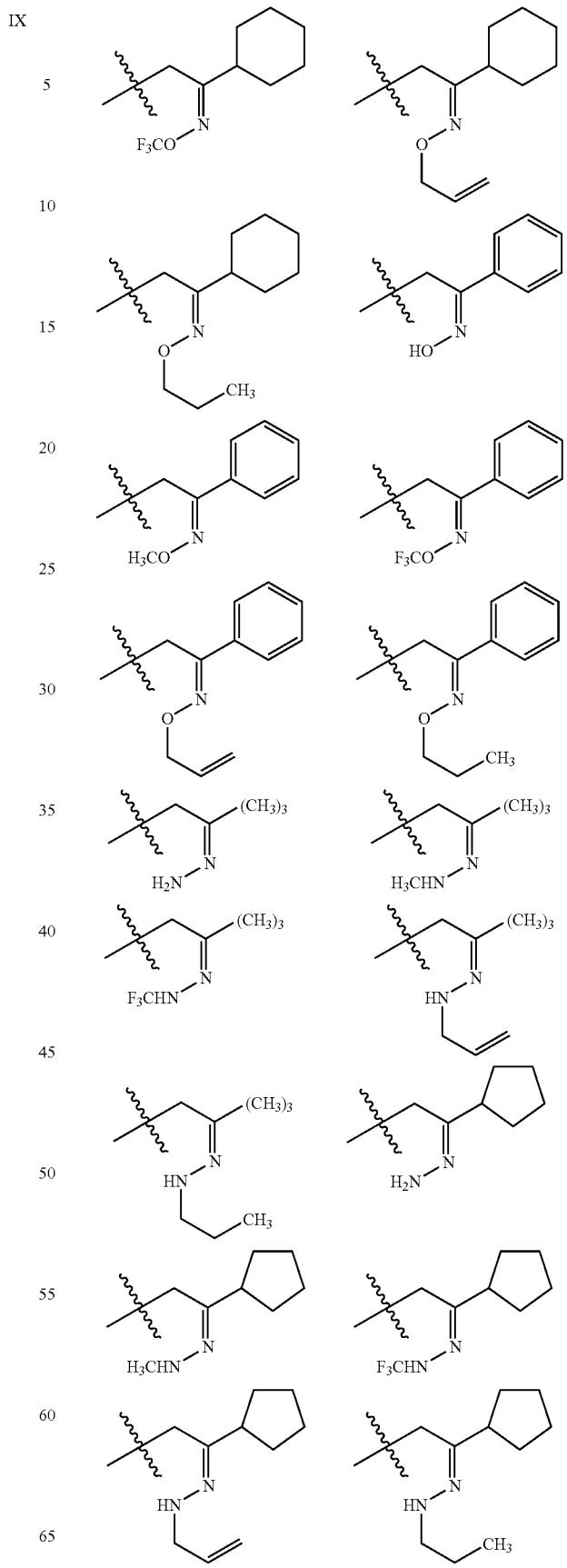

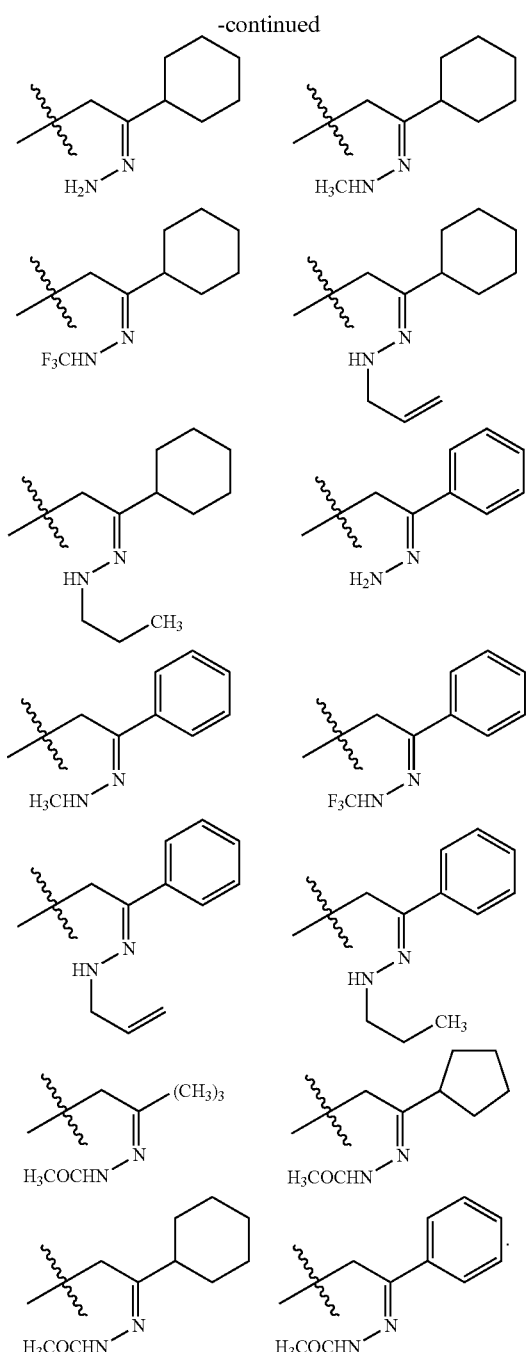

In another aspect the disclosure provides compounds of formula VII, wherein:

$R^1$ is independently substituted or unsubstituted aryl, substituted or unsubstituted arylalkyl, substituted or unsubstituted heteroaryl, or substituted or unsubstituted heteroarylalkyl; and $R^3$ is independently H, F, Cl, Br, I, OH, CN, $NO_2$, substituted or unsubstituted alkyl, perfluoroalkyl, substituted or unsubstituted cycloalkyl, substituted or unsubstituted alkenyl, substituted or unsubstituted cycloalkenyl, substituted or unsubstituted alkynyl, substituted or unsubstituted aryl, substituted or unsubstituted arylalkyl, substituted or unsubstituted heteroaryl, substituted or unsubstituted heteroarylalkyl, $-(CH_2)_jOR^4$, $-(CH_2)_jC(O)R^4$, $-(CH_2)_jC(NR^7)R^4$, $-(CH_2)_jC(NNR^7)R^4$, $-(CH_2)_jC(O)OR^4$, $-(CH_2)_jNR^5R^6$, $-(CH_2)_jC(O)NR^5R^6$, $-(CH_2)_jOC(O)NR^5R^6$, $-(CH_2)_jNR^7C(O)R^4$, $-(CH_2)_jNR^7C(O)OR^4$, $-(CH_2)_jNR^7C(O)NR^5R^6$, $-(CH_2)_jS(O)_mR^8$, $-(CH_2)_jNR^7S(O)_2R^8$, or $-(CH_2)_jS(O)_2NR^5R^6$.

In another aspect the disclosure provides compounds of formula VII, wherein:

$R^1$ is independently substituted or unsubstituted phenyl, substituted or unsubstituted naphthyl, substituted or unsubstituted furanyl, substituted or unsubstituted pyrrolyl, substituted or unsubstituted thiofuranyl, substituted or unsubstituted oxazolyl, substituted or unsubstituted isooxazolyl, substituted or unsubstituted pyrazolyl, substituted or unsubstituted imidazolyl, substituted or unsubstituted pyridinyl, substituted or unsubstituted pyridazinyl, substituted or unsubstituted pyrimidinyl, substituted or unsubstituted pyrazinyl, wherein $R^1$ is optionally independently substituted with 1 to 3 $R^3$ groups; and $R^3$ is independently F, Cl, Br, I, OH, CN, $NO_2$, alkyl, perfluoroalkyl, cycloalkyl, alkenyl, cycloalkenyl, alkynyl, aryl, arylalkyl, heteroaryl, heteroarylalkyl, $-(CH_2)_jOR^4$, $-(CH_2)_jC(O)R^4$, $-(CH_2)_jC(NR^7)R^4$, $-(CH_2)_jC(NNR^7)R^4$, $-(CH_2)_jC(O)OR^4$, $-(CH_2)_jNR^5R^6$, $-(CH_2)_jC(O)NR^5R^6$, $-(CH_2)_jOC(O)NR^5R^6$, $-(CH_2)_jNR^7C(O)R^4$, $-(CH_2)_jNR^7C(O)OR^4$, $-(CH_2)_jNR^7C(O)NR^5R^6$, $-(CH_2)_jS(O)_mR^8$, $-(CH_2)_jNR^7S(O)_2R^8$, or $-(CH_2)_jS(O)_2NR^5R^6$.

In another aspect the disclosure provides compounds of formula VII, wherein:

$R^1$ is independently:

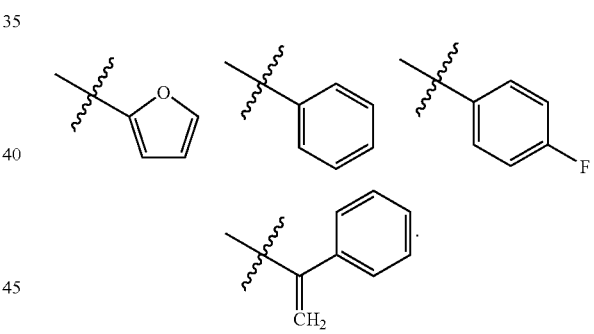

In another aspect the disclosure provides compounds of formula VII, having formula VIII or formula IX:

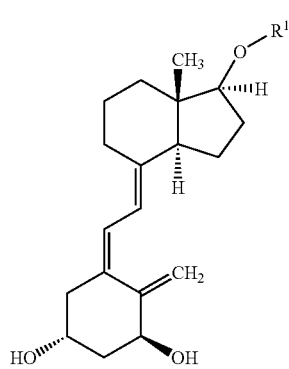

VIII

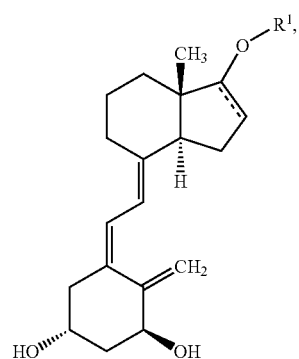
wherein:
$R^1$ is independently:
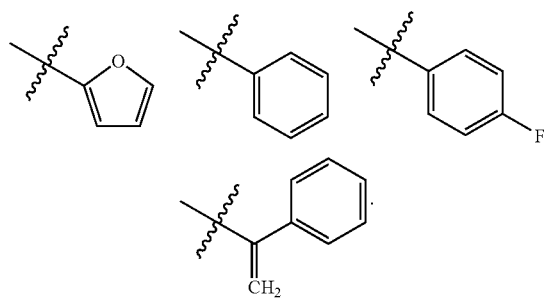
In another aspect the disclosure provides compounds having formula:
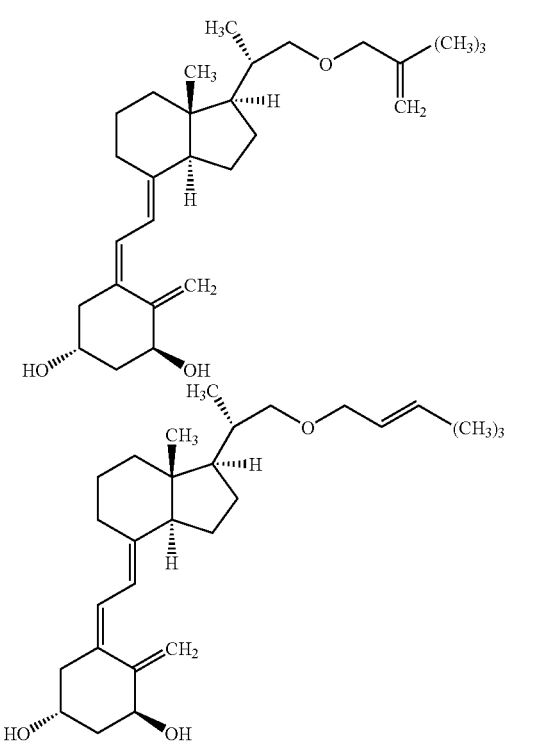
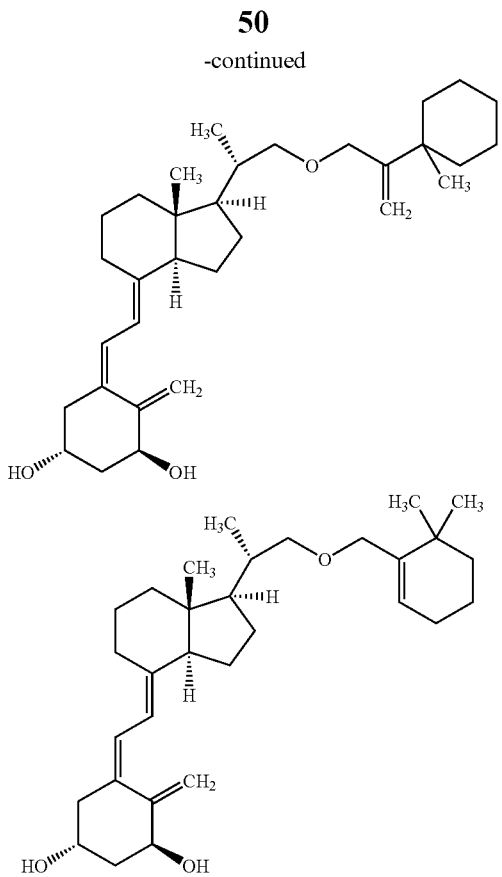
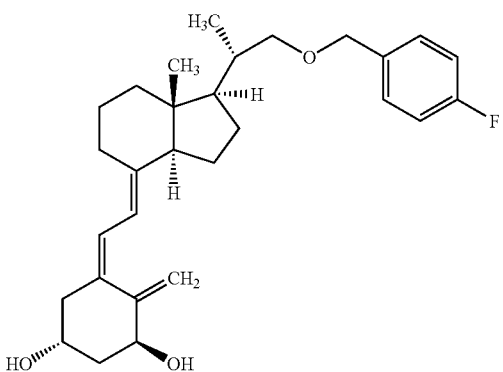
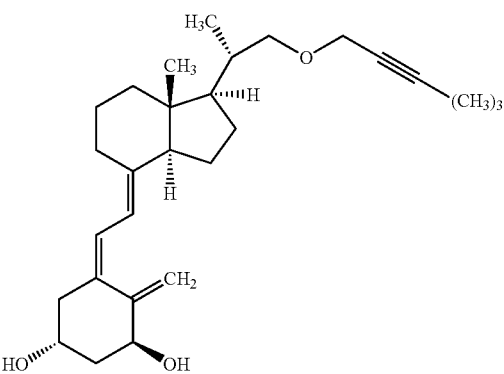

51
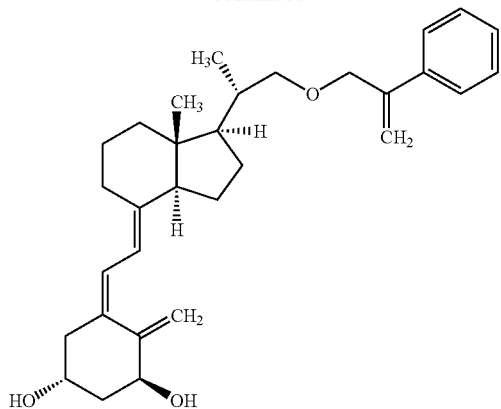
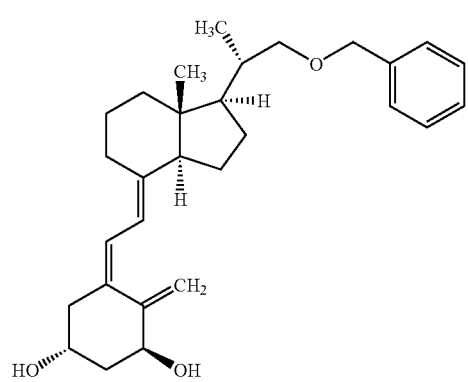
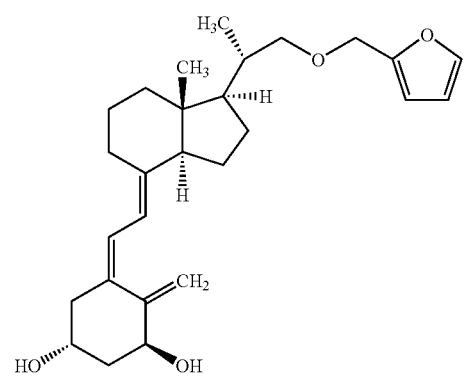
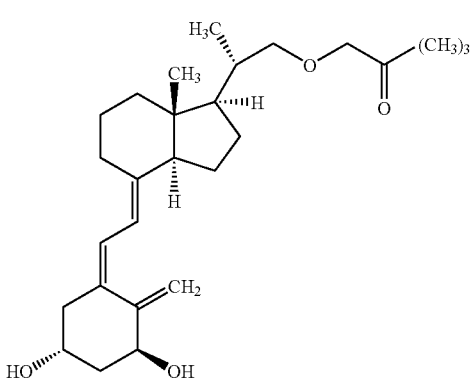
52
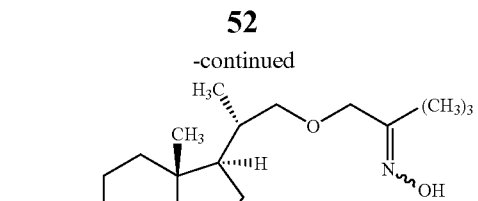
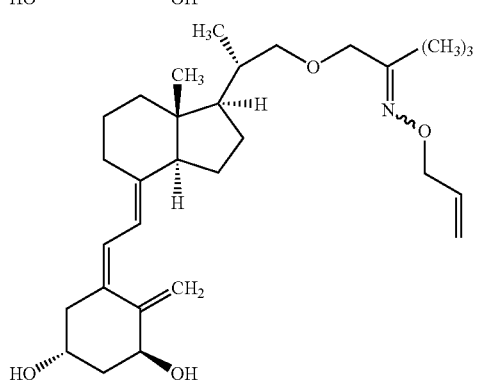
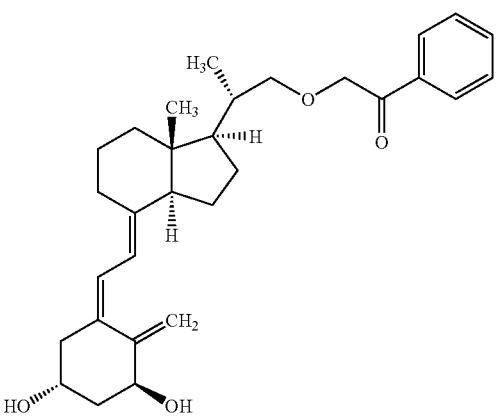
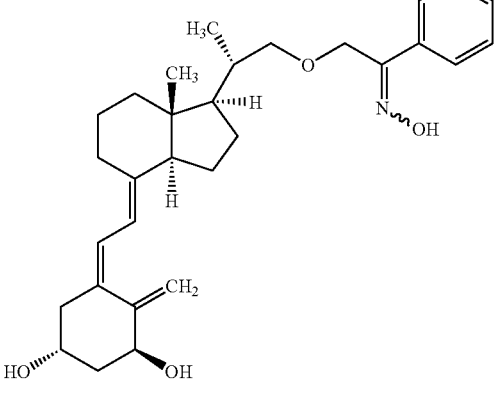

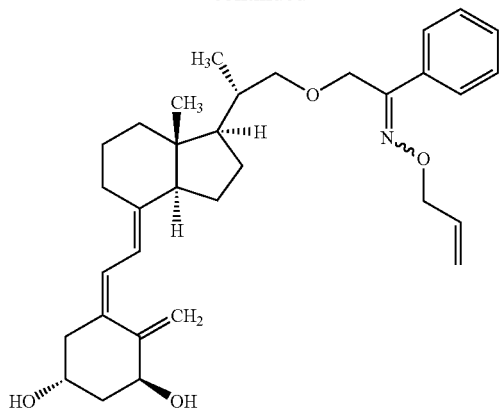

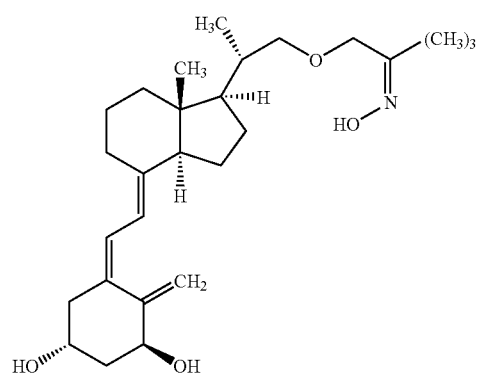

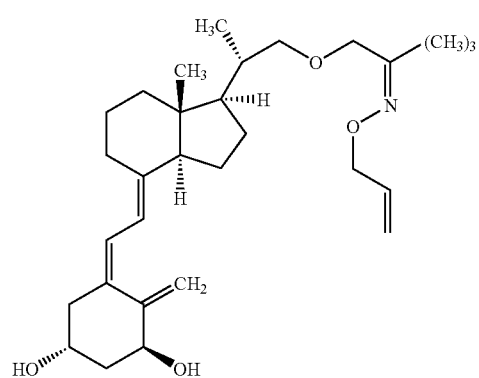

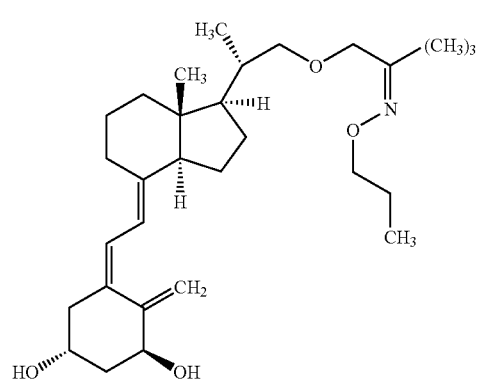

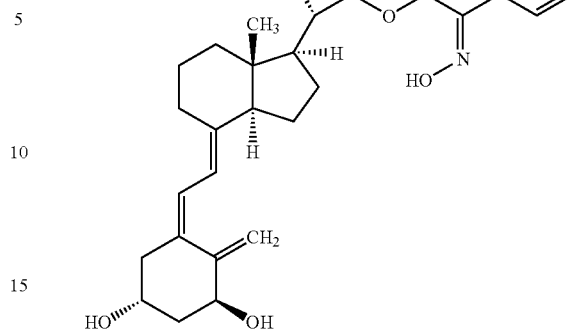

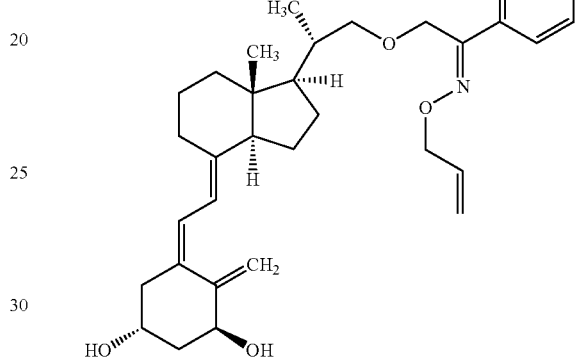

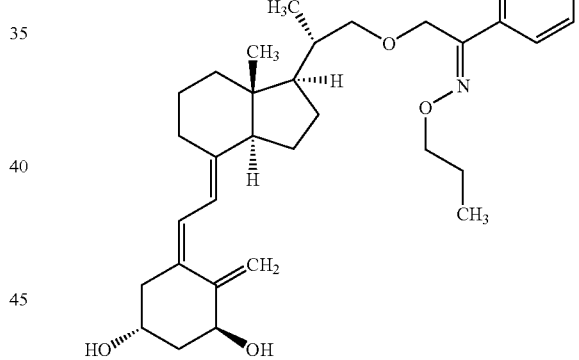

or a pharmaceutically acceptable salt of solvate thereof.

In another aspect the disclosure provides pharmaceutical compositions containing an effective amount of one or more of the compounds of formula I, together with one or more pharmaceutically acceptable carriers.

In another aspect the disclosure provides pharmaceutical compositions containing an effective amount of one or more of the compounds of formula I, together with one or more pharmaceutically acceptable carriers, wherein the pharmaceutical composition is in topical form.

In another aspect the disclosure provides pharmaceutical compositions containing an effective amount of one or more of the compounds of formula I, together with one or more pharmaceutically acceptable carriers, wherein the pharmaceutical composition is in topical, oral or injectable form.

In another aspect the disclosure provides methods for treating patients suffering from disorders characterized by abnormal cell-proliferation and/or cell-differentiation, by administering an effective amount of a compound of formula I, or a pharmaceutical composition containing a compound of formula I, to the patient in need of such treatment.

In another aspect the disclosure provides methods for treating patients suffering from disorders characterized by abnormal cell-proliferation and/or cell-differentiation, comprising administering an effective amount of a compound of formula I, or a pharmaceutical composition containing a compound of formula I, to the patient in need of such treatment, wherein the abnormal cell proliferation and/or cell-differentiation is psoriasis.

In another aspect the disclosure provides methods for treating patients suffering from secondary hyperparathyroidism, by administering an effective amount of a compound of formula I, or a pharmaceutical composition containing a compound of formula I, to the patient in need of such treatment.

In another aspect the disclosure provides methods for treating patients suffering from secondary hyperparathyroidism, by administering an effective amount of a compound of formula I, or a pharmaceutical composition containing a compound of formula I, to the patient in need of such treatment, wherein the patient is suffering from chronic kidney disease (CKD).

In another aspect the disclosure provides methods for preparing a compound of formula I, comprising:
a) reacting the compound of formula XI with base to form the corresponding anion; and
b) coupling the anion with the compound of formula XII:

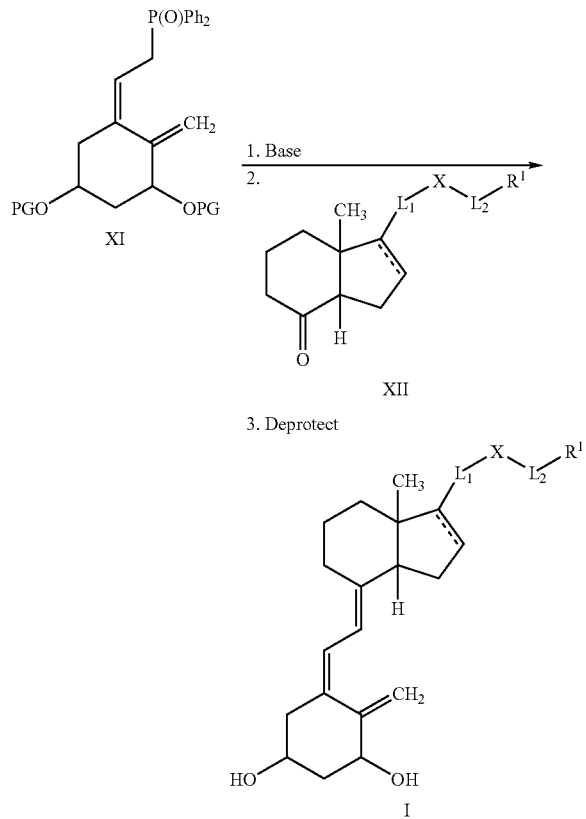

wherein PG is a protecting group; and
c) removing the protecting groups to provide the compound of formula I.

In another aspect the disclosure provides methods for preparing a compound of formula I, comprising:
a) reacting the compound of formula XI with base to form the corresponding anion, wherein the base is an alkali metal or organolithium compound; and
b) coupling the anion with the compound of formula XII, wherein the protecting group is a silyl protecting group; and
c) removing the protecting groups to provide the compound of formula I.

In another aspect the disclosure provides methods for preparing a compound of formula I, comprising:
a) reacting the compound of formula XI with base to form the corresponding anion, wherein the base is an alkali metal or organolithium compound, wherein the alkali metal is sodium hydride or lithium hydride, and the organolithium compound is n-butyl lithium, sec-butyl lithium or tert-butyl lithium; and
b) coupling the anion with the compound of formula XII, wherein the protecting group is tert-butydimethylsilane; and
c) removing the protecting groups to provide the compound of formula I.

In another aspect the disclosure provides the compound of formula I, prepared by any of the methods disclosed herein. Secondary Hyperparathyroidism and Chronic Kidney Disease (CKD)

Secondary hyperparathyroidism (SHPT) is a disorder which develops primarily because of Vitamin D deficiency. It is characterized by abnormally elevated blood levels of parathyroid hormone (PTH) and, in the absence of early detection and treatment; it becomes associated with parathyroid gland hyperplasia and a constellation of metabolic bone diseases. It is a common complication of chronic kidney disease (CKD), with rising incidence as CKD progresses. Secondary hyperparathyroidism can also develop in individuals with healthy kidneys, due to environmental, cultural or dietary factors which prevent adequate Vitamin D supply.

Bone and joint pain are common, as are limb deformities in secondary hyperparathyroidism. The elevated PTH has also pleiotropic effects on blood, immune system and neurological system.

The compounds of formula I may be useful for treating the suppression of parathyroid hormone (PTH) levels in patients who have secondary hyperparathyroidism. The compounds of formula I may be able to bind with high affinity to vitamin D receptors (VDRs) not only in the parathyroid glands, but also in cells throughout the body. For example, recent data has shown that pulsatile, intravenous vitamin D treatment (calcitriol or paricalcitol) confers a survival advantage in the dialysis population through VDR activation. The compounds of formula I may also effect VDR activation, particularly in the predialysis stages of CKD where high mortality rates from cardiovascular disease have recently been documented. Previous underutilization of calcitriol treatment to control PTH levels in Stages 3 and 4 CKD was often due to concerns about its potential for accelerating the progression of CKD as a consequence of hypercalcemia, hypercalciuria, or hyperphosphatemia. The compounds of formula I, however, may show more selective VDR activity and therefore, have greater potential for preventing parathyroid hyperplasia and bone loss in early CKD without adversely affecting kidney function. Further, the compounds of formula I may also reduce cardiovascular morbidity and mortality in early CKD.

Preparation of the Compounds of Formula I

The disclosed compounds may be readily prepared from inexpensive vitamin $D_2$. It has been shown that vitamin $D_2$ may be fragmented and converted into C,D-ring building block 23-alcohol 2. [Posner, G. H. et al.; *J. Org. Chem.* 1997, 62, 3299-3314] Starting with the C,D-ring 23-alcohol 2, Williamson ether coupling and C-8 desilyation produced the 23-oxa ethers 4a-d, g-i, f in 30-85% yields (Scheme I).

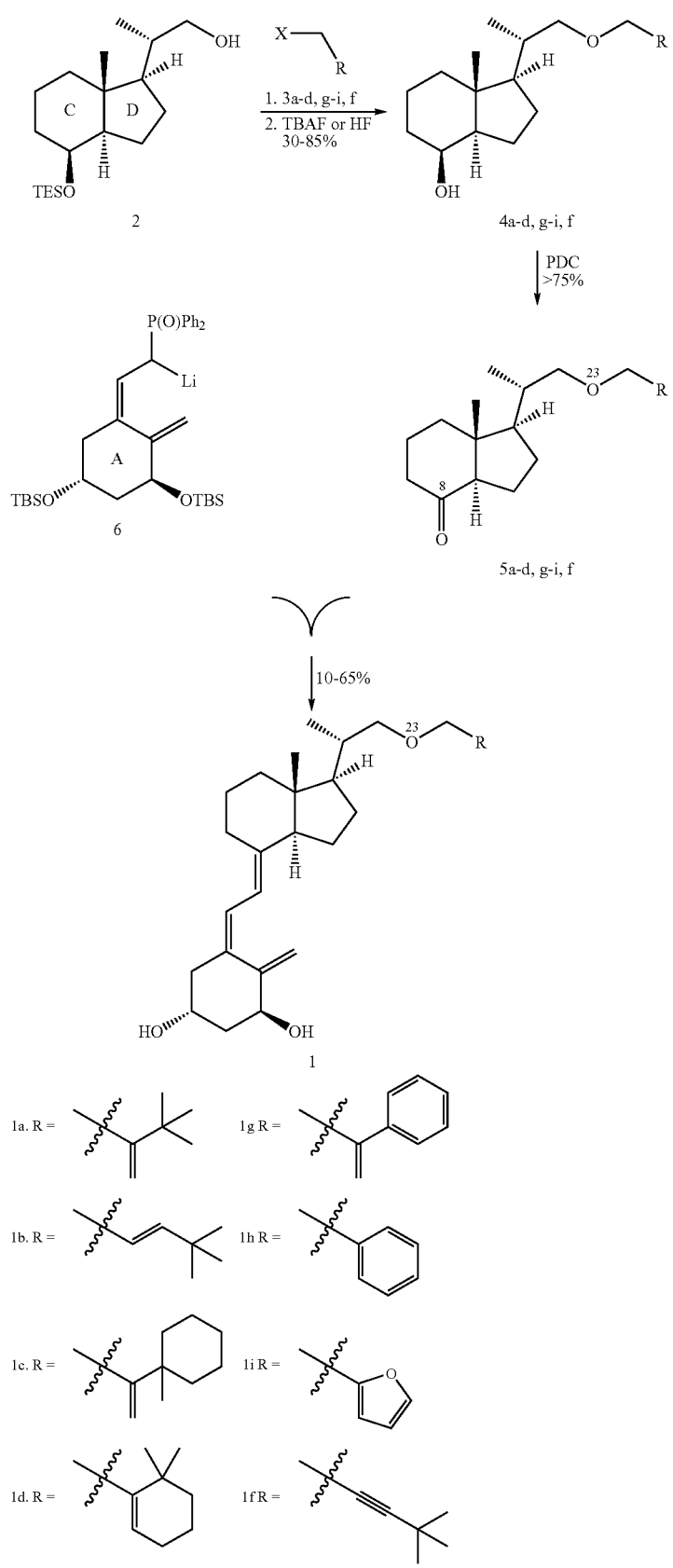

Analog 1i was made in an umpolung manner starting with CD-ring C-22 iodide [Mascareñas, J. L. et al.; *J. Org. Chem.* 1986, 51, 1269-1272] and furfuryl alcohol. Oxidation of 4a-d, g-i, f with PDC (pyridinium dichromate) produced C-8 ketones 5 a-d, g-i, f in >75% yields. Coupling of C-8 ketones with the known [Daniewski, A. R. et al.; *J. Org. Chem.* 2002, 67, 1580-1587] A-ring lithiophosphine oxide 6, and then desilylation afforded the desired 23 oxa ether analogs KSP-23-oxa-25-CH$_2$-26TB (1a), KSP-23-oxa-25-ene-26-TB (1b), KSP-23-oxa-25-C(CH$_2$)-McCyclohex (1c), KSP-23-oxa-CH$_2$Me$_2$cyclohexene (1d), KSP-23-oxa-25-C(CH$_2$)-Ph (1g), KSP-23-oxa-24-CH$_2$Ph (1h), KSP-23-oxa-furfuryl (1i), and KSP-23-oxa-25yne-TB (1f) in 10-65% yields.

The convergent nature of synthetic Scheme I and the relatively small number of chemical steps between starting materials and target analog suggest that large scale manufacture of a lead drug candidate should be feasible and economically favorable. All of these 23-oxa analogs (without the natural 25-OH group) except furan analog 1i are more lipophilic (higher log P) than the natural hormone A (Table I).

Other examples of the disclosed compounds of formula I include analogs 1a-1o as shown below in Scheme II.

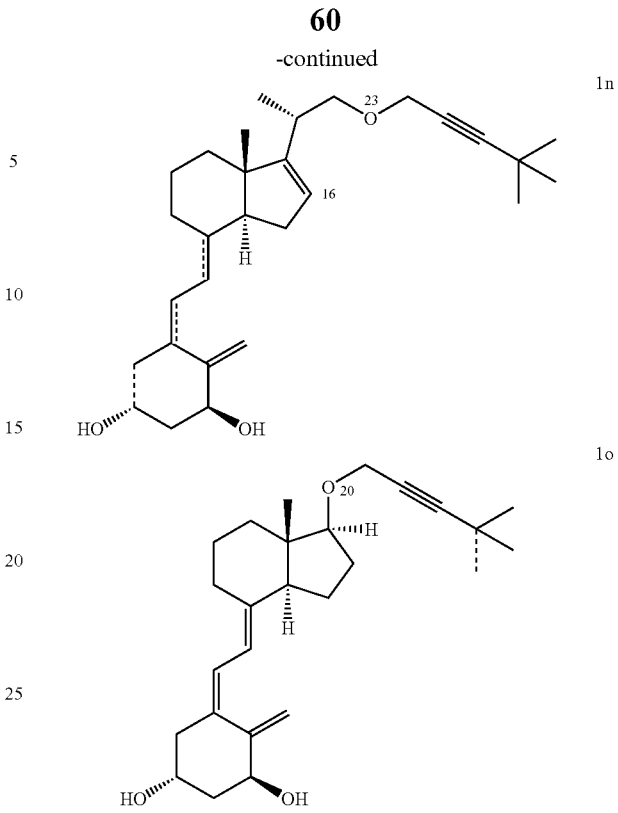

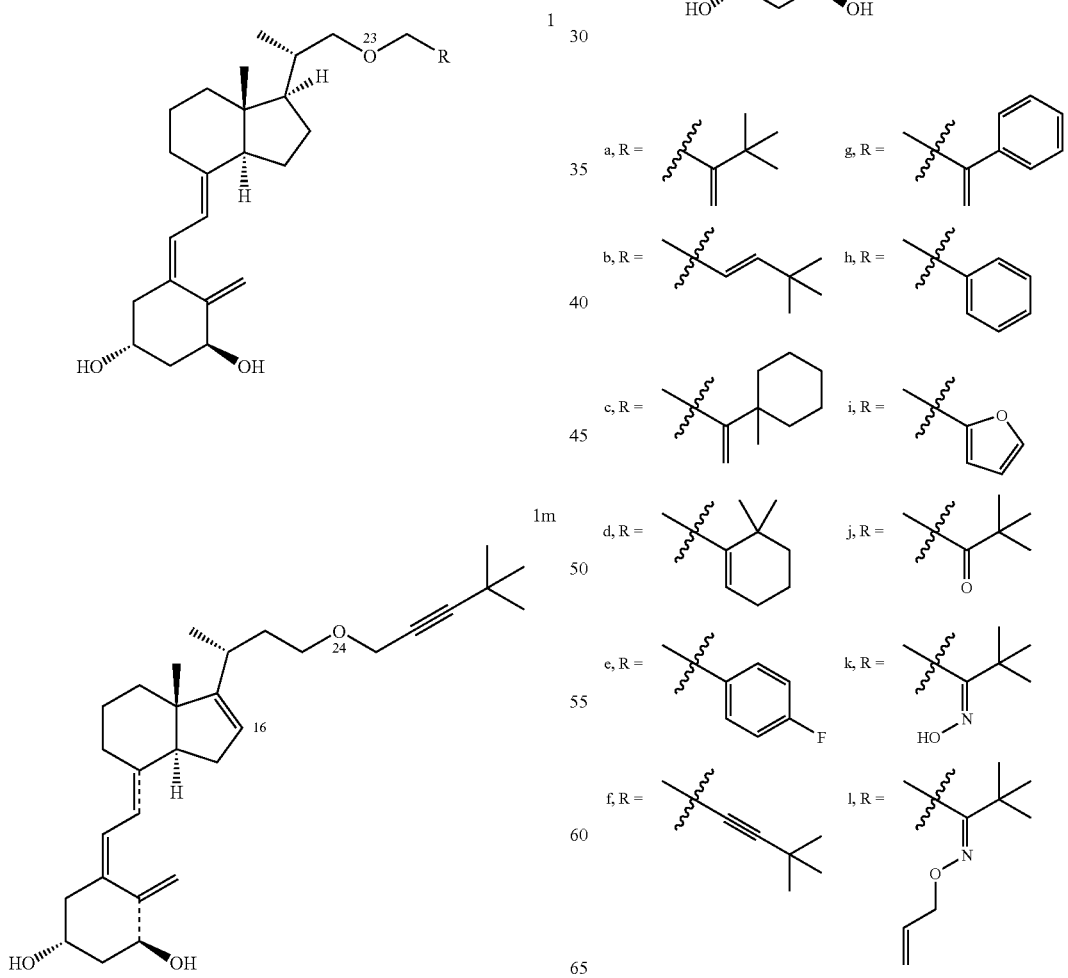

Also disclosed are compounds of formula I as shown in Scheme III.

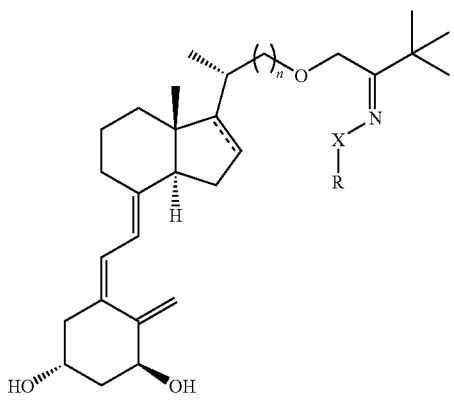

Scheme III n = 0-2
X = O, N
R = allyl, CF₃, CH₃, isopropyl, H

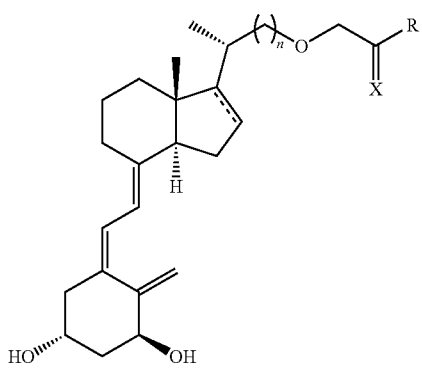

n = 0-2
X = O, CH₂
R = t-butyl, aryl, cyclohexyl, cyclopentyl

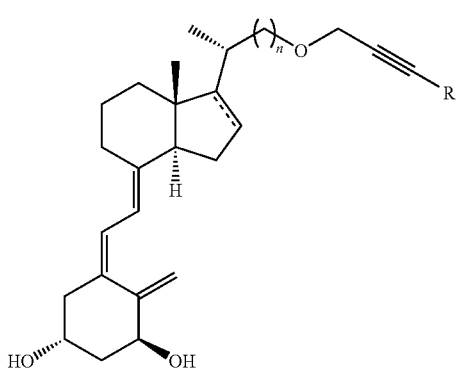

n = 0-2
R = t-butyl, aryl, cyclohexyl, cyclopentyl

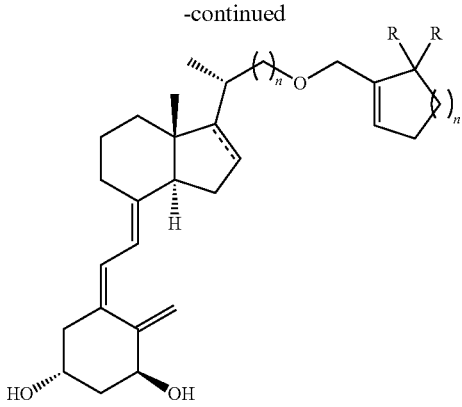

n = 0-2
R = CH₃, CF₃, F

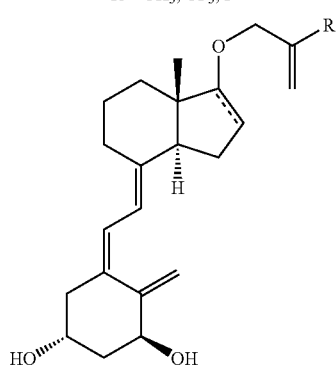

R = t-butyl, aryl, cyclohexyl, cyclopentyl

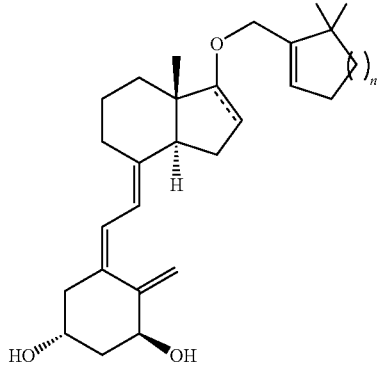

n = 0-2
R = CH₃, CF₃, F

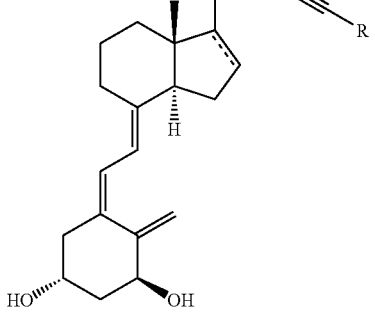

R = t-butyl, aryl, cyclohexyl, cyclopentyl

A standard in vitro protocol [Posner, G. H. et al.; *J. Org. Chem.* 1997, 62, 3299-3314] for determining antiproliferative activity of new analogs 1a-d, g-i, f in murine keratinocytes produced the data shown in Table I. Noteworthy is the exceptionally high antiproliferative potency of allylic ether analogs 1a and 1d and especially of propargylic ether analog 1f (Table I). Propargylic ether analog 1f, with an $IC_{50}$ of 2 nM, is approximately 40 times more antiproliferative than the natural hormone A ($IC_{50}$=80 nM). [Peleg, S. et al.; *J. Med. Chem.* 2006, 49, 7513-7517]

TABLE I

| Analog | Antiproliferative $IC_{50}^a$ (nM) | Transcriptional Activity $ED_{50}$ (nM) | Competitive VDR Binding $IC_{50}$ (nM) | Calciuria Activity Compared to 1 | Log P |
|---|---|---|---|---|---|
| A | 80 | 1.5 | 0.8 | 1 | 3.6 |
| 1a | 20 | 6 | 85 | <0.02 | 4.7 |
| 1b | 400 | —$^a$ | —$^a$ | —$^a$ | 4.9 |
| 1c | 100 | 350 | 198 | <0.02 | 5.3 |
| 1d | 50 | 52 | 300 | <0.02 | 4.9 |
| 1f | 2 | 40 | 47 | <0.02 | 4.6 |
| 1g | 400 | —$^a$ | —$^a$ | —$^a$ | 5.1 |
| 1h | 180 | 410 | 63 | <0.02 | 4.4 |
| 1i | 600 | —$^a$ | —$^a$ | —$^a$ | 3.3 |

Log P values were calculated using ChemAxon's Marvin and calculator plugin demo. The purity of analogs 1a-d, g-i, f was judged to be ≥96% based on HPLC analysis.

Biology of the Compounds of Formula I

A standard in vitro protocol [Posner, G. H. et al.; *J. Org. Chem.* 1997, 62, 3299-3314] for determining antiproliferative activity of new analogs 1a-d, g-i, f in murine keratinocytes produced the data shown in Table I. Noteworthy is the exceptionally high antiproliferative potency of allylic ether analogs 1a and 1d and especially of propargylic ether analog 1f (Table I). Propargylic ether analog 1f, with an $IC_{50}$ of 2 nM, is approximately 40 times more antiproliferative than the natural hormone A ($IC_{50}$=80 nM).

A standard protocol [Liu, Y. Y. et al.; *J. Biol. Chem.* 1997, 272, 3336-3345] using a recombinant human VDR and a reporter gene containing a vitamin D response element (VDRE) gave the transcriptional potencies of 23-oxa analog 1a-d, g-i, f as shown in Table I. Noteworthy is the very high transcriptional potency of allylic ether 1a ($ED_{50}$=6 nM), approaching that of A ($ED_{50}$=1.5 nM).

A standard assay for competitive binding to the human VDR generated the $IC_{50}$ values shown in Table I. Noteworthy is that allylic ether 1a binds to the human VDR only about 1% as well as natural hormone A but nevertheless is almost as transcriptionally potent and is more antiproliferative than A. Noteworthy also is that propargylic ether 1f binds to the human VDR only twice as well as allylic ether 1a but is approximately ten times more antiproliferative than 1a. [Peleg, C. et al.; *Mol. Endocrinol.* 1998, 12, 524-535]

A standard in vivo [Posner, G. H. et al.; *J. Med. Chem.* 1998, 41, 3008-3014] assay probed the calciuric activity of these new 23-oxa analogs. Remarkably, 23-oxa allylic ethers 1a and 1d and 23-oxa propargylic ether 1f are at least 50 times less calciuric than A (FIG. 1). Thus, the 23-oxa allylic ether 1a lacking a 25-OH group has a substantial therapeutic window, and the 23-oxa propargylic ether 1f also lacking a 25-OH group has an even better therapeutic window, comparing favorably to that of the Chugai drug [Kubodera, N., *Current Bioactive Compounds* 2006, 2, 301-315; Allewaert, K. et al.; *Steroids* 1994, 59, 686-690] 22-oxa-25-hydroxy B.

It is expected that in vivo catabolism (hydroxylation) [Jones, G. et al.; *Physiological Reviews* 1998, 4, 1193-1231] of this series of 23-oxa analogs by cytochrome P-450 enzymes will occur mainly at C-24 due to the radical-stabilizing effect of the 23-oxygen atom and to the radical-stabilizing effect also of the adjacent olefinic or acetylenic multiple bond. Since such allylic or propargylic radical intermediates would be stabilized by resonance delocalization, they are expected to be formed more easily than in saturated 23-oxa side-chain analogs. Thus, the in vivo half-life of 23-oxa allylic ethers 1a and 1d and of propargylic ether 1f is expected to be shorter than that of the natural hormone A, leading in all three cases to side-chain fragmentation and formation of the same 22-$CH_2$—OH alcohol that is only weakly antiproliferative (data not shown). An analog's having a relatively short half-life in vivo may represent a therapeutic advantage in minimizing any undesirable calciuric activity, as is the case for the topically used antipsoriasis drug calcipotriol. [Masuda, S. et al.; *J. Bio. Chem.* 1994, 269, 4794-4803]

Three of these new lipophilic analogs of A possess a very desirable therapeutic profile of high antiproliferative activity and desirably low calcemic activity. Of these three, 23-oxa allylic ether 1a and especially 23-oxa propargylic ether 1f feature the best combination of structural features leading to high antiproliferative activity and low calcemic activity. Based on these promising results, further evaluation of the pharmacological properties and the medical potential of these easily and convergently synthesized 23-oxa vitamin D new chemical entities is appropriate and timely.

Protecting Groups

The compounds of the present disclosure may be synthesized using one or more protecting groups generally known in the art of chemical synthesis. The term "protecting group" refers to chemical moieties that block some or all reactive moieties of a compound and prevent such moieties from participating in chemical reactions until the protective group is removed, for example, those moieties listed and described in Greene, et al., Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups may be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and may be subsequently removed by metal or pi-acid catalysts. For example, an allyl-blocked carboxylic acid may be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Silyl ethers are a group of chemical compounds that contain a silicon atom covalently bonded to an alkoxy group and are commonly used as protecting groups for alcohols. The general structure may be represented as $R^1R^2R^3Si—O—R^4$ where $R^4$ is an alkyl group or an aryl group. Since $R^1R^2R^3$ may be combinations of differing groups that may be varied in order to provide a number of silyl ethers, this protecting group provides a wide spectrum of selectivity for protecting group chemistry. Common silyl ethers include but are not limited to trimethylsilyl (TMS), triethylsilyl (TES), tert-butyldiphenylsilyl (TBDPS), tert-butyldimethylsilyl (TBS/TBDMS) and triisopropylsilyl (TIPS). They are particularly useful because they may be installed and removed very selectively under mild conditions Typical blocking or protecting groups include, for example:

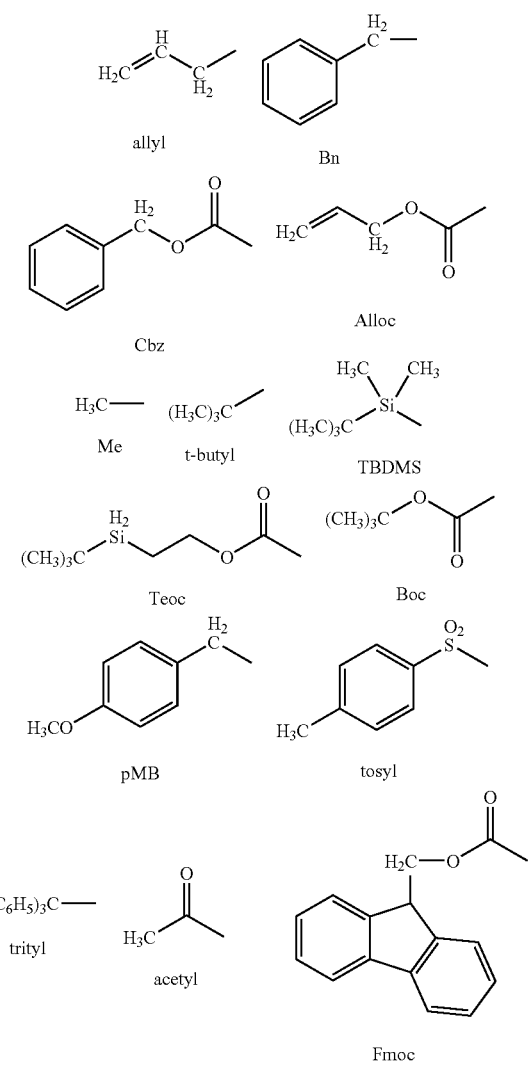

Pharmaceutical Compositions and Administration

In another aspect, the present disclosure provides pharmaceutical compositions including one or more compounds of formula I in admixture with one or more pharmaceutically acceptable excipients. One of skill in the art will recognize that the pharmaceutical compositions include the pharmaceutically acceptable salts of the compound of formula I as described above.

The disclosed compounds of formula I are intended for use in pharmaceutical compositions which are useful in the treatment of human and veterinary disorders which, as mentioned above, are characterized by abnormal cell-proliferation and/or differentiation. In therapeutic and/or diagnostic applications, the compounds of the disclosure may be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

The disclosed compounds of formula I may be effective over a wide dosage range. For example, in the treatment of adult humans, dosages from 0.001 to 1000 mg per day may be applicable. In other embodiments, the dosages may range from 0.5 to 100 mg; from 1 to 50 mg per day, and/or from 5 to 40 mg per day may be used. A preferable dosage is 1 to 30 mg per day, however, the exact dosage will depend upon the route of administration, the form in which the compound is administered, the subject to be treated, the body weight of the subject to be treated, and the preference and experience of the attending physician.

The disclosed compounds may be administered by the parenteral, enteral or topical routes. They are well absorbed when given enterally and this is the preferred form of administration in the treatment of systemic disorders. In the treatment of dermatological disorders like psoriasis, topical forms like ointments, creams or lotions are preferred. In the treatment of systemic disorders, a compound of formula I may be administered in daily doses ranging from 0.001-1000 mg, with 1-50 mg doses being preferred. In the topical treatment of dermatological disorders, ointments, creams or lotions containing from 0.001-1000 mg/g, and preferably from 1-50 mg, of a compound of formula I may be administered. The oral compositions may be formulated as tablets, capsules, or drops, containing from 0.001-1000 mg, preferably from 1-50 mg, of a compound of formula I, per dosage unit. While it is possible for an active ingredient to be administered alone as the raw chemical, it is preferable to present it as a pharmaceutical formulation.

The term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present disclosure comprise an active ingredient in association with a pharmaceutically acceptable carrier, and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present disclosure suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applications; oil-in-water or water-in-oil emulsions such as creams, ointments or pastes; or solutions or suspensions such as drops.

In addition to the aforementioned ingredients, the formulations of the disclosure may include one or more additional ingredients such as diluents, buffers, flavoring agents, binders, surface active agents, thickeners, lubricants, preservatives, e.g. methyl hydroxybenzoate (including anti-oxidants), emulsifying agents and the like.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained- low release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds may be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a patient to be treated.

For nasal or inhalation delivery, the agents of the disclosure may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which may be used pharmaceutically. The preparations formulated for oral administration may be in the form of tablets, dragees, capsules, or solutions.

Pharmaceutical preparations for oral use may be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that may be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

The disclosed compositions may further contain other therapeutically active compounds usually applied in the treatment of the above mentioned pathological conditions. Depending upon the particular condition, or disease state, to be treated or prevented, additional therapeutic agents, which are normally administered to treat or prevent that condition, may be administered together with the inhibitors of this disclosure. For example, chemotherapeutic agents or other anti-proliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this disclosure may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

The compounds described above may be provided as pharmaceutically acceptable formulations using formulation methods known to those of ordinary skill in the art. These formulations may be administered by standard routes. In general, the combinations may be administered by the topical, transdermal, oral, rectal or parenteral (e.g., intravenous, subcutaneous or intramuscular) route. In addition, the combinations may be incorporated into biodegradable polymers allowing for sustained release of the compound, the polymers being implanted in the vicinity of where drug delivery is desired.

The present disclosure is not to be limited in scope by the exemplified embodiments, which are intended as illustrations of single aspects of the disclosure. Indeed, various modifications of the disclosure in addition to those described herein will become apparent to those having skill in the art from the foregoing description. Such modifications are intended to fall within the scope of the disclosure. Moreover, any one or more features of any embodiment of the disclosure may be combined with any one or more other features of any other embodiment of the disclosure, without departing from the scope of the disclosure. References cited throughout this application are examples of the level of skill in the art and are hereby incorporated by reference herein in their entirety for all purposes, whether previously specifically incorporated or not.

The disclosure will now be further described in the following non-limiting examples.

EXAMPLES

The following examples are offered to illustrate, but not to limit the claimed invention.

Example 1

Preparation of Analogs 1a-1i

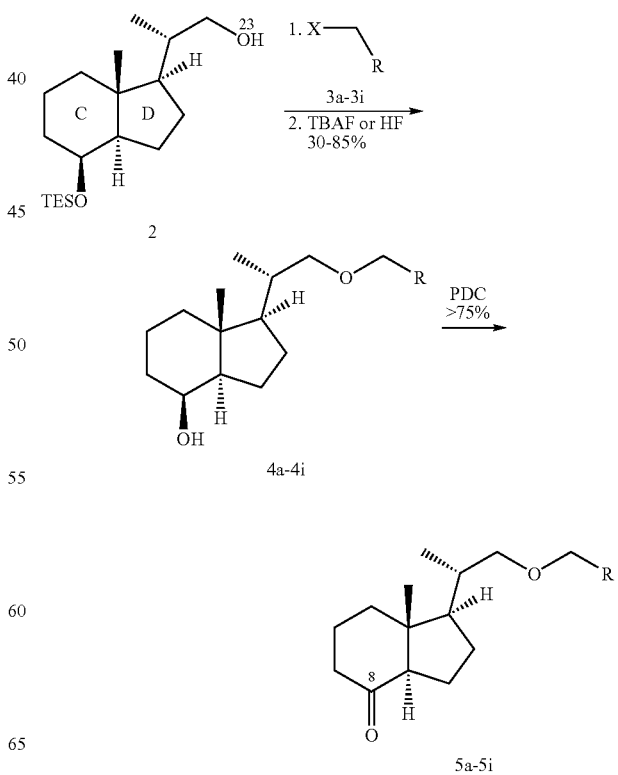

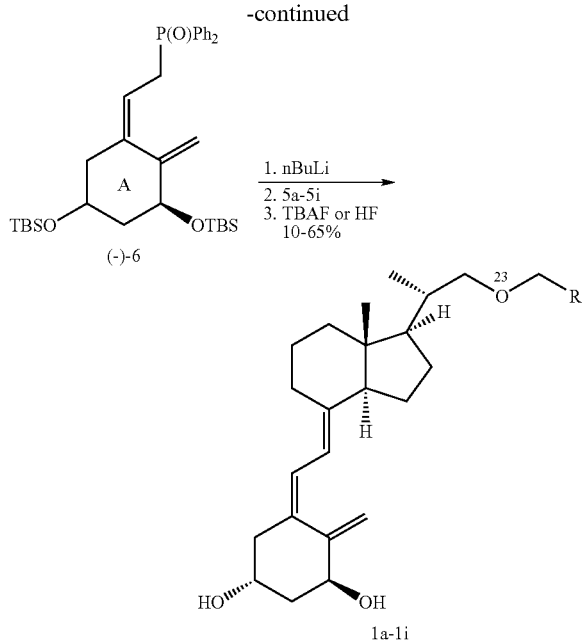

Compounds 1a-1i (except 1e) were made as previously described.[2]

Ketone 5e

To an ice-cooled solution of 2[3] (45 mg, 0.14 mmol) in DMF (2 mL), NaH (11 mg of a 60% suspension in mineral oil, 0.28 mmol) was added. The mixture was stirred at room temperature for 1 h until a light yellow color developed. After cooling the mixture to 0° C., 4-fluorobenzyl bromide (34 μL, 0.28 mmol) was added to the reaction flask and the mixture was stirred at room temperature for 14 h. The reaction was quenched by addition of water and extracted with $CH_2Cl_2$ (dichloromethane) (3×5 mL). The combined organic extracts were dried over $MgSO_4$, filtered, concentrated, and purified by column chromatography (5% ethyl acetate in hexanes) to afford 56 mg of crude TES protected alcohol. The crude TES protected alcohol was dissolved in $CH_3CN$ (3 mL) and HF (160 μL, 3.86 mmol) was added. The solution was stirred 2 h before being quenched with a solution of saturated $NaHCO_3$. The mixture was extracted with ethyl acetate (3×5 mL), washed with brine, dried over $MgSO_4$, and concentrated in vacuo. Column chromatography (20% ethyl acetate in hexanes) afforded 17 mg of the alcohol 4e as a colorless oil in 40% yield for the 2 steps. $[\alpha]_D^{29}$+42.3 (c 0.20, $CHCl_3$); IR (neat, $cm^{-1}$) 3457 (brs), 2933 (m), 2866 (m), 1604 (w), 1509 (m), 1456 (w), 1222 (m), 1091 (m) 944 (w), 823 (w), 772 (w); $^1H$ NMR ($CDCl_3$, 400 MHz) δ 7.29 (m, 2H), 7.02 (m, 2H), 4.43 (q, 2H, J=14.4 Hz), 4.08 (m, 1H) 3.41 (dd, 1H, J=9.2, 3.6 Hz), 3.18 (dd, 1H, J=8.8, 7.2 Hz), 1.99 (m, 1H), 1.87-1.14 (m, 13H), 1.04 (d, 3H, J=6.8 Hz), 0.95 (s, 3H); $^{13}C$ NMR ($CDCl_3$, 100 MHz) δ 162.22 (d, J=243 Hz), 149.60 (d, J=4 Hz), 129.18 (d, J=8 Hz), 115.11 (d, J=21 Hz), 75.54, 72.35, 69.28, 53.48, 52.37, 41.95, 40.24, 36.35, 33.63, 26.71, 22.60, 17.45, 17.41, 13.57; $^{19}F$ NMR (282 MHz, $CDCl_3$) δ−115.86 (septet, J=2.82 Hz).

A solution of the alcohol 4e (12 mg, 0.04 mmol) in $CH_2Cl_2$ (2 mL) was cannulated into a reaction vessel equipped with PDC (42 mg, 0.11 mmol) and oven dried Celite® (45 mg). After stirring overnight the mixture was filtered, concentrated in vacuo, and purified by column chromatography (20% ethyl acetate in hexanes) to afford 12 mg of ketone 5e as a colorless oil in 96% yield. $[\alpha]_D^{29}$+2.8 (c 0.20, $CHCl_3$); IR (neat, $cm^{-1}$) 2957 (m), 2874 (m), 1713 (s), 1509 (m), 1456 (w), 1359 (w), 1221 (w), 1091 (w); $^1H$ NMR ($CDCl_3$, 400 MHz) δ 7.29 (m, 2H), 7.02 (m, 2H), 4.44 (q, 2H, J=211.6 Hz), 3.41 (dd, 1H, J=8.8, 3.2 Hz), 3.22 (dd, 1H, J=8.8, 6.8 Hz), 2.44 (m, 1H), 2.24 (m, 2H), 2.11 (m, 1H), 1.83-1.51 (m, 9H), 1.09 (d, 3H, J=6.4 Hz), 0.64 (s, 3H); $^{13}C$ NMR ($CDCl_3$, 100 MHz) δ 211.73, 162.24 (d, J=244 Hz), 134.44 (d, J=3 Hz), 129.19 (d, J=32 Hz), 115.15 (d, J=21 Hz), 75.27, 72.42, 61.67, 53.47, 49.89, 40.94, 38.82, 36.52, 27.03, 24.01, 19.16, 17.65, 12.50; $^{19}F$ NMR (282 MHz, $CDCl_3$) δ −115.68 (septet, J=5.64 Hz); HRMS: calcd for $C_{20}H_{27}FO_2$ [MH+]: 319.2073, found 319.2076.

Analog 1e

Enantiomerically pure phosphine oxide (−)-6[3] and CD-ring ketone 5e, were separately azeotropically dried with anhydrous benzene (3×5 mL) on a rotary evaporator and held under vacuum (ca. 0.1 mm Hg) for at least 48 hours prior to use.

A flame-dried 10 mL recovery flask equipped with a magnetic stir bar and an Ar balloon was charged with phosphine oxide (−)-6 (33 mg, 0.06 mmol). The reagent was dissolved in 2.0 mL freshly distilled THF (tetrahydrofuran) and cooled to −78° C. To this solution n-BuLi (35 μL, 0.06 mmol, 1.60 M solution in hexanes) was added drop-wise over several minutes during which time a deep red color developed and persisted. This mixture was allowed to stir at −78° C. for an additional 30 min. Meanwhile, a flame-dried 10 mL flask containing CD-ring ketone 5e (7 mg, 0.021 mmol) was dissolved in 0.75 mL of freshly distilled THF and cooled to −78° C. The solution of CD-ring ketone 5e was transferred drop-wise into the flask containing the phosphine oxide anion at −78° C. via cannula over several minutes. After the addition was complete, the deep red color persisted and the mixture was allowed to stir at −78° C. for 4 h. Upon observation of a light yellow color, the reaction was quenched with 5 mL of pH 7 buffer and allowed to warm to room temperature. The mixture was extracted with ethyl acetate (3×15 mL). The combined organic extracts were washed with water and brine, dried over $MgSO_4$, and filtered. The filtrate was concentrated in vacuo to give crude a product that was purified by column chromatography (5% ethyl acetate in hexanes with 1% $NEt_3$) affording 12 mg of the protected product. The protected analog was dissolved in THF (2 mL) and tetra-n-butylammonium fluoride (TBAF) (1.0 M in THF, 180 μL, 0.18 mmol) was added. After stirring overnight the reaction was quenched with $H_2O$ and extracted with $CH_2Cl_2$ (3×5 mL), dried over $MgSO_4$, and filtered. The filtrate was concentrated in vacuo to give the crude product that was purified by column chromatography (50-75% ethyl acetate in hexanes with 1% $NEt_3$) to afford 6 mg of analog 1e as an oil (53% yield for 2 steps). $[\alpha]_D^{25}$+24.9 (c 0.30, $CHCl_3$); IR (neat, $cm^{-1}$) 3355 (brs), 2943 (m), 2872 (m), 1604 (w), 1509 (m), 1222 (m), 1056 (w), 824 (w), 756 (w); $^1H$ NMR ($CDCl_3$, 400 MHz) δ 7.28 (m, 2H), 7.02 (m, 2H), 6.38 (d, 1H, J=11.2 Hz), 6.02 (d, 1H, J=11.2 Hz), 5.32 (s, 1H), 5.00 (s, 1H), 4.45 (m, 3H), 4.23 (m, 1H), 3.43 (dd, 1H, J=8.8, 3.2 Hz), 3.18 (dd, 1H, J=8.8, 7.2 Hz), 2.83 (m, 1H), 2.60 (m, 1H) 2.31 (dd, 1H, J=13.2, 6.4 Hz), 2.08-1.16 (m, 16H), 1.07 (d, 3H, J=6.8 Hz), 0.56 (s, 3H); $^{13}C$ NMR ($CDCl_3$, 100 MHz) δ 162.22 (d, J=244 Hz), 147.66, 142.99, 134.57 (d, J=3 Hz), 132.99, 129.20 (d, J=8 Hz), 124.95, 117.09, 115.13 (d, J=21 Hz), 111.76, 75.58, 72.36, 70.84, 66.86, 56.06, 53.34, 46.00, 45.28, 42.89, 40.32, 37.16, 29.07, 27.18, 23.55, 22.36, 17.70, 12.04; $^{19}F$ NMR (282 MHz, $CDCl_3$) δ −115.83 (septet, J=8.46 Hz); HRMS: calcd for $C_{29}H_{39}FO_3$ [M+]: 454.2883, found 454.2875; UV (MeOH) $\lambda_{max}$ 263 nm ($\epsilon$14,702).

Example 2

Preparation of Analogs 1j-1k

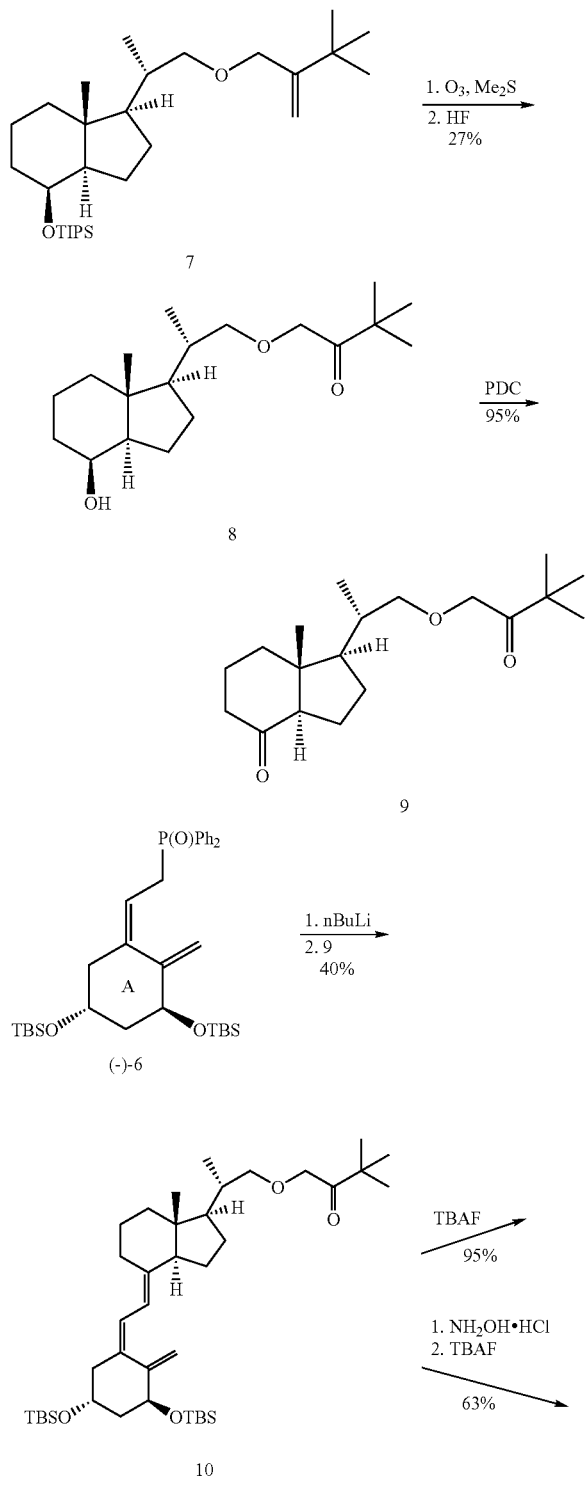

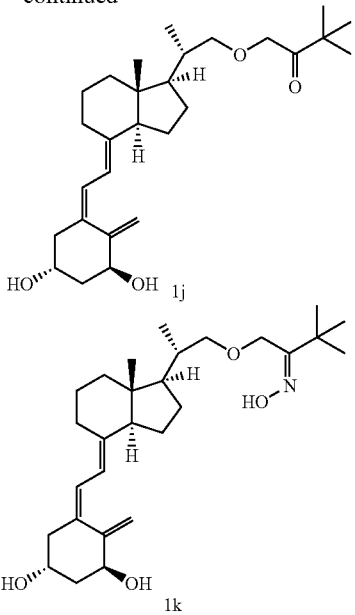

Compound 1j was made as previously reported.[5]

Analog 1k

Enantiomerically pure phosphine oxide (–)-6 and CD-ring ketone 9,[5] were separately azeotropically dried with anhydrous benzene (4×5 mL) on a rotary evaporator and held under vacuum (ca. 0.1 mm Hg) for at least 48 hours prior to use.

A flame-dried 10 mL recovery flask equipped with a magnetic stir bar and an Ar balloon was charged with phosphine oxide (–)-6 (28 mg, 0.048 mmol). The reagent was dissolved in 2.0 mL freshly distilled THF and cooled to –78° C. To this solution n-BuLi (32 μL, 0.06 mmol, 1.50 M solution in hexanes) was added drop-wise over several minutes during which time a deep red color developed and persisted. This mixture was allowed to stir at –78° C. for an additional 10 min. Meanwhile, a flame-dried 10 mL flask containing CD-ring ketone 9 (7 mg, 0.024 mmol) was dissolved in 0.75 mL of freshly distilled THF and cooled to –78° C. The solution of CD-ring ketone 9 was transferred drop-wise into the flask containing the phosphine oxide anion at –78° C. via cannula over several minutes. After the addition was complete, the deep red color persisted and the mixture was allowed to stir at –78° C. for 3 h. Upon observation of a light yellow color, the reaction was quenched with 5 mL of pH 7 buffer and allowed to warm to room temperature. The mixture was extracted with ethyl acetate (3×15 mL). The combined organic extracts were washed with water and brine, dried over $MgSO_4$, and filtered. The filtrate was concentrated in vacuo to give crude product that was purified by column chromatography (5% ethyl acetate in hexanes with 1% $NEt_3$) affording 4.3 mg of 10 in a 27% yield. Compound 10 was dissolved in anhydrous pyridine (3 mL) and hydroxyl amine hydrochloride (8 mg, 0.12 mmol) was added. The mixture was stirred under Ar for 15 h. The reaction mixture was purified by directly using silica gel column chromatography (10% ethyl acetate in hexanes with 1% $NEt_3$). The protected oxime analog was dissolved in THF (2 mL) and TBAF (1.0 M in THF, 200 μL), along with one drop $NEt_3$ was added. After stirring overnight the reaction was quenched with $H_2O$ and extracted with $CH_2Cl_2$ (3×5 mL), dried over $MgSO_4$, and filtered. The filtrate was concentrated in vacuo to give the crude product that was purified by column chromatography (75% ethyl acetate in hexanes with 1% NEt$_3$) to afford 1.7 mg of analog 1k as an oil (63% yield for 2 steps). $[\alpha]_D^{23}$+28.5 (c 0.085, CHCl$_3$); IR (neat, cm$^{-1}$) 3328 (brs), 2925 (m), 2853 (m), 2363 (s), 2334 (s), 1464 (w), 1111 (w), 951 (w); $^1$H NMR (CDCl$_3$, 400 MHz) δ 6.38 (d, 1H, J=11.2 Hz), 6.02 (d, 1H, J=11.2 Hz), 5.33 (t, 1H, J=2.0 Hz), 5.00 (m, 1H), 4.43 (m, 1H), 4.24 (m, 3H), 3.93 (m, 2H), 3.45 (dd, 1H, J=8.8, 3.2 Hz), 3.20 (dd, 1H, J=8.8, 7.6 Hz), 2.83 (dd, 1H, J=12.0, 4.0 Hz), 2.60 (dd, 1H, J=13.2, 3.6 Hz), 2.31 (dd, 1H, J=13.2, 6.4 Hz), 2.08-1.14 (m, 23H), 1.04 (d, 3H, J=6.8 Hz), 0.86 (m, 3H), 0.56 (s, 3H); $^{13}$C NMR (CDCl$_3$, 100 MHz) δ 163.69, 147.63, 142.99, 132.95, 124.97, 117.08, 111.78, 70.84, 66.86, 62.81, 56.05, 53.27, 45.99, 45.26, 42.86, 40.32, 37.03, 36.92, 29.06, 27.93, 27.19, 23.54, 22.35, 17.62, 14.11, 12.05; HRMS: calcd for C$_{28}$H$_{46}$NO$_4$ [MNa+]: 482.3241, found 482.3227; UV (MeOH) $\lambda_{max}$ 264 nm ($\epsilon$21,634).

Example 3

Preparation of Analog 11

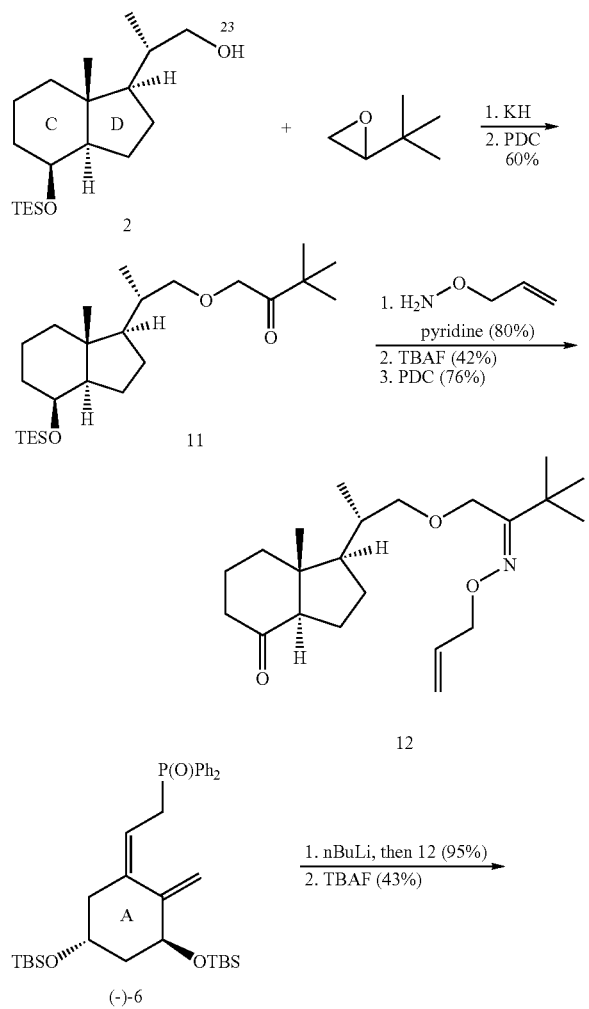

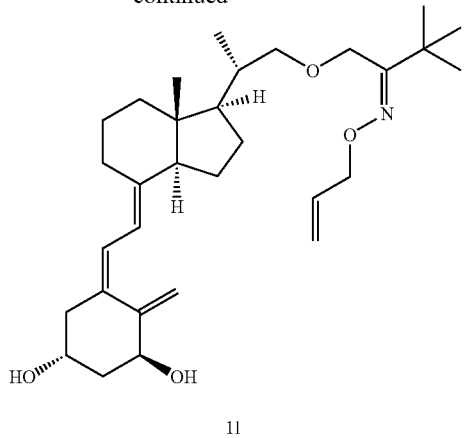

Analog 11

KH (30%, 0.15 g, 1.1 mmol, 5 equiv.) was washed with hexanes and dried under vacuum for 2 hours in a 25 mL round-bottom flask. In a separate 10 mL round-bottom flask TES protected alcohol 2 (0.07 g, 0.215 mmol, 1 equiv.) was dissolved in dry THF (1.5 mL) and cannulated into the KH. The solution was allowed to stir for 2-3 hours until an orange/yellow color persisted. At this time 1,2-epoxy-3,3-dimethylbutane was added and the reaction was allowed to stir overnight at room temperature. TLC analysis had indicated the reaction had gone to completion, and it was quenched with water and extracted with CH$_2$Cl$_2$ (3×). The combined organic layers were dried over anhydrous MgSO$_4$ and concentrated in vacuo. The crude alcohol was used in the next step without further purification. The alcohol was dissolved in CH$_2$Cl$_2$, and PDC (0.62 g. 1.6 mmol, 1.5 equiv.) and Celite® (0.24 g) was added. The reaction mixture was allowed to stir overnight. TLC analysis had indicated the reaction had gone to completion. The reaction mixture was filtered over Celite® and purified via column chromatography using 25% ethyl acetate in hexanes to yield the desired ketone 11 (0.055 g, 0.13 mmol) in 60% chemical yield. $^1$H NMR data matched that of the known compound.[5]

To a 10 mL round-bottom flask was added 11 (0.04 g, 0.1 mmol, 1 equiv.) and O-allyl hydroxylamine (0.06 g, 0.05 mmol, 5 equiv.) in anhydrous pyridine (2 mL) The reaction was allowed to stir at room temperature until TLC analysis indicated complete consumption of the starting material. The reaction was quenched with water (10 mL) and extracted with CH$_2$Cl$_2$ (3×), dried over MgSO$_4$, and purified via column chromatography to yield the desired TES protected oxime (0.03 g, 0.08 mmol) in 80% yield. $^1$H NMR (300 MHz, CDCl$_3$) δ 5.95 (m, 1H); 5.18 (m, 3H); 4.55 (d, 2H, J=6 Hz); 4.22 (m, 3H); 3.40 (dd, 1H, J=8.7, 3.0 Hz); 3.15 (t, 1H, J=8.7 Hz); 2.0 (m, 1H); 1.85 (m, 3H); 1.7-0.8 (m, 26H). To a 10 mL round-bottom flask charged with the oxime (0.05 g, 0.1 mmol, 1 equiv.) in anhydrous THF (2 mL) was added 0.3 mL of a 1M solution of TBAF in THF at −78° C. The reaction was allowed to slowly warm to room temperature and stir overnight. TLC analysis indicated complete consumption of starting material. The reaction was then quenched with water and extracted with CH$_2$Cl$_2$ (3×), dried over anhydrous MgSO$_4$, and purified via column chromatography to yield the desired alcohol (0.015 g, 0.1 mmol) in 42% yield. $^1$H NMR (300 MHz, CDCl$_3$) δ 5.95 (m, 1H); 5.18 (m, 3H); 4.55 (d, 2 H, J=6.1 Hz); 4.22 (m, 3H); 3.40 (dd, 1H, J=8.6, 3.0 Hz); 3.17 (t, 1H, J=8.6 Hz); 2.0 (m, 1H); 1.85 (m, 3H); 1.7-0.8 (m, 26H). To a 10 mL round-bottom flask was added the alcohol (0.015 g, 0.041 mmol, 1 equiv.), PDC (0.045, 0.12 mmol, 2.9 equiv.) and Celite® (0.05 g) in anhydrous $CH_2Cl_2$ (2 mL). The reaction mixture was allowed to stir overnight at room temperature. TLC analysis indicated complete consumption of the starting material. The reaction was then filtered over Celite®, and purified via column chromatography to yield the desired ketone 12 (0.011 g, 0.036 mmol) in 76% yield. $^1$H NMR (300 MHz, $CDCl_3$) δ 5.96 (m, 1H); 5.29 (m, 2H); 4.55 (m, 2H); 4.13 (q, 2H, J=21.3 Hz); 3.38 (m, 1H); 3.22 (m, 1H); 2.41 (m, 1H); 2.28 (m, 2H); 2.15-0.81 (25H).

To a round-bottom flask charged with phosphine oxide 6 (0.063 g, 0.11 mmol, 2.9 equiv.) in anhydrous THF (2 mL) was added 0.065 mL of a 1M solution of n-BuLi in THF dropwise at −78° C. At this time the reaction mixture turned bright reddish-orange and was allowed to stir for 20 min at −78° C. A pre-cooled solution of ketone 12 (0.012 g, 0.037 mmol, 1 equiv.) in THF (1 mL) was added to the lithiated solution via cannula. The reaction was then allowed to stir at −78° C. for 7 hours, after which it was quenched with pH 7 buffer, diluted with water, extracted with $CH_2Cl_2$ (3×), dried over anhydrous $MgSO_4$, and purified via column chromatography to yield the desired TES protected deltanoid (0.025 g, 0.035 mmol) in 95% yield. $^1$H NMR (300 MHz, $CDCl_3$) δ 6.25 (m, 1H); 6.03 (m, 2H); 5.25 (m, 3H); 4.86 (s, 1H); 4.55 (s, 2H); 4.35 (s, 1H); 4.16 (m, 5H); 3.4 (m, 1H); 3.15 (m, 1H); 2.85 (m, 1H); 2.25 (m, 1H); 1.95-0.8 (m, 20H), 0.15 (30H)

To a 10 mL amber glass round-bottom flask charged with the protected analog (0.025 g, 0.035 mmol, 1 equiv.) in anhydrous THF (2 mL) was added a 1M solution of TBAF in THF (0.185 mL, 5 equiv.). The reaction mixture was allowed to stir overnight at room temperature TLC analysis indicated complete consumption of the starting material, and the reaction was quenched with water, extracted with $CH_2Cl_2$ (3×), dried over anhydrous $MgSO_4$ and purified via column chromatography to yield the desired deltanoid 11 (0.0077 g, 0.015 mmol) in 43% yield. $[\alpha]^{21.1}$D 13.5 (c 0.19, $CHCl_3$); IR($CHCl_3$, cm$^{-1}$) 3327, 2924, 2869, 2360, 1647, 1457, 1393, 1363, 1044, 916; $^1$H NMR (400 MHz, $CDCl_3$) δ 6.39 (d, 1H, J=8.7 Hz), 5.98 (m, 2H), 5.33 (m, 3H), 4.99 (s, 1H), 4.54 (s, 1H), 4.43 (s, 1H), 4.26 (m, 4H), 3.41 (m, 1H), 3.15 (m, 1H), 2.82 (d, 1H, J=9.9 Hz), 2.58 (d, 1H, J=12 Hz), 2.36 (m, 1H), 2.05 (m, 6H), 1.86 (m, 3H), 1.7-1.4 (m, 7H), 1.4-1.1 (m, 4H), 1.04 (d, 5H, J=5.1 Hz), 0.89 (m, 4H), 0.55 (s, 4H); $^{13}$C NMR (100 MHz, $CDCl_3$) δ 165.0, 162.0, 148.0, 145.0, 134.5, 132.9, 124.9, 117.6, 116.7, 111.8, 74.5, 70.8, 66.8, 62.8, 56.1, 53.3, 45.9, 45.2, 42.7, 40.3, 37.0, 29.7, 29.1, 28.1, 27.2, 23.6, 22.3, 17.7, 12.0; UV (MeOH) λ max 265 nm (ϵ7612). HRMS: calcd. for $C_{31}H_{29}NO_4Na^+$ =522.3544; found=522.3547.

Example 4

Preparation of Analog 1m

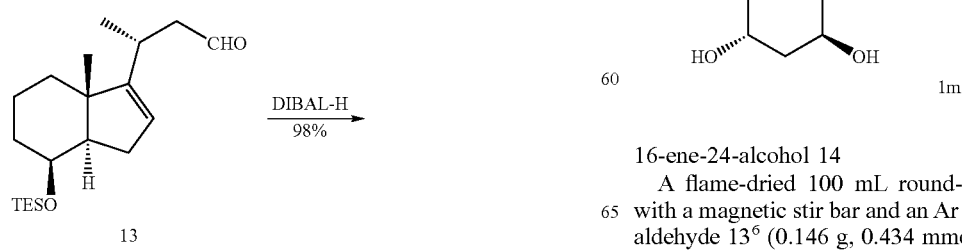

16-ene-24-alcohol 14

A flame-dried 100 mL round-bottomed flask equipped with a magnetic stir bar and an Ar balloon was charged with aldehyde 13$^6$ (0.146 g, 0.434 mmol), 15 mL of dry $CH_2Cl_2$ and cooled to −78 0° C. DIBAL-H (1.5 mL of a 1.0 M solution in CH$_2$Cl$_2$, 1.5 mmol) was syringed into the flask and allowed to stir for 45 minutes. When consumption of the starting material was seen via TLC analysis the reaction was quenched with dilute HCl (0.1 N, 15 mL). The solution was extracted with CH$_2$Cl$_2$, washed with saturated aqueous sodium bicarbonate (10 mL), dried over anhydrous MgSO$_4$ (magnesium sulfate), filtered and purified by column chromatography (1.5:1, hexanes:ethyl acetate) to yield alcohol 14 as a colorless oil (143 mg, 98%). $[\alpha]_D^{25}$=+38.8 (c=7.1, CHCl$_3$); $^1$H NMR (400 MHz, CDCl$_3$) δ 9.63 (t, J=2.4 Hz, 1H), 5.30 (t, J=1.6 Hz, 1H), 4.11 (m, 1H), 2.75-2.66 (m, 1H), 2.58 (dd, J=8.0, 2.8 Hz, 1H), 2.41 (dd, J=7.4, 2.0 Hz, 1H), 2.24 (tt, J=13.2, 1.2 Hz, 1H), 1.92-1.83 (m, 2H), 1.77-1.61 (m, 3H), 1.53-1.44 (m, 2H), 1.43-1.35 (m, 1H), 1.06 (d, 3H), 1.03 (s, 3H), 0.94 (t, J=8.0 Hz, 9H), 0.55 (q, J=8.0 Hz, 6H); $^{13}$C NMR (100 MHz, CDCl$_3$) δ 203.09, 158.68, 121.78, 68.79, 54.94, 49.93, 46.89, 35.90, 34.80, 30.75, 26.59, 22.00, 18.98, 18.02, 6.91, 4.88.

16-ene-24-oxa-26-yne-TB 15

Dry hexanes washed KH (16 mg, 9.0 eq., 0.40 mmol) was added to a 25 mL receiving flask. A solution of alcohol 14 (15 mg, 0.044 mmol) in 2.5 mL of THF was added to the KH and allowed to stir for 45 minutes at room temperature. Propargyltosylate[7] (61 mg, 0.23 mmol) was added and the reaction was allowed to stir at room temperature overnight. The reaction was quenched with water, extracted with ethyl acetate, dried over anhydrous MgSO$_4$, filtered, and concentrated in vacuo. The crude TES-protected alcohol was dissolved in 2.5 mL of THF and TBAF (0.13 mL, 0.13 mL of a 1 M solution in THF) was added to the solution. The mixture was allowed to stir overnight, quenched with water, extracted with ethyl acetate, dried over anhydrous MgSO$_4$, filtered and purified by column chromatography to yield deprotected alcohol 15 in 62% yield for two steps. $[\alpha]_D^{25}$=+27.3 (c 0.75, CHCl$_3$); IR (neat, cm-1) 3466 (br), 2966 (s), 2933 (s), 2700 (m), 2242 (w), 1658 (w), 1475 (w), 1450 (w), 1367 (w), 1259 (w), 1209 (w), 1092 (m), 992 (w), 942 (w); $^1$H NMR (CDCl$_3$, 400 MHz) δ 4.09 (m, 3H), 3.45 (dd, 1H, J) 8.8, 3.2 Hz), 3.24 (dd, 1H, J) 8.8, 6.8 Hz), 1.99 (m, 1H), 1.92-1.03 (m, 22H), 1.02 (d, 3H, J) 6.8 Hz), 0.95 (s, 3H); $^{13}$C NMR (CDCl$_3$, 100 MHz) δ 94.84, 74.80, 74.68, 69.32, 58.62, 53.35, 52.37, 41.88, 40.18, 36.07, 33.61, 30.98, 27.42, 26.63, 22.56, 17.45, 17.41, 13.56; HRMS (FAB) calcd for C$_{20}$H$_{32}$O$_2$ [M−H+], 317.2481; found, 317.2459.

16-ene-24-oxa-26-yne-TB ketone 16

Alcohol 15 (20 mg, 1.0 eq., 0.07 mmol), NMO (13 mg, 1.5 eq., 0.11 mmol), and 4 Å molecular sieves were dissolved in 2 mL of CH$_2$Cl$_2$ in 50 mL receiving flask. After stirring for 10 minutes, TPAP (tetrapropylammonium perruthenate) (1.5 mg, 0.05 eq., 0.004 mmol) was added and the reaction was followed by TLC. After 3 hours the reaction was quenched with water, filtered, extracted with CH$_2$Cl$_2$, dried over anhydrous MgSO$_4$, and purified by column chromatography to yield ketone 16 in 50% yield. $[\alpha]_D^{25}$=+1.22 (c 0.50, CHCl$_3$); IR (neat, cm$^{-1}$) 2968 (s), 2929 (s), 2849 (m), 1714 (s), 1476 (w), 1456 (m), 1381(m), 1358 (m), 1306 (w), 1264 (m), 1239 (w), 1096 (s), 1010 (w), 942 (w), 834 (w); $^1$H NMR (CDCl$_3$, 400 MHz) δ4.09 (m, 2H), 3.43 (dd, 1H, J=8.8, 2.8 Hz), 3.29 (dd, 1H, J=8.8, 6.4 Hz), 2.45 (dd, 1H, J=11.6, 7.6 Hz), 2.28-1.28 (m, 11H), 1.22 (s, 9H), 1.07 (d, 3H, J=6.4 Hz), 0.64 (s, 3H); $^{13}$C NMR (CDCl$_3$, 100 MHz) δ211.88, 94.98, 74.62, 74.36, 61.68, 58.66, 53.30, 49.76, 40.94, 38.75, 36.24, 30.94, 29.67, 26.94, 24.02, 19.09, 17.65, 12.47; HRMS (FAB) calcd for C$_{20}$H$_{30}$O$_2$ [MH+], 317.2481; found, 317.2478.

Analog 1m

Enantiomerically pure phosphine oxide 6 and CD-ring ketone 16, were separately azeotropically dried with anhydrous benzene (3×2 mL) on a rotary evaporator and held under vacuum for 120 hours prior to use. A flame-dried 10 mL round-bottom flask equipped with a magnetic stir bar and an Ar balloon was charged with phosphine oxide 6 (35 mg, 0.060 mmol), dissolved in 1 mL of freshly distilled THF, and cooled to −78° C. To this solution, n-BuLi (33 μL, 0.054 mmol, 1.6 Min hexanes) was added drop-wise over 5 minutes during which time a deep red color developed and persisted. This mixture was allowed to stir at −78° C. for an additional 25 minutes. Meanwhile, a flame-dried 10 mL round-bottomed flask containing CD-ring ketone 16 (9 mg, 0.028 mmol) was dissolved in 1 mL of THF and cooled to −78° C. This solution was transferred drop-wise into the flask containing phosphine oxide anion at −78° C. via cannula over 5 minutes. After the addition was complete, the deep red color persisted and the reaction was allowed to stir at −78° C. for 4 hours. Upon observation of a light yellow color, the reaction was quenched with 3 mL of pH=7 buffer and allowed to warm to room temperature. The mixture was extracted with ethyl acetate (1×5 mL) and methylene chloride (2×5 mL). The combined organic extracts were dried over MgSO$_4$ and filtered. The filtrate was concentrated in vacuo to give crude product that was purified by column chromatography (10% ethyl acetate in hexanes with 1% NEt$_3$), affording the protected analog. The protected analog was dissolved in 2 mL of THF and tetrabutyl-ammonium fluoride (TBAF) (100 μL, 1.6 M solution in THF) was added and the mixture was allowed to stir overnight. The reaction was quenched with water, extracted with ethyl acetate (1×5 mL) and methylene chloride (2×5 mL). The combined organic extracts were dried over MgSO$_4$ and filtered. The filtrate was concentrated in vacuo, and the crude product was purified by column chromatography (70% ethyl acetate in hexanes with 1% NEt$_3$) to afford 1m (2.3 mg, 0.005 mmol, 58%) as a colorless oil. $[\alpha]_D^{25}$=+22.7 (c=0.35, CHCl$_3$); IR (thin film) 3300, 2960, 2873, 1651, 1487, 1375, 932, 870 cm$^{-1}$; $^1$H NMR (400 MHz, CDCl$_3$) δ 6.25 (d, J=11.2 Hz, 1H), 6.09 (d, J=11.2 Hz, 1H), 5.32 (t, J=1.6 Hz, 1H), 5.30 (m, 1H), 5.00 (m, 1H), 4.42-4.44 (m, 1H), 4.20-4.4.26 (m, 1H), 3.80 (bs, 1H), 2.78-2.83 (m, 1H), 2.40-2.61 (m, 3H), 2.29-2.38 (m, 2H), 2.13-2.24 (m, 2H), 1.90-1.93 (m, 2H), 1.60-1.89 (m, 6 H), 1.45-1.54 (m, 1H), 1.35 (s, 3H), 1.34 (s, 3H), 1.04 (d, J=6.8 Hz, 3H), 0.66 (s, 3H); $^{13}$C NMR (100 MHz, CDCl$_3$) δ 158.60, 151.55, 147.65, 143.10, 132.91, 124.98, 117.04, 111.76, 94.88, 74.78, 70.84, 66.85, 58.61, 56.07, 53.23, 45.95, 45.27, 42.87, 40.26, 36.86, 31.92, 29.69, 29.07, 27.11, 25.50, 23.55, 18.76, 11.26; HRMS (FAB) calcd 452.3292 for C$_{30}$H$_{44}$O$_3$ [(M+H)+], found 452.3290; UV (MeOH) λ$_{max}$ 263 nm (ϵ10790).

Example 5

Preparation of Analog 1n

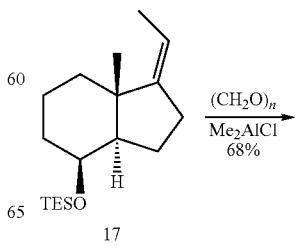

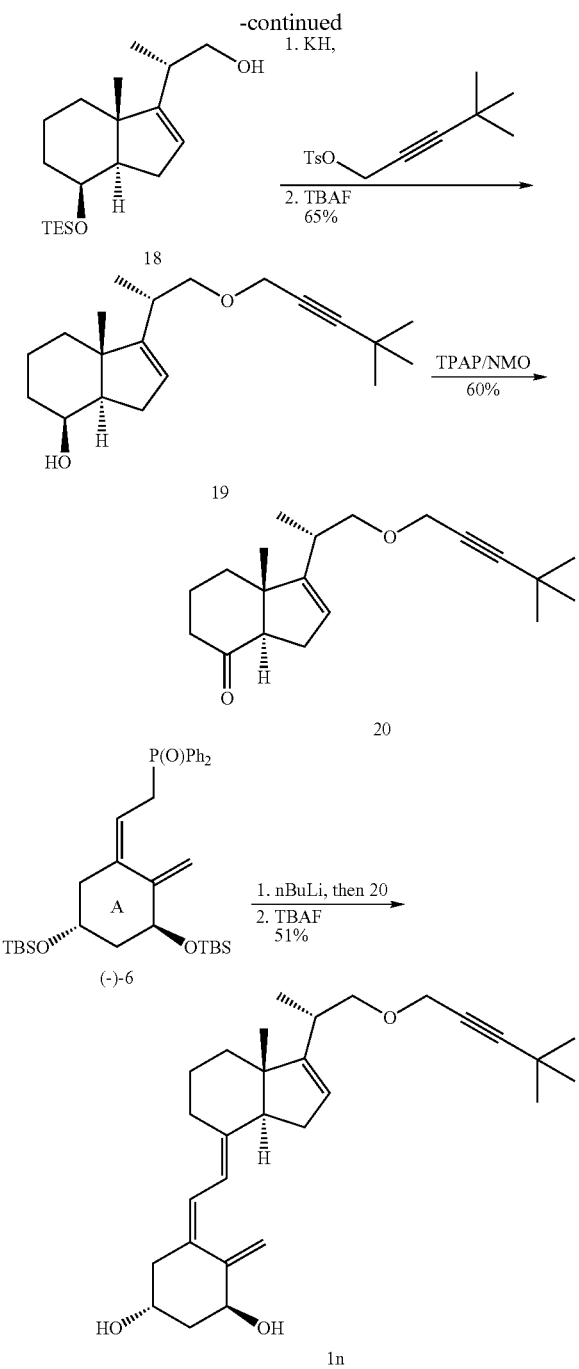

Alcohol 18

To a suspension of paraformaldehyde (272 mg, 9.1 mmol) in 50 mL of $CH_2Cl_2$ was added 13.5 mL (13.5 mmol) of 1 M dimethylaluminum chloride solution in hexanes at −78° C. After 30 min, a solution of (+)-17[6] (503 mg, 2.8 mmol) in 5 mL of $CH_2Cl_2$ was added into the mixture at −78° C., and then the reaction mixture was warmed to −40° C. After being stirred for 16 h at −40° C., it was quenched with 10% $K_2HPO_4$ at −40° C. and then warmed to room temperature. The reaction mixture was extracted with ethyl acetate (2×100 mL), washed with 10% HCl, saturated aqueous $NaHCO_3$ solution, and brine, dried, concentrated in vacuo, and then purified by chromatography (50% ethyl acetate/hexanes) to give 400 mg (68%) of (+)-18 as an oil. $[\alpha]_D^{25}$+1.63° (c 3.2, $CHCl_3$); IR ($CHCl_3$, $cm^{-1}$) 3579, 2937, 1727; $^1H$ NMR (400 MHz, $CDCl_3$) δ 5.40 (t, J=1.6 Hz, 1H), 5.21 (m, 1H), 3.57 (m, 2H), 2.34 (m, 1H), 2.10 (m, 2H), 2.04 (s, 3H), 1.81 (m, 4H), 1.57 (m, 3H), 1.41 (m, 1H), 1.01 (d, J=6.8 Hz, 3H), 1.00 (s, 3H); $^{13}C$ NMR (100 MHz, $CDCl_3$) δ 156.97, 121.66, 70.56, 66.57, 52.85, 46.52, 34.82, 34.60, 30.65, 21.34, 18.41, 17.90, 12.35; HRMS m/z calcd for $C_{13}H_{21}O$ 193.1593, found 193.1596.

Alcohol 19

Dry hexanes washed KH (16 mg, 9.0 eq., 0.40 mmol) was added to a 25 mL receiving flask. A solution of alcohol 18 (15 mg, 0.044 mmol) in 2.5 mL of THF was added to the KH and allowed to stir for 45 minutes at room temperature. Propargyltosylate (61 mg, 0.23 mmol) was added and the reaction was allowed to stir at room temperature overnight. The reaction was quenched with water, extracted with ethyl acetate, dried over anhydrous $MgSO_4$, filtered, and concentrated in vacuo. The crude TES-protected alcohol was dissolved in 2.5 mL of THF and TBAF (0.13 mL, 0.13 mL of a 1 M solution in THF) was added to the solution. The mixture was allowed to stir overnight, quenched with water, extracted with ethyl acetate, dried over anhydrous $MgSO_4$, filtered and purified by column chromatography to yield 19 in 65% yield (20 mg) for two steps as a colorless oil. $[\alpha]_D^{25}$=+14.8 (c 0.75, $CHCl_3$); IR (neat, $cm^{-1}$) 3466 (br), 2966 (s), 2933 (s), 2700 (m), 2242 (w), 1658 (w), 1475 (w), 1450 (w), 1367 (w), 1259 (w), 1209 (w), 1092 (m), 992 (w), 942 (w); $^1H$ NMR ($CDCl_3$, 400 MHz) δ 4.09 (m, 3H), 3.45 (dd, 1H, J=8.8, 3.2 Hz), 3.24 (dd, 1H, J=8.8, 6.8 Hz), 1.99 (m, 1H), 1.92-1.03 (m, 22 H), 1.02 (d, 3H, J=6.8 Hz), 0.95 (s, 3H); $^{13}C$ NMR ($CDCl_3$, 100 MHz) δ156.97, 121.66, 94.84, 74.80, 74.68, 69.32, 58.62, 53.35, 52.37, 41.88, 40.18, 36.07, 33.61, 30.98, 27.42, 26.63, 22.56, 17.45, 17.41, 13.56; HRMS (FAB) calcd for $C_{20}H_{32}O_2$, 304.24036; found, 304.2401.

Ketone 20

Alcohol 19 (20 mg, 1.0 eq., 0.07 mmol), NMO (N-morpholine-N-oxide) (13 mg, 1.5 eq., 0.11 mmol), and 4 Å molecular sieves were dissolved in 2 mL of $CH_2Cl_2$ in 50 mL receiving flask. After stirring for 10 minutes, TPAP (1.5 mg, 0.05 eq., 0.004 mmol) was added and the reaction was followed by TLC. After 3 hours the reaction was quenched with water, filtered, extracted with $CH_2Cl_2$, dried over anhydrous $MgSO_4$, and purified by column chromatography to yield ketone 20 in 50% yield. $[\alpha]_D^{25}$=+1.22 (c 0.50, $CHCl_3$); IR (neat, $cm^{-1}$) 2968, 2929, 2849, 1714, 1476, 1456, 1381(m), 1358, 1306, 1264, 1239, 1096, 1010, 942, 834; $^1H$ NMR ($CDCl_3$, 400 MHz) δ4.09 (m, 2H), 3.43 (dd, 1H, J=8.8, 2.8 Hz), 3.29 (dd, 1H, J=8.8, 6.4 Hz), 2.45 (dd, 1H, J=11.6, 7.6 Hz), 2.28-1.28 (m, 11H), 1.22 (s, 9H), 1.07 (d, 3H, J=6.4 Hz), 0.64 (s, 3H); $^{13}C$ NMR ($CDCl_3$, 100 MHz) δ211.88, 156.97, 121.66, 94.98, 74.62, 74.36, 61.68, 58.66, 53.30, 49.85, 40.94, 38.75, 36.24, 30.94, 29.67, 26.94, 24.02, 19.09, 17.65, 12.47; HRMS (FAB) calcd for $C_{20}H_{30}O_2$, 302.2247; found, 302.2250.

Analog 1n

Enantiomerically pure phosphine oxide 6 and CD-ring ketone 20, were separately azeotropically dried with anhydrous benzene (3×2 mL) on a rotary evaporator and held under vacuum for 120 hours prior to use. A flame-dried 10 mL round-bottom flask equipped with a magnetic stir bar and an Ar balloon was charged with phosphine oxide 6 (35 mg, 0.060 mmol), dissolved in 1 mL of freshly distilled THF, and cooled to −78° C. To this solution, n-BuLi (33 µL, 0.054 mmol, 1.6 M in hexanes) was added drop-wise over 5 minutes during which time a deep red color developed and persisted. This mixture was allowed to stir at −78° C. for an additional 25 minutes. Meanwhile, a flame-dried 10 mL round-bottomed flask containing CD-ring ketone 20 (10 mg, 0.028 mmol) was dissolved in 1 mL of THF and cooled to −78° C. This solution was transferred drop-wise into the flask containing phosphine oxide anion at −78° C. via cannula over 5 minutes. After the addition was complete, the deep red color persisted and the reaction was allowed to stir at −78° C. for 4 hours. Upon observation of a light yellow color, the reaction was quenched with 3 mL of pH=7 buffer and allowed to warm to room temperature. The mixture was extracted with ethyl acetate (1×5 mL) and methylene chloride (2×5 mL). The combined organic extracts were dried over MgSO$_4$ and filtered. The filtrate was concentrated in vacuo to give crude product that was purified by column chromatography (10% ethyl acetate in hexanes with 1% NEt$_3$), affording the protected analog. The protected analog was dissolved in 2 mL of THF and TBAF (100 µL, 1.6 M solution in THF) was added and the mixture was allowed to stir overnight. The reaction was quenched with water, extracted with ethyl acetate (1×5 mL) and methylene chloride (2×5 mL). The combined organic extracts were dried over MgSO$_4$ and filtered. The filtrate was concentrated in vacuo, and the crude product was purified by column chromatography (70% ethyl acetate in hexanes with 1% NEt$_3$) to afford 1n (2.3 mg, 0.005 mmol, 51%) as a colorless oil. $[\alpha]_D^{25}$=+14.6 (c=0.35, CHCl$_3$); IR (thin film) 3300, 2960, 2873, 1651, 1487, 1375, 932, 870 cm$^{-1}$; $^1$H NMR (400 MHz, CDCl$_3$) δ 6.25 (d, J=11.2 Hz, 1H), 6.09 (d, J=11.2 Hz, 1H), 5.32 (t, J=1.6 Hz, 1H), 5.30 (m, 1H), 5.00 (m, 1H), 4.42-4.44 (m, 1H), 4.20-4.4.26 (m, 1H), 3.80 (bs, 1H), 2.78-2.83 (m, 1H), 2.40-2.61 (m, 3H), 2.29-2.38 (m, 2H), 2.13-2.24 (m, 2H), 1.90-1.93 (m, 2H), 1.60-1.89 (m, 6H), 1.45-1.54 (m, 1H), 1.35 (s, 3H), 1.34 (s, 3H), 1.04 (d, J=6.8 Hz, 3H), 0.66 (s, 3H); $^{13}$C NMR (100 MHz, CDCl$_3$) δ 158.60, 151.55, 147.65, 143.10, 132.91, 124.98, 117.04, 111.76, 94.88, 74.78, 70.84, 66.85, 58.61, 56.07, 53.23, 45.95, 45.27, 42.87, 40.26, 36.86, 31.92, 29.69, 27.11, 25.50, 23.55, 18.76, 11.26; HRMS (FAB) calcd 438.3156 for C$_{29}$H$_{42}$O$_3$, found 438.3156; UV (MeOH) $\lambda_{max}$ 260 nm (ε10800).

Example 6

Preparation of Analog 1o

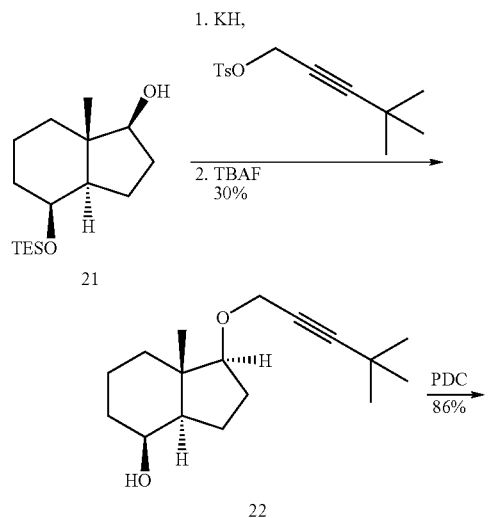

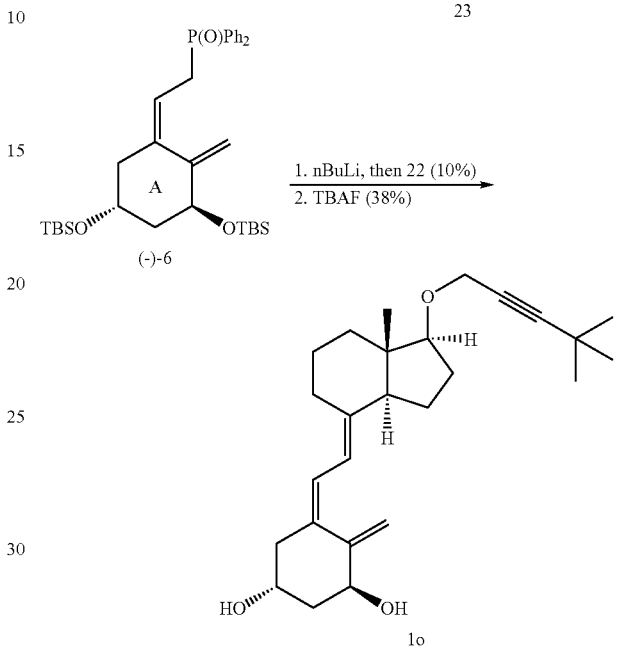

Alcohol 22

A flame dried 10 mL round bottom flask equipped with a magnetic stir bar and an Ar balloon was charged with 21[8] (48 mg, 0.17 mmol) in 2 mL of freshly distilled THF and cooled to 0° C. To this solution, n-butyl lithium (0.11 mL, 0.17 mmol, 1.6 M in hexane) was added drop wise over 5 min and this mixture was allowed to stir at 0° C. for 20 min, then was warmed to room temperature and stirred 16 h. When consumption of the starting material was seen via TLC analysis, the reaction was quenched with a H$_2$O (5 mL). The aqueous layer was extracted with diethyl ether (3×5 mL), and the organics were washed with a saturated solution of brine (10 mL), dried over MgSO$_4$ and filtered. The filtrate was concentrated in vacuo, and the crude product was purified by column chromatography (0-10% diethyl ether in hexanes) to afford the intermediate ether. A flame dried 10 mL round bottom flask equipped with a magnetic stirbar and an Ar ballon was charged with the intermediate ether (21 mg, 0.056 mmol) in 2 mL of freshly distilled THF. To this solution, tetrabutyl ammonium fluoride (0.28 mL, 0.28 mmol, 1.0 M in THF) was added dropwise and this mixture was allowed to stir for 16 h. When consumption of the starting material was seen via TLC analysis, the reaction was quenched with H$_2$O (3 mL). The aqueous layer was extracted with CH$_2$Cl$_2$ (3×5 mL). The organics were washed with a saturated solution of brine (10 mL), dried over MgSO$_4$ and filtered. The filtrate was concentrated in vacuo, and the crude product was purified by column chromatography (10% ethyl acetate in hexane) to afford 22 as a clear oil (13 mg, 0.051 mmol, 30% yield over 2 steps). $[\alpha]_D^{23}$=+7.2 (c=0.67, CHCl$_3$); IR (thin film) 3477, 2966, 2927, 2864, 1454, 1361, 1263, 1086, 989, 962, 893, 720 cm$^{-1}$; $^1$H NMR (400 MHz, CDCl$_3$) δ 4.13 (s, 2H), 4.04 (d, 1H, J=2.8 Hz), 3.47 (t, 1H, J=8 Hz), 2.06-1.71 (m, 5H), 1.54-1.24 (m, 7H), 1.21 (s, 9H), 1.01 s, 3H; $^{13}$C NMR (100 MHz, CDCl$_3$) δ 94.5, 87.8, 74.5, 69.2, 57.8, 47.7, 41.9, 38.2, 33.7, 30.9, 27.4, 26.9, 21.7, 17.1, 13.1; HRMS (FAB) calc 265.2168 for C$_{17}$H$_{29}$O$_2$ [(M+H)$^+$], found 265.2159.

Ketone 23

A flame dried 10 mL round bottom flask equipped with a magnetic stir bar and an Ar balloon was charged with the alcohol 22 (13 mg, 0.049 mmol) in 2.0 mL of methylene chloride To this solution, PDC (55 mg, 0.15 mmol) and Celite® (60 mg) were added and the reaction stirred for 18 hr. When consumption of the starting material was seen via TLC analysis, the reaction was charged directly to a column and purified by column chromatography (0-15% ethyl acetate in hexanes) to afford 23 (11 mg, 0.043 mmol, 86%) as a colorless oil. [α]$_D^{25}$=−7.3 (c=0.57, CHCl$_3$); IR (thin film) 2967, 2868, 1715, 1454, 1361, 1263, 1226, 1102, 483 cm$^{-1}$; $^1$H NMR (400 MHz, CDCl$_3$) δ 4.14 (q, 2H, J=13 Hz), 3.79 (t, 1H, J=8 Hz), 2.42-1.86 (m, 8H), 1.58-1.5 (m, 3H), 1.22 (s, 9H), 0.72 (s, 3H); $^{13}$C NMR (100 MHz, CDCl$_3$) δ 209.4, 94.8, 87.1, 74.9, 57.8, 57.6, 49.3, 40.9, 36.7, 30.9, 27.4, 26.9, 23.7, 18.2, 12.0.

Analog 1o

Enantiomerically pure phosphine oxide 6 and C,D-ring ketone 23, were separately azeotropically dried with anhydrous benzene (3×2 mL) on a rotary evaporator and held under vacuum for 120 hr prior to use.

A flame dried 10 mL pear shaped flask equipped with a magnetic stir bar and an Ar balloon was charged with phosphine oxide 6 (45 mg, 0.077 mmol), dissolved in 1 mL of freshly distilled THF and cooled to −78° C. To this solution, n-BuLi (52 µL, 0.077 mmol, 1.6 M in hexanes) was added drop-wise over 5 min during which time a deep red color developed and persisted. This mixture was allowed to stir at −78° C. for an additional 25 min. Meanwhile, a flame-dried 10 mL round bottom flask containing C,D-ring ketone 23 (8 mg, 0.031 mmol) was dissolved in 1 mL of THF and cooled to −78° C. This solution was transferred drop-wise into the flask containing the phosphine oxide anion at −78° C. via cannula over 5 min. After the addition was complete, the deep red color persisted and the mixture was allowed to stir at −78° C. for 6 hr. Upon observation of a light yellow color, the reaction was quenched with 3 mL of pH=7 buffer and allowed to warm to room temperature. The mixture was extracted with ethyl acetate (1×5 mL) and methylene chloride (2×5 mL). The combined organic extracts were dried over MgSO$_4$ and filtered. The filtrate was concentrated in vacuo to give crude product that was purified by column chromatography (0-15% ethyl acetate in hexanes with 1% NEt$_3$), affording the protected analog along with a major side product (4.7 mg, 0.0075 mmol, 10%). The protected analog was dissolved in acetonitrile (2 mL) and tetrabutyl ammonium fluoride (100 µL, 0.1 mmol, 1.0 M in THF) was added. After stirring for 24 hr, the reaction was quenched with H$_2$O (5 mL) and allowed to stir until gas ceased to evolve. The aqueous layer was extracted with ethyl acetate (3×5 mL), dried over MgSO$_4$ and filtered. The filtrate was concentrated in vacuo, and the crude product was purified by column chromatography (60% ethyl acetate in hexanes with 1% NEt$_3$) to afford 1o (1 mg, 0.0024 mmol, 38%) as a colorless oil. $^1$H NMR (400 MHz, CDCl$_3$) δ 6.37 (d, 1H, J=12 Hz), 6.01 (d, 1H, J=11 Hz), 5.35 (s, 1H), 5.01 (s, 1H), 4.44 (m, 1H), 4.22 (m, 1H), 4.14 (d, 2H, J=6 Hz), 3.69 (t, 1H, J=8 Hz), 2.84 (m, 1H), 2.58 (m, 1H), 2.34-0.58 (m, 27H with s at 1.17 and 0.58); HRMS (FAB) calc 421.2721 for C$_{26}$H$_{38}$O$_3$Na$^+$ [(M$^+$Na)$^+$], found 421.2708.

Example 7

Preparation of Dermatological Creams

Any of the disclosed compounds of formula I may be dissolved in 1 g of almond oil. To this solution may be added 40 g of mineral oil and 20 g of self-emulsifying beeswax. The mixture may be heated to liquefy. After the addition of 40 ml hot water, the mixture may be mixed well, wherein the resulting cream contains approximately 10 µg of the compound of formula I per gram of cream.

Example 8

Preparation of Capsules

Any of the disclosed compounds of formula I may be dissolved in a triglyceride of a medium chain fatty acid to a final concentration of 50 µg/ml oil. 10 parts by weight of gelatin, 5 parts by weight glycerine, 0.08 parts by weight potassium sorbate, and 14 parts by weight of distilled water may be mixed together with heating and formed into soft gelatin capsules. These capsules may be filled each with 100 µl of the oil solution, such that each capsule contained 5 µg of the compound of formula I.

Example 9

VDR Binding Experiment

A competitive binding assay was performed according to Jones et al. (1980) and Fujishima et al. (2001), with some modifications[9,10]. Briefly, human recombinant VDR (1 pmol/reaction; Biomol, Plymouth Meeting, Pa., USA, Cat# SE-140) prepared in binding buffer (50 mM Tris-HCl pH 7.4, 1.5 mM EDTA, 300 mM KCl, 5 mg/ml gelatin and 10 mM DTT) was pre-incubated with 1α,25(OH)$_2$D$_3$ (10$^{-8}$-10$^{-10}$ M) or compound (10$^{-6}$-10$^{-10}$ M) for 1 h at room temperature. Then, 0.25 nM of [$^3$H]1α,25(OH)$_2$D$_3$ (~20,000 cpm; Perkin Elmer, Boston, Mass., USA, Cat# NET626) was added to the solution, mixed thoroughly and incubated for 1 h at room temperature. Unbound radioactive ligand was removed by incubation on ice for 30 min with charcoal-dextran, and then pelleted by centrifugation at 2000 rpm at 4° C. for 10 min. The radioactivity in 100 µl of the supernatant was measured using a scintillation counter. The control reactions contained either no VDR protein (background) or no competing ligand (maximum binding). The VDR binding assay results for compounds 1a, 1b, 1c, 1d, 1f, 1g, 1 h, and 1i are shown in FIGS. 2-9, respectively.

Example 10

CYP24 Induction

Assay[11,12]

Cell Culture, Stimulation & Plating

HPK1a-ras cells were propagated in DMEM+10% FBS (Invitrogen) to a level of 80% confluence. Cells were pelleted by centrifugation and resuspended to a concentration of 100×10$^3$ cells per 1 ml media. To each well of a 24-well plate, 1 ml of cell suspension was added and incubated overnight at 37° C.+5% CO$_2$.

Cell Treatment & TRIzol Addition

The cells were washed with PBS and then 1 ml DMEM+1% BSA media was added per well. To each well, 1 µl of the working solutions of 1, 10, and 100 nM of each compound was added. As a control, 1 µl of isopropanol was added to untreated cells, in duplicate. The cells were incubated at 37° C.+5% $CO_2$ for 8 hours, lysed in TRIzol reagent (Invitrogen, Cat #15596-018) and stored at −80° C. Each treatment was done in duplicate.

RNA Isolation and cDNA Synthesis

RNA was isolated from cell lysates in TRIzol through phase separation, RNA precipitation, and RNA wash as per the manufacturer's instructions (Invitrogen). The concentration of RNA was determined using a Spectrophotometer to measure the optical density of each sample, at a wavelength of 260 nm. The ThermoScript™ RT-PCR System kit (Invitrogen, Cat #11146-016) was used to create cDNA from 1 µg of RNA, as per manufacturer's instructions.

CYP24/GAPDH TaqMan® Real Time PCR

The commercial TaqMan® probes, from Applied Biosystems Inc. (ABI—Foster City, Calif.), for human CYP24 and GAPDH were used to determine to the amount of mRNA of CYP24 and GAPDH present in each sample, respectively. Both genes were detected in the same 20 µl reaction, carried out in an ABI PRISM 96-well optical reaction plate. The reaction was setup as per manufacturer's instructions, performed in triplicate and cycled 50 times using an ABI Prism 7000 Sequence Detection System®.

The relative fold induction of CYP24 by 100 nM for some of the disclosed compounds is provided below in Table II:

TABLE II

| Analog | Relative Fold Induction of CYP24 by 100 nM of Compound (%) |
|---|---|
| 1a | 89.8 |
| 1b | 9.8 |
| 1c | 1.4 |
| 1d | 73.8 |
| 1g | 5.8 |
| 1h | 2.3 |
| 1i | 18.3 |
| 1f | 0.3 |
| Calcitriol | 100.0 |

REFERENCES

1. Peleg, S.; Petersen, K. S.; Suh, B. C.; Dolan, P.; Agoston, E. S.; Kensler, T. W.; Posner, G. H. *J. Med. Chem.* 2006, 49, 7513-7517.
2. Petersen, K. S.; Dolan, P. M.; Kensler, T. W.; Peleg, S.; Posner, G. H. *J. Med. Chem.* 2007, 50, 5824-5832.
3. Posner, G. H.; Lee, J. K.; White, M. C.; Hutchings, R. H.; Dai, H.; Kachinski, J. L.; Dolan, P.; Kensler, T. W. *J. Org. Chem.* 1997, 62, 3299-3314.
4. Daniewski, A. R.; Garofalo, L. M.; Hutchings, S. D.; Kabat, M. M.; Liu, W.; Okabe, M.; Radinov, R.; Yiannikouros, G. P. *J. Org. Chem.* 2002, 67, 1580-1587.
5. Posner, G. H.; Suh, B. C.; Petersen, K. S.; Dolan, P.'Agoston, E. S.; Kensler, T. W.; Koh, J. T.; Peleg, S. *J. Steroid Biochem. Mol. Biol.* 2007, 103, 213-221.
6. Hatcher, M. A.; Posner, G. H. *Tetrahedron Lett.* 2002, 43, 5009-5012.
7. Schelper, M.; Meijere, A. *Eur. J. Org. Chem.* 2005, 3, 582-592.
8. Moman, E. N. D.; Mourino, A. *J. Org. Chem.* 2004, 69, 4615-4625.
9. Ross T K, Prahl J M, DeLuka H. Overproduction of rat 1,25-dihydroxyvitamin D3 receptor in insect cells using the baculovirus expression system. (1991) Proc Natl Acd Sci USA 88:6555-6559.
10. Wecksler W R, Norman A W. An hydroxylapatite batch assay for the quantitation of 1alpha, 25-dihydroxyvitamin D3-receptor complexes (1979) Anal Biochem 92:314-323.
11. Hashimoto Y, Ikeda I, Ikeda M, Takahashi Y, Hosaka M, Uchida H, Kono N, Fukui H, Makino T, Honjo M. Construction of a specific and sensitive sandwich enzyme immunoassay for 20 KD human growth hormone (1998) J Immunol Methods 221:77-85.
12. Jone G, Byford V, Makin H L J, Kremer R, Rice R H, deGraffenried, L A, Knutson J C, Bishop C W. Antiproliferative activity and target cell catabolism of the vitamin D analogue 1 alpha, 24(OH)2D2 in normal and immortalized human epidermal cells (1996) Biochem Pharmacol 52:133-140.

Those with ordinary skill in the art will recognize methods for substitution of the positions of the core structures described herein that may be made while maintaining anti proliferative activity. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having formula I:

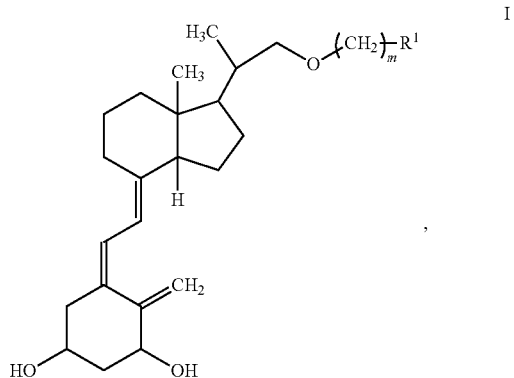

or a pharmaceutically acceptable salt thereof, wherein:

m is an integer from 0 to 1;

$R^1$ is selected from the group consisting of

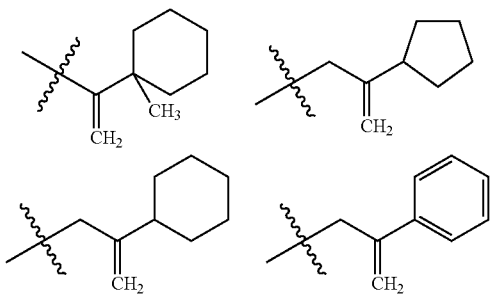

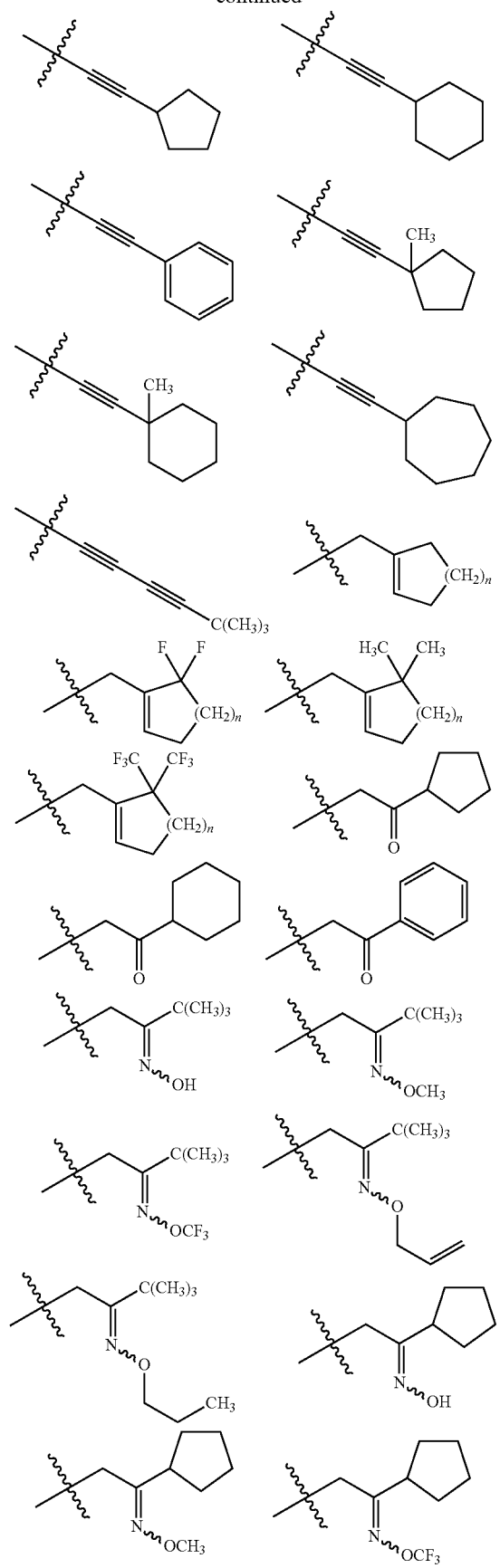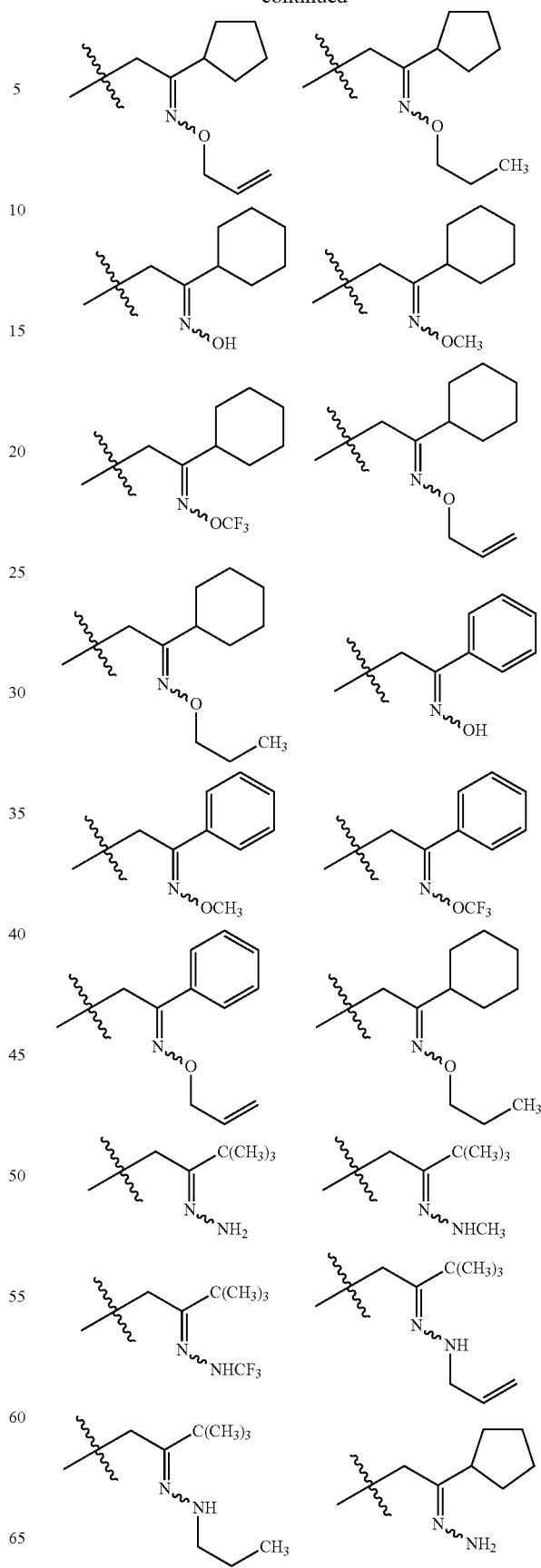

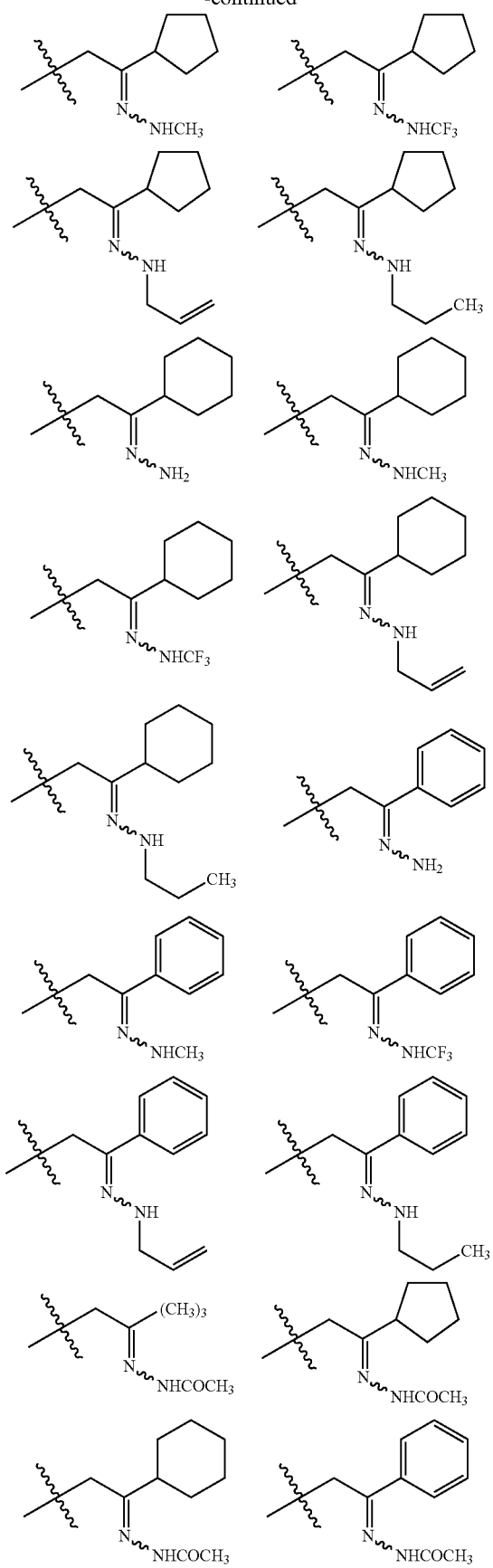
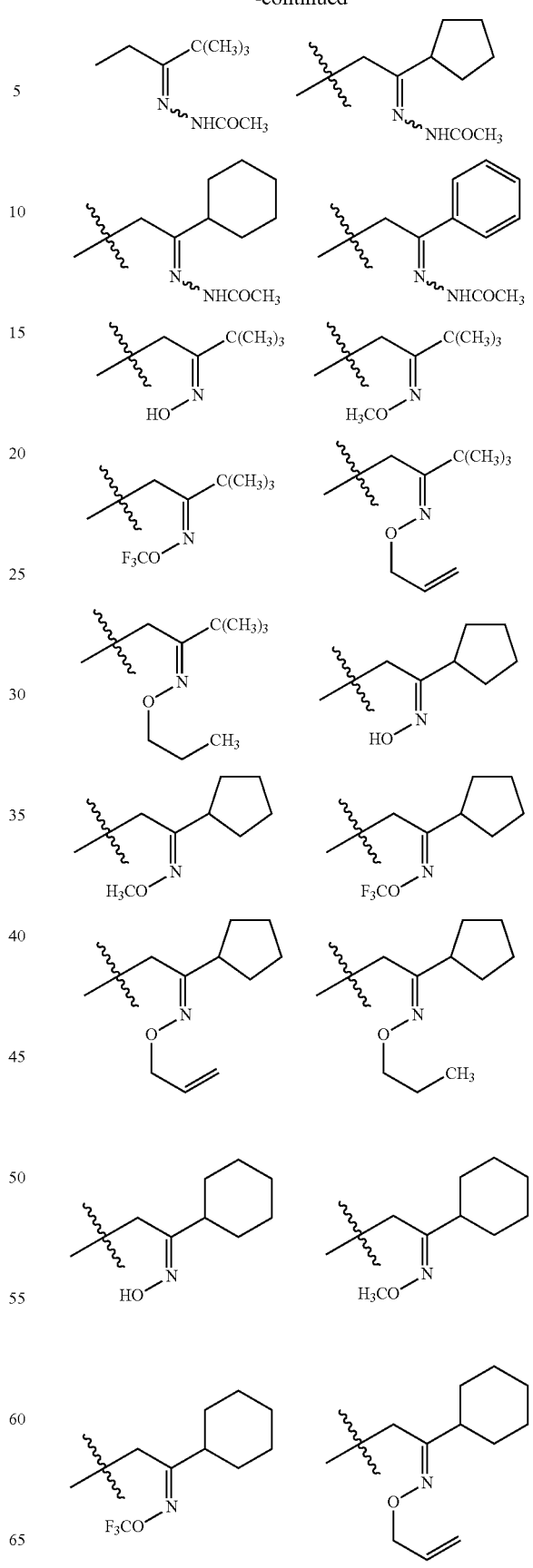

-continued
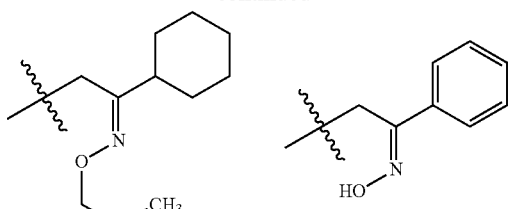
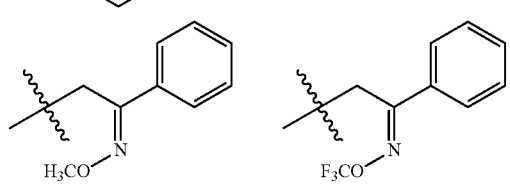
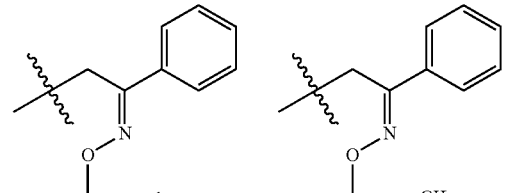
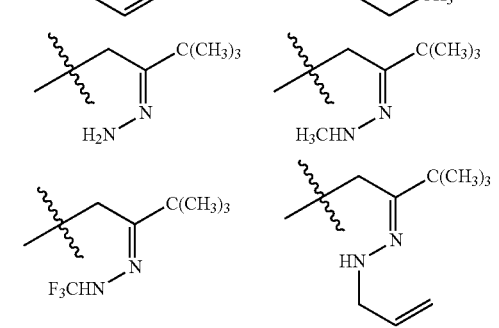
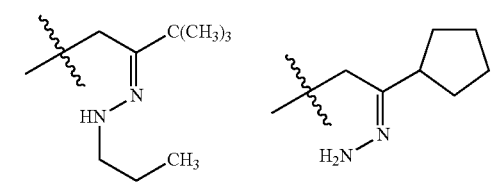
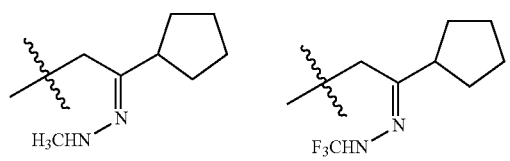
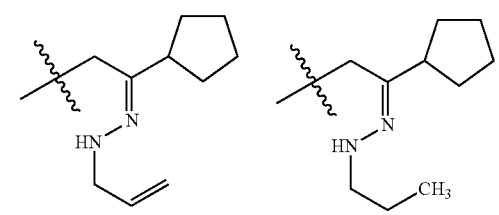
-continued
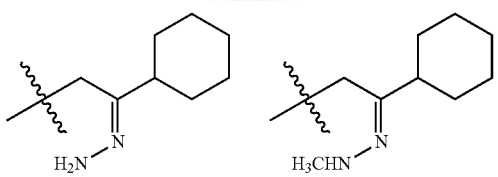
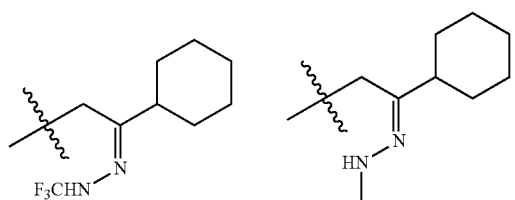
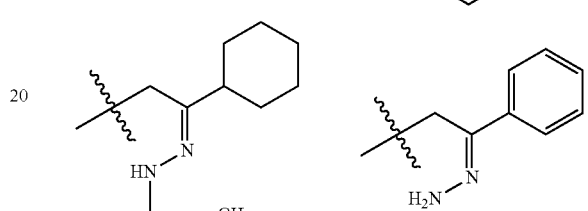
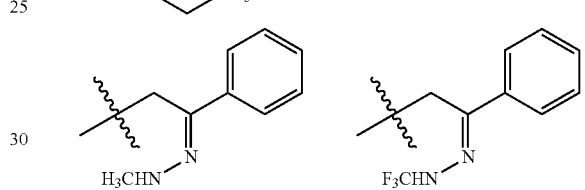
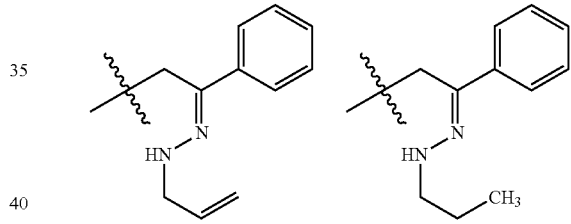
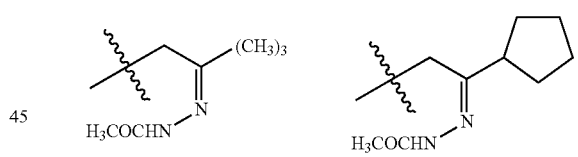
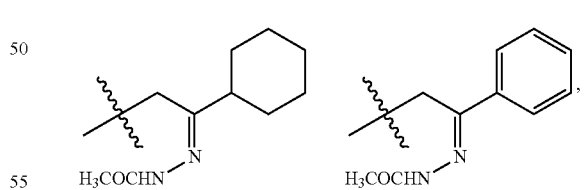
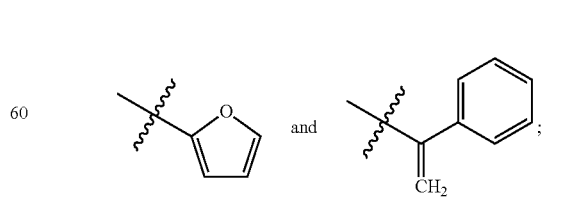
and
each n is independently an integer from 0 to 2.

2. The compound of claim 1, wherein the compound of formula I has formula IV:

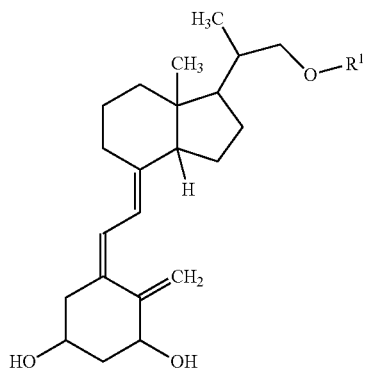

or a pharmaceutically acceptable salt thereof.

3. A method of treating a disorder characterized by abnormal cell-proliferation and/or cell-differentiation, comprising administering to a subject in need thereof a therapeutically effective amount of a compound of Formula I of claim 1, wherein the disorder is selected from the group consisting of leukemia, myelofibrosis and psoriasis.

4. A method of treating secondary hyperparathyroidism, comprising administering to a subject in need thereof a therapeutically effective amount of a compound of Formula I of claim 1.

5. A method of preparing the compound of formula I of claim 1, comprising:

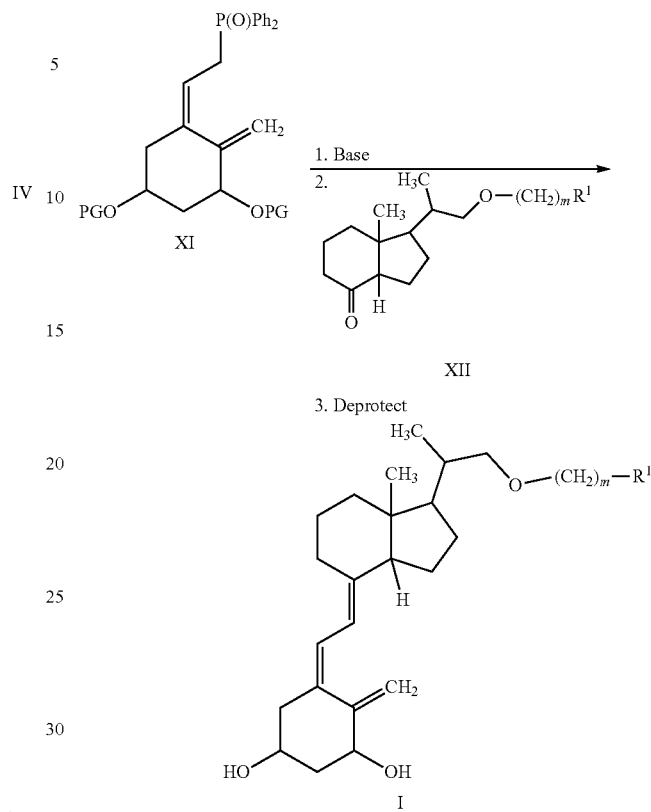

a) reacting the compound of formula XI with base to form the corresponding anion;
b) coupling the anion with the compound of formula XII, wherein PG is a protecting group; and
c) removing the protecting groups to provide the compound of formula I.

6. The method of claim 5, wherein the base is an alkali metal hydride or organolithium compound; and the protecting group is a silyl protecting group.

* * * * *